(12) United States Patent
Zhou et al.

(10) Patent No.: US 7,687,456 B2
(45) Date of Patent: *Mar. 30, 2010

(54) COMPOUNDS FOR ENZYME INHIBITION

(75) Inventors: Han-Jie Zhou, Foster City, CA (US);
Congcong M. Sun, Cupertino, CA (US);
Kevin D. Shenk, Palo Alto, CA (US);
Guy J. Laidig, Menlo Park, CA (US)

(73) Assignee: Proteolix, Inc., South San Francisco, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 11/595,804

(22) Filed: Nov. 9, 2006

(65) Prior Publication Data

US 2007/0105786 A1    May 10, 2007

Related U.S. Application Data

(60) Provisional application No. 60/842,582, filed on Sep. 5, 2006, provisional application No. 60/736,118, filed on Nov. 9, 2005.

(51) Int. Cl.
*A61K 38/00* (2006.01)

(52) U.S. Cl. .......................................... 514/2; 530/300

(58) Field of Classification Search ........................ None
See application file for complete search history.

(56) References Cited

U.S. PATENT DOCUMENTS

| | | | |
|---|---|---|---|
| 6,235,717 B1 | 5/2001 | Leban et al. | |
| 6,831,099 B1 | 12/2004 | Crews et al. | |
| 2006/0241056 A1 | 10/2006 | Orlowski et al. | |
| 2008/0090785 A1* | 4/2008 | Smyth et al. | ........... 514/99 |

FOREIGN PATENT DOCUMENTS

| | | |
|---|---|---|
| WO | WO-94/15956 | 7/1994 |
| WO | WO-01/28579 A2 | 4/2001 |
| WO | WO-2005/105827 A2 | 11/2005 |
| WO | WO-2005/111008 A2 | 11/2005 |
| WO | WO-2006/045066 A | 4/2006 |
| WO | WO-2006/099261 A2 | 9/2006 |
| WO | WO-2007/056464 A | 5/2007 |

OTHER PUBLICATIONS

Elofsson et al., "Towards subunit-specific proteasome inhibitors: synthesis and evaluation of peptide α',β'-epoxyketones", *Chemistry & Biology*, vol. 6, pp. 811-822, 1999.

Myung et al., "Lack of Proteasome Active Site Allostery as Revealed by Subunit-Specific Inhibitors," *Molecular Cell*, vol. 7, No. 2, pp. 411-420, 2001.

Sin et al., "Total synthesis of the potent proteasome inhibitor epoxomicin: a useful tool for understanding proteasome biology", *Bioorganic & Medicinal Chemistry Letters*, vol. 9, pp. 2283-2288, 1999.

International Search Report from PCT/US2007/014427, dated Dec. 3, 2007.

Written Opinion of the International Searching Authority for PCT/US2007/014427, dated Dec. 22, 2008.

International Search Report from PCT/US2008/005997, mailed Nov. 7, 2008.

Myung et al., "The Ubiquitin-Proteasome Pathway and Proteasome Inhibitors," *Medicinal Research Reviews*, vol. 21, No. 4, pp. 245-273, 2001.

Overkleeft et al., "Solid phase synthesis of peptide vinyl sulfone and peptide epoxyketone proteasome inhibitors," *Tetrahedron Letters*, 41(32):6005-6009 (2000).

European Search Report from EP 08 16 4241 dated Jan. 22, 2009.

* cited by examiner

*Primary Examiner*—Andrew D Kosar
*Assistant Examiner*—Satyanarayana R Gudibande
(74) *Attorney, Agent, or Firm*—Ropes & Gray LLP

(57) ABSTRACT

Peptide-based compounds including heteroatom-containing, three-membered rings efficiently and selectively inhibit specific activities of N-terminal nucleophile (Ntn) hydrolases associated with the proteasome. The peptide-based compounds include an epoxide or aziridine, and functionalization at the N-terminus. Among other therapeutic utilities, the peptide-based compounds are expected to display anti-inflammatory properties and inhibition of cell proliferation. Oral administration of these peptide-based proteasome inhibitors is possible due to their bioavailability profiles.

49 Claims, No Drawings

COMPOUNDS FOR ENZYME INHIBITION

CROSS-REFERENCE TO RELATED APPLICATIONS

This application claims the benefit of U.S. Provisional Application No. 60/842,582, filed Sep. 5, 2006, and claims the benefit of U.S. Provisional Application No. 60/736,118, filed Nov. 9, 2005, the specifications of which are hereby incorporated by reference in their entirety.

BACKGROUND OF THE INVENTION

In eukaryotes, protein degradation is predominately mediated through the ubiquitin pathway in which proteins targeted for destruction are ligated to the 76 amino acid polypeptide ubiquitin. Once targeted, ubiquitinated proteins then serve as substrates for the 26S proteasome, a multicatalytic protease, which cleaves proteins into short peptides through the action of its three major proteolytic activities. While having a general function in intracellular protein turnover, proteasome-mediated degradation also plays a key role in many processes such as major histocompatibility complex (MHC) class I presentation, apoptosis, cell division, and NF-κB activation.

The 20S proteasome is a 700 kDa cylindrical-shaped multicatalytic protease complex comprised of 28 subunits organized into four rings that plays important roles in cell growth regulation, major histocompatibility complex class I presentation, apoptosis, antigen processing, NF-κB activation, and transduction of pro-inflammatory signals. In yeast and other eukaryotes, 7 different α subunits form the outer rings and 7 different β subunits comprise the inner rings. The α subunits serve as binding sites for the 19S (PA700) and 11S (PA28) regulatory complexes, as well as a physical barrier for the inner proteolytic chamber formed by the two β subunit rings. Thus, in vivo, the proteasome is believed to exist as a 26S particle ("the 26S proteasome"). In vivo experiments have shown that inhibition of the 20S form of the proteasome can be readily correlated to inhibition of 26S proteasome. Cleavage of amino-terminal prosequences of β subunits during particle formation expose amino-terminal threonine residues, which serve as the catalytic nucleophiles. The subunits responsible for catalytic activity in proteasome thus possess an amino terminal nucleophilic residue, and these subunits belong to the family of N-terminal nucleophile (Ntn) hydrolases (where the nucleophilic N-terminal residue is, for example, Cys, Ser, Thr, and other nucleophilic moieties). This family includes, for example, penicillin G acylase (PGA), penicillin V acylase (PVA), glutamine PRPP amidotransferase (GAT), and bacterial glycosylasparaginase. In addition to the ubiquitously expressed β subunits, higher vertebrates also possess three γ-interferon-inducible β subunits (LMP7, LMP2 and MECL1), which replace their normal counterparts, X, Y and Z respectively, thus altering the catalytic activities of the proteasome. Through the use of different peptide substrates, three major proteolytic activities have been defined for the eukaryote 20S proteasome: chymotrypsin-like activity (CT-L), which cleaves after large hydrophobic residues; trypsin-like activity (T-L), which cleaves after basic residues; and peptidylglutamyl peptide hydrolyzing activity (PGPH), which cleaves after acidic residues. Two additional less characterized activities have also been ascribed to the proteasome: BrAAP activity, which cleaves after branched-chain amino acids; and SNAAP activity, which cleaves after small neutral amino acids. The major proteasome proteolytic activities appear to be contributed by different catalytic sites, since inhibitors, point mutations in β subunits and the exchange of γ interferon-inducing β subunits alter these activities to various degrees.

In recent years, the proteasome has become an appealing target for therapeutic intervention in cancer, immune and auto-immune disorders, inflammation, ischemic conditions, neurodegenerative disorders and other diseases. To date, the only FDA-approved proteasome inhibitor is bortezomib (VELCADE™), however, several other proteasome inhibitors are currently being evaluated in clinical trials. Thus far, all these therapeutic proteasome inhibitors currently are administered via IV. Clinical application of proteasome inhibitors in the treatment of hematologic malignancies such as myeloma and lymphoma is restricted in part by the necessity of frequent IV administrations and would be improved by oral (PO) administration. However, due to the peptide nature of these molecules, systemic exposure following PO administration of these inhibitors is limited by several factors including gastric pH, gastric and intestinal peptidases, efflux pumps, biliary excretion and intestinal and hepatic metabolic activities.

Methods used to overcome the ability of peptides to be enzymatically degraded and to improve absorption into the blood stream from the digestive tract have included making analogs which are less peptide-like in structure and which are reduced in size. Such methods are deemed to be successful when the peptide analog achieves satisfactory blood levels after oral administration, or in the case of proteasome inhibitors, when the proteasome activity in blood is satisfactorily reduced.

The above mentioned techniques have been applied to preparing analogs of the peptide epoxyketone proteasome inhibitors, thereby rendering them orally bioavailable.

SUMMARY OF THE INVENTION

The invention relates to classes of molecules known as peptide α',β'-epoxides and peptide α',β'-aziridines. The parent molecules are understood to bind efficiently, irreversibly and selectively to N-terminal nucleophile (Ntn) hydrolases, and can specifically inhibit particular activities of enzymes having multiple catalytic activity.

Once thought merely to dispose of denatured and misfolded proteins, the proteasome is now recognized as constituting proteolytic machinery that regulates the levels of diverse intracellular proteins through their degradation in a signal-dependent manner. Hence, there is great interest in identifying reagents that can specifically perturb the activities of the proteasome and other Ntn hydrolases and thereby be used as probes to study the role of these enzymes in biological processes. Compounds that target the Ntn hydrolases are herein described, synthesized, and investigated. Peptide epoxides and peptide aziridines that can potently, selectively, and irreversibly inhibit particular proteasome activities are disclosed and claimed.

Unlike several other peptide-based inhibitors, the peptide epoxides and peptide aziridines described herein are not expected to substantially inhibit non-proteasomal proteases such as trypsin, chymotrypsin, cathepsin B, papain, and calpain at concentrations up to 50 μM. At higher concentrations, inhibition may be observed, but would be expected to be competitive and not irreversible, if the inhibitor merely competes with the substrate. The novel peptide epoxides and peptide aziridines are also expected to inhibit NF-κB activation and to stabilize p53 levels in cell culture. Moreover, these compounds would be expected to have anti-inflammatory activity. Thus, these compounds can be unique molecular probes, which have the versatility to explore Ntn enzyme function in normal biological and pathological processes.

In one aspect, the invention provides inhibitors comprising a heteroatom-containing three-membered ring. These inhibitors can inhibit catalytic activity of N-terminal nucleophile hydrolase enzymes (for example, the 20S proteasome, or the 26S proteasome) when said inhibitor is present at concentrations below about 50 µM. Regarding the 20S proteasome, particular hydrolase inhibitors inhibit chymotrypsin-like activity of the 20S proteasome when the inhibitor is present at concentrations below about 5 µM, and does not inhibit trypsin-like activity or PGPH activity of the 20S proteasome when present at concentrations below about 5 µM. The hydrolase inhibitor may be, for example, a peptide α',β'-epoxy ketone or α',β'-aziridine ketone, and the peptide may be a tetrapeptide. The peptide may include branched or unbranched side chains such as hydrogen, $C_{1-6}$alkyl, $C_{1-6}$hydroxyalkyl, $C_{1-6}$alkoxyalkyl, aryl, $C_{1-6}$aralkyl, $C_{1-6}$alkylamide, $C_{1-6}$alkylamine, $C_{1-6}$carboxylic acid, $C_{1-6}$carboxyl ester, $C_{1-6}$alkylthiol, or $C_{1-6}$alkylthioether, for example isobutyl, 1-naphthyl, phenylmethyl, and 2-phenylethyl. The α'-carbon of the α',β'-epoxy ketone or α',β'-aziridine ketone may be a chiral carbon atom, such as an (R) or β configured carbon, as these are defined herein.

In another aspect, the invention provides pharmaceutical compositions, including a pharmaceutically acceptable carrier and a pharmaceutically effective amount of the hydrolase inhibitor, which ameliorates the effects of neurodegenerative disease (such as Alzheimer's disease), muscle-wasting diseases, cancer, chronic infectious diseases, fever, muscle disuse, denervation, nerve injury, fasting, and immune-related conditions, among others.

In another aspect, the invention provides compounds and pharmaceutical compositions that are orally bioavailable.

In another aspect, the invention provides anti-inflammatory compositions.

In another aspect, the invention provides methods for the following: inhibiting or reducing HIV infection in a subject; affecting the level of viral gene expression in a subject; altering the variety of antigenic peptides produced by the proteasome in an organism; determining whether a cellular, developmental, or physiological process or output in an organism is regulated by the proteolytic activity of a particular Ntn hydrolase; treating Alzheimer's disease in a subject; reducing the rate of muscle protein degradation in a cell; reducing the rate of intracellular protein degradation in a cell; reducing the rate of p53 protein degradation in a cell; inhibiting the growth of p53-related cancers in a subject; inhibiting antigen presentation in a cell; suppressing the immune system of a subject; inhibiting IκB-α degradation in an organism; reducing the content of NF-κB in a cell, muscle, organ or subject; affecting cyclin-dependent eukaryotic cell cycles; treating proliferative disease in a subject; affecting proteasome-dependent regulation of oncoproteins in a cell; treating cancer growth in a subject; treating p53-related apoptosis in a subject; and screening proteins processed by N-terminal nucleophile hydrolases in a cell. Each of these methods involves administering or contacting an effective amount of a composition comprising the hydrolase inhibitors disclosed herein, to a subject, a cell, a tissue, an organ, or an organism.

Other features and advantages of the invention will be apparent from the following detailed description, and from the claims.

DETAILED DESCRIPTION OF THE INVENTION

The invention involves compounds useful as enzyme inhibitors. These compounds are generally useful to inhibit enzymes having a nucleophilic group at the N-terminus. For example, activities of enzymes or enzyme subunits having N-terminal amino acids with nucleophiles in their side chains, such as threonine, serine, or cysteine can be successfully inhibited by the enzyme inhibitors described herein. Activities of enzymes or enzyme subunits having non-amino acid nucleophilic groups at their N-termini, such as, for example, protecting groups or carbohydrates, can also be successfully inhibited by the enzyme inhibitors described herein.

While not bound by any particular theory of operation, it is believed that such N-terminal nucleophiles of Ntn form covalent adducts with the epoxide functional group of the enzyme inhibitors described herein. For example, in the β5/Pre2 subunit of 20S proteasome, the N-terminal threonine is believed to irreversibly form a morpholino or piperazino adduct upon reaction with a peptide epoxide or aziridine such as those described below. Such adduct formation would involve ring-opening cleavage of the epoxide or aziridine.

In embodiments including such groups bonded to αcarbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule.

Regarding the stereochemistry, the Cahn-Ingold-Prelog rules for determining absolute stereochemistry are followed. These rules are described, for example, in *Organic Chemistry*, Fox and Whitesell; Jones and Bartlett Publishers, Boston, Mass. (1994); Section 5-6, pp 177-178, which section is hereby incorporated by reference. Peptides can have a repeating backbone structure with side chains extending from the backbone units. Generally, each backbone unit has a side chain associated with it, although in some cases, the side chain is a hydrogen atom. In other embodiments, not every backbone unit has an associated side chain. Peptides useful in peptide epoxides or peptide aziridines have two or more backbone units. In some embodiments useful for inhibiting chymotrypsin-like (CT-L) activity of the proteasome, between two and four backbone units are present, and in some preferred embodiments for CT-L inhibition, three backbone units are present.

The side chains extending from the backbone units can include natural aliphatic or aromatic amino acid side chains, such as hydrogen (glycine), methyl (alanine), isopropyl (valine), sec-butyl (isoleucine), isobutyl (leucine), phenylmethyl (phenylalanine), and the side chain constituting the amino acid proline. The side chains can also be other branched or unbranched aliphatic or aromatic groups such as ethyl, n-propyl, n-butyl, t-butyl, and aryl substituted derivatives such as 1-phenylethyl, 2-phenylethyl, (1-naphthyl)methyl, (2-naphthyl)methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with branched or unbranched $C_{1-6}$alkyl groups, or substituted alkyl groups, acetyl and the like, or further aryl groups, or substituted aryl groups, such as benzoyl and the like. Heteroaryl and heterocyclyl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like. Heterocyclyl groups include tetrahydrofuran, piperidine, piperazine, pyrrolidine, morpholine, lactones, lactams, and the like.

In some embodiments, polar or charged residues can be introduced into the peptide epoxides or peptide aziridines. For example, naturally occurring amino acids such as hydroxy-containing (Thr, Tyr, Ser) or sulfur-containing (Met, Cys) can be introduced, as well as non-essential amino acids, for example, taurine, carnitine, citrulline, cystine, ornithine, norleucine and others. Non-naturally occurring side chain substituents with charged or polar moieties can also be included, such as, for example, $C_{1-6}$alkyl chains or $C_{6-12}$aryl groups with one or more hydroxy, short chain alkoxy, sulfide, thio, carboxyl, ester, phospho, amido or amino groups, or such substituents substituted with one or more halogen atoms. In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example, N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by $\Delta^E$ or $\Delta^Z$ dehydro modification, in which a double bond is present between the α and β atoms of the side chain, or for example by $\Delta^E$ or $\Delta^Z$ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658-664, which is hereby incorporated by reference.

One aspect of the invention relates to compounds having a structure of formula (I) or a pharmaceutically acceptable salt thereof:

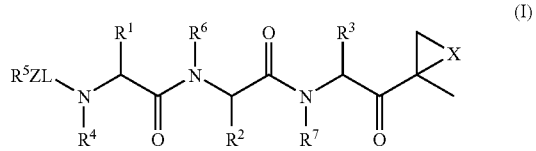

(I)

wherein

L is selected from C=O, C=S, and SO$_2$, preferably C=O;

X is selected from O, S, NH, and N—C$_{1-6}$alkyl;

Z is absent, $C_{1-6}$alkyl, or $C_{1-6}$alkoxy, preferably absent;

$R^1$, $R^2$, and $R^3$ are each independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclolalkyl;

$R^4$ is selected from hydrogen, $C_{1-6}$aralkyl, and $C_{1-6}$alkyl;
$R^5$ is heteroaryl; and
$R^6$ and $R^7$ are independently selected from hydrogen, $C_{1-6}$alkyl, and $C_{1-6}$aralkyl.

In certain embodiments, $R^1$, $R^2$, and $R^3$ are independently selected from hydrogen, $C_{1-6}$alkyl, $C_{1-6}$hydroxyalkyl, $C_{1-6}$alkoxyalkyl, $C_{1-6}$aralkyl, $C_{1-6}$heterocycloalkyl, $C_{1-6}$heteroaralkyl, and $C_{1-6}$carbocyclolalkyl. In certain embodiments, any of $R^1$, $R^2$, and $R^3$ are independently $C_{1-6}$alkyl selected from methyl, ethyl, propyl, isopropyl, butyl, sec-butyl, and isobutyl. In certain embodiments, any of $R^1$, $R^2$, and $R^3$ are independently $C_{1-6}$hydroxyalkyl. In certain preferred such embodiments, any of $R^1$, $R^2$, and $R^3$ are independently selected from hydroxymethyl and hydroxyethyl, preferably hydroxymethyl. In certain embodiments, any of $R^1$, $R^2$, and $R^3$ are independently $C_{1-6}$alkoxyalkyl. In certain such embodiments, any of $R^1$, $R^2$, and $R^3$ are independently selected from methoxymethyl and methoxyethyl, preferably methoxymethyl. In certain embodiments, any of $R^1$, $R^2$, and $R^3$ are independently $C_{1-6}$heteroaralkyl. In certain such embodiments, any of $R^1$, $R^2$, and $R^3$ are independently selected from imidazolylmethyl, pyrazolylmethyl, and thiazolylmethyl, and pyridylmethyl, preferably imidazol-4-ylmethyl, thiazol-4-ylmethyl, 2-pyridylmethyl, 3-pyridylmethyl, or 4-pyridylmethyl. In certain embodiments, any of $R^1$, $R^2$, and $R^3$ are independently $C_{1-6}$aralkyl. In certain such embodiments, any of $R^1$, $R^2$, and $R^3$ are independently selected from phenylmethyl (benzyl) and phenylethyl, preferably phenylmethyl. In certain embodiments, any of $R^1$, $R^2$, and $R^3$ are independently $C_{1-6}$carbocyclolalkyl. In certain such embodiments $R^1$ is cyclohexylmethyl. In certain embodiments $R^1$, $R^2$, and $R^3$ are all different. In certain embodiments, any two of $R^1$, $R^2$, and $R^3$ are the same. In certain embodiments, $R^1$, $R^2$, and $R^3$ are all the same.

In certain embodiments, at least one of $R^1$ and $R^2$ is selected from $C_{1-6}$hydroxyalkyl and $C_{1-6}$alkoxyalkyl. In certain such embodiments, at least one of $R^1$ and $R^2$ is alkoxyalkyl. In certain such embodiments, at least one of $R^1$ and $R^2$ is selected from methoxymethyl and methoxyethyl.

In certain embodiments, $R^3$ is selected from $C_{1-6}$alkyl and $C_{1-6}$aralkyl, preferably $C_{1-6}$alkyl. In certain such embodiments, $R^3$ is selected from methyl, ethyl, isopropyl, sec-butyl, and isobutyl. In certain such embodiments $R^3$ is isobutyl. In certain alternative embodiments, $R^3$ is selected from phenylmethyl and phenylethyl, preferably phenylmethyl.

In certain embodiments, $R^4$, $R^6$, and $R^7$ are independently selected from hydrogen and methyl, preferably hydrogen.

In certain embodiments, $R^5$ is a 5- or 6-membered heteroaryl. In certain such embodiments, $R^5$ is selected from isoxazole, isothiazole, furan, thiophene, oxazole, thiazole, pyrazole, or imidazole, preferably isoxazole, furan, or thiazole.

In certain embodiments, $R^5$ is a bicyclic heteroaryl. In certain such embodiments bicyclic heteroaryl is selected from benzisoxazole, benzoxazole, benzothiazole, benzisothiazole.

In certain embodiments, L is C=O, Z is absent, and $R^5$ is an isoxazol-3-yl or isoxazol-5-yl. In certain preferred such embodiments, when the isoxazol-3-yl is substituted, it is substituted at least at the 5-position. In certain preferred embodiments, when the isoxazol-5-yl is substituted, it is substituted at least at the 3-position.

In certain embodiments, L is C=O, Z is absent, and $R^5$ is an unsubstituted isoxazol-3-yl.

In certain embodiments, L is C=O, Z is absent, and $R^5$ is a substituted isoxazol-3-yl. In certain such embodiments, $R^5$ is isoxazol-3-yl substituted with a substituent selected from C$_{1-6}$alkyl, C$_{1-6}$alkoxy, C$_{1-6}$alkoxyalkyl, C$_{1-6}$hydroxyalkyl, carboxylic acid, aminocarboxylate, C$_{1-6}$alkylaminocarboxylate, (C$_{1-6}$alkyl)$_2$aminocarboxylate, C$_{1-6}$alkylcarboxylate, C$_{1-6}$heteroaralkyl, C$_{1-6}$aralkyl, C$_{1-6}$heterocycloalkyl, and C$_{1-6}$carbocycloalkyl. In certain preferred such embodiments R$^5$ is isoxazole-3-yl substituted with a substituent selected from methyl, ethyl, isopropyl, and cyclopropylmethyl.

In certain embodiments L is C=O, Z is absent, and R$^5$ is isoxazol-3-yl substituted with a 4- to 6-membered nitrogen-containing C$_{1-6}$heterocycloalkyl. In certain such embodiments, R$^5$ is isoxazol-3-yl substituted with azetidinylmethyl, preferably azetidin-1-ylmethyl. In certain alternative such embodiments, L is C=O, Z is absent, and R$^5$ is isoxazol-3-yl substituted with

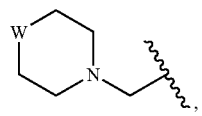

wherein W is O, NR, or CH$_2$, and R is H or C$_{1-6}$alkyl. In certain such embodiments, W is O.

In certain embodiments, L is C=O, Z is absent, and R$^5$ is isoxazol-3-yl substituted with 5-membered nitrogen-containing C$_{1-6}$heteroaralkyl, such as pyrazolylmethyl, imidazolylmethyl, triazol-5-ylmethyl, preferably 1,2,4-triazol-5-ylmethyl.

In certain embodiments, L is C=O, Z is absent, and R$^5$ is isoxazol-3-yl substituted with C$_{1-6}$alkoxy or C$_{1-6}$alkoxyalkyl, preferably methoxy, ethoxy, methoxymethyl, or methoxyethyl.

In certain embodiments, L is C=O, Z is absent, and R$^5$ is isoxazol-3-yl substituted with C$_{1-6}$hydroxyalkyl, preferably hydroxymethyl or hydroxyethyl.

In certain embodiments, L is C=O, Z is absent, and R$^5$ is isoxazol-3-yl substituted with a carboxylic acid, aminocarboxylate, C$_{1-6}$alkylaminocarboxylate, (C$_{1-6}$alkyl)$_2$aminocarboxylate, or C$_{1-6}$alkylcarboxylate. In certain such embodiments, R$^5$ is substituted with methyl carboxylate or ethyl carboxylate, preferably methyl carboxylate.

In certain embodiments, L is C=O, Z is absent, and R$^5$ is an unsubstituted isoxazol-5-yl.

In certain embodiments, L is C=O, Z is absent, and R$^5$ is a substituted isoxazol-5-yl.

In certain such embodiments, R$^5$ is isoxazol-5-yl substituted with a substituent selected from C$_{1-6}$alkyl, C$_{1-6}$alkoxy, C$_{1-6}$alkoxyalkyl, C$_{1-6}$hydroxyalkyl, carboxylic acid, aminocarboxylate, C$_{1-6}$alkylaminocarboxylate, (C$_{1-6}$alkyl)$_2$aminocarboxylate, C$_{1-6}$alkylcarboxylate, C$_{1-6}$heteroaralkyl, C$_{1-6}$aralkyl, C$_{1-6}$heterocycloalkyl, and C$_{1-6}$carbocycloalkyl In certain preferred such embodiments R$^5$ is isoxazole-3-yl substituted with a substituent selected from methyl, ethyl, isopropyl, and cyclopropylmethyl.

In certain embodiments L is C=O, Z is absent, and R$^5$ is isoxazol-3-yl substituted with a 4- to 6-membered nitrogen-containing C$_{1-6}$heterocycloalkyl. In certain such embodiments, R$^5$ is isoxazol-5-yl substituted with azetidinylmethyl, preferably azetidin-1-ylmethyl. In certain alternative such embodiments, L is C=O, Z is absent, and R$^5$ is isoxazol-3-yl substituted with

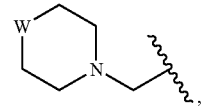

wherein W is O, NR, or CH$_2$, and R is H or C$_{1-6}$alkyl. In certain such embodiments, W is O.

In certain embodiments, L is C=O, Z is absent, and R$^5$ is isoxazol-5-yl substituted with 5-membered nitrogen-containing C$_{1-6}$heteroaralkyl, such as pyrazolylmethyl, imidazolylmethyl, triazol-5-ylmethyl, preferably 1,2,4-triazol-5-ylmethyl.

In certain embodiments, L is C=O, Z is absent, and R$^5$ is isoxazol-5-yl substituted with C$_{1-6}$alkoxy or C$_{1-6}$alkoxyalkyl, preferably methoxy, ethoxy, methoxymethyl, or methoxyethyl.

In certain embodiments, L is C=O, Z is absent, and R$^5$ is isoxazol-5-yl substituted with C$_{1-6}$hydroxyalkyl, preferably hydroxymethyl or hydroxyethyl.

In certain embodiments, L is C=O, Z is absent, and R$^5$ is isoxazol-3-yl substituted with a carboxylic acid, aminocarboxylate, C$_{1-6}$alkylaminocarboxylate, (C$_{1-6}$alkyl)$_2$aminocarboxylate, or C$_{1-6}$alkylcarboxylate. In certain such embodiments, R$^5$ is substituted with methyl carboxylate or ethyl carboxylate, preferably methyl carboxylate.

In certain embodiments, a compound of formula I is selected from

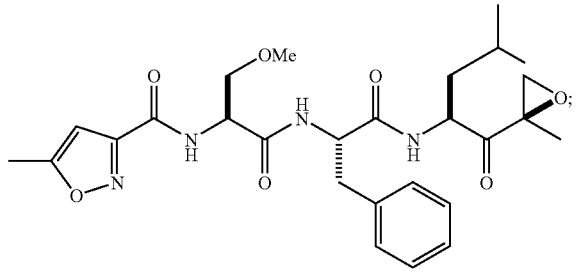

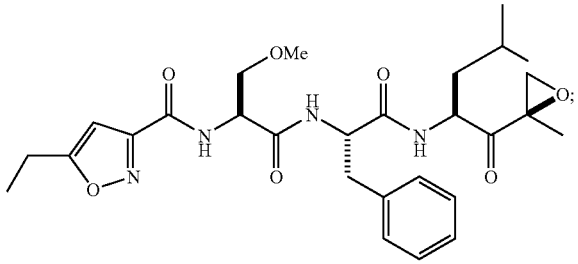

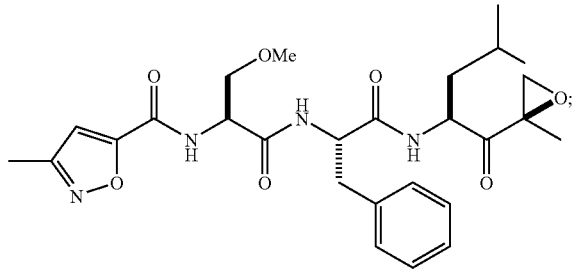

-continued
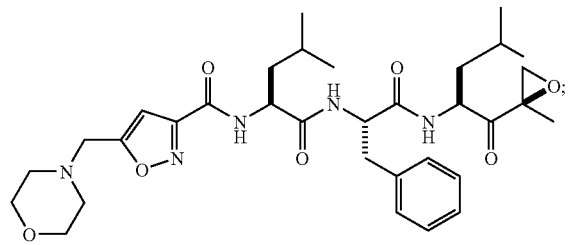
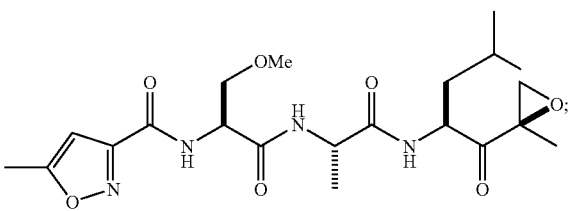
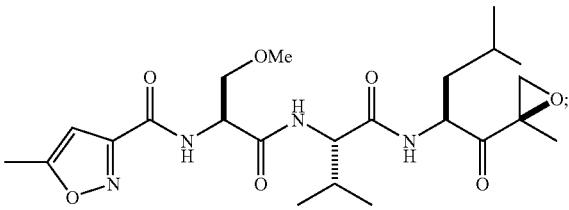
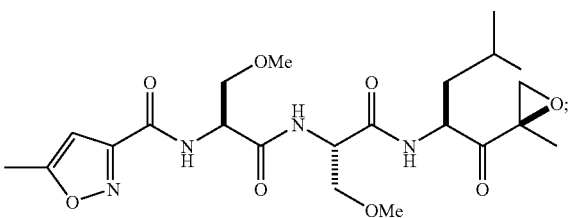
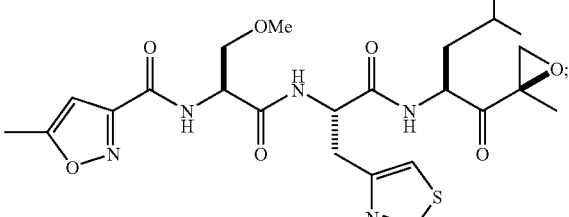
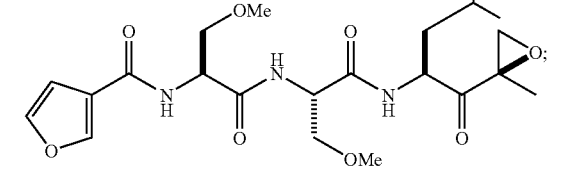
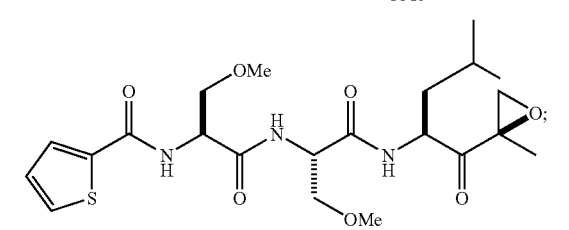

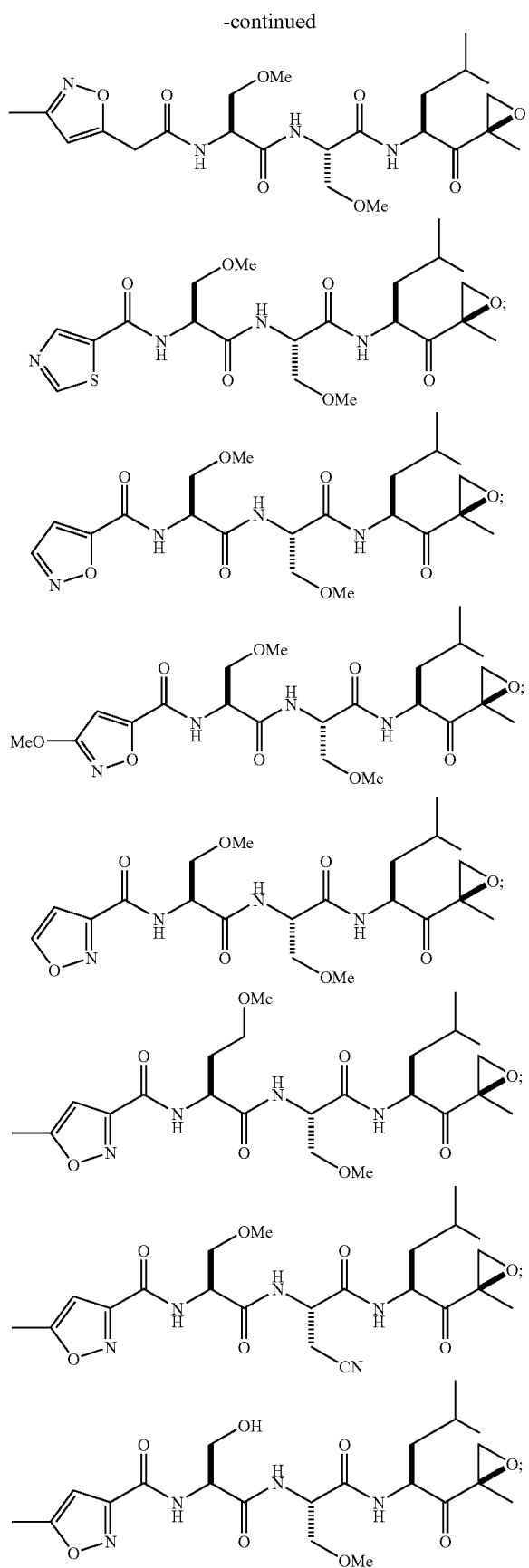
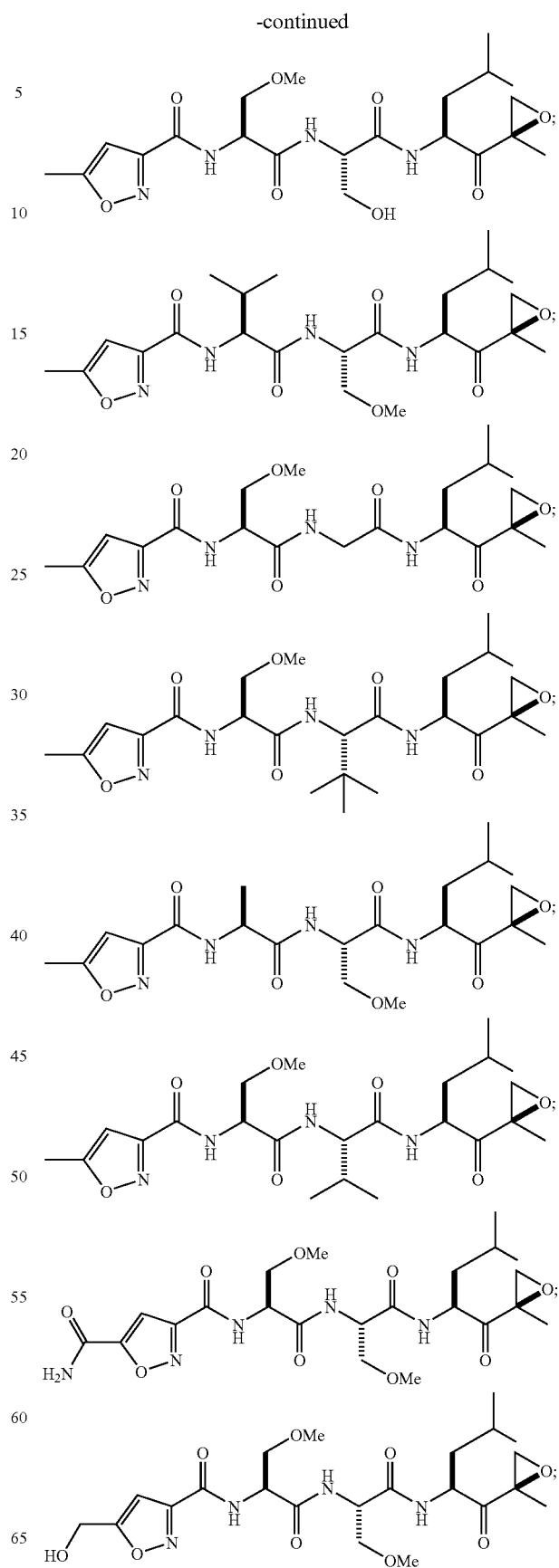

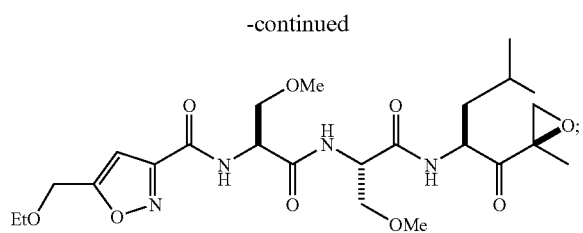
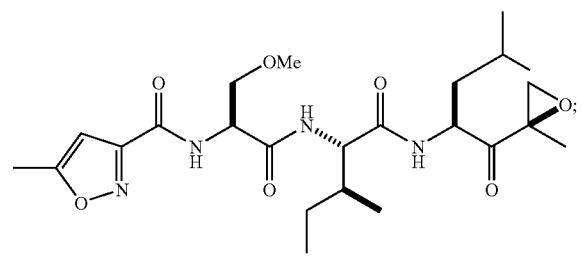
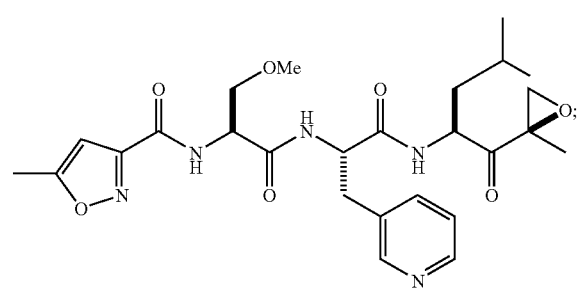
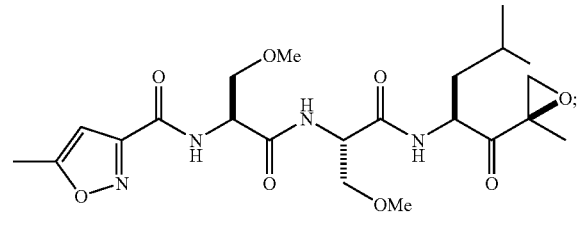
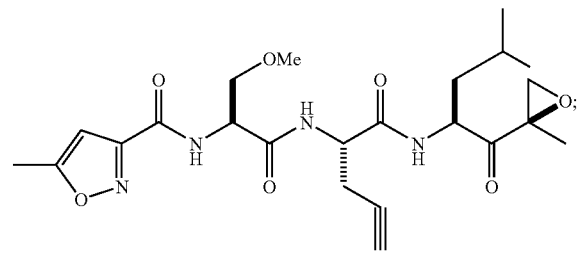
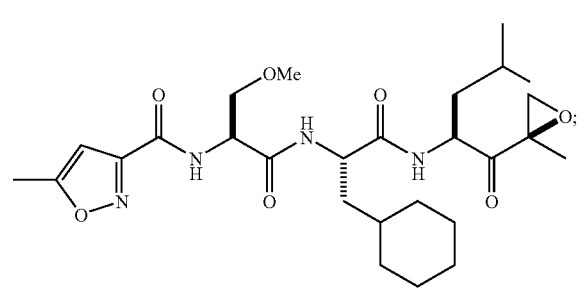
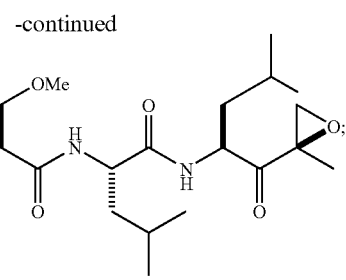
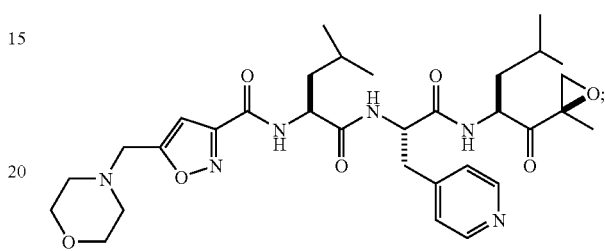
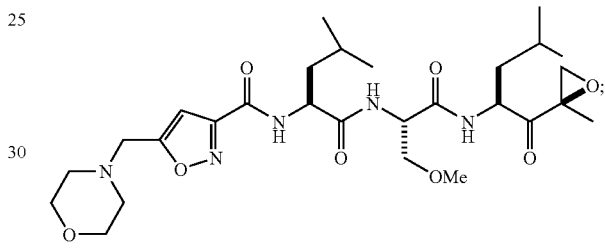
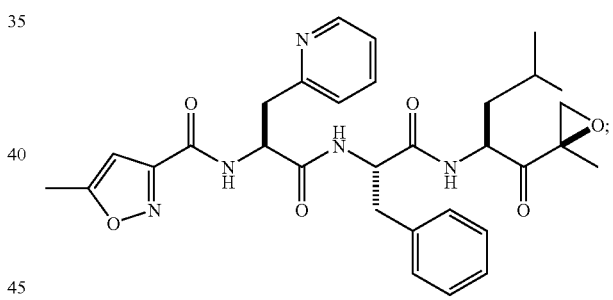
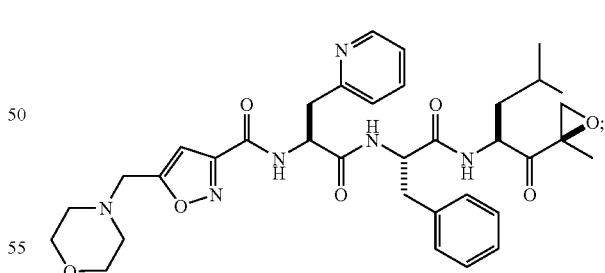
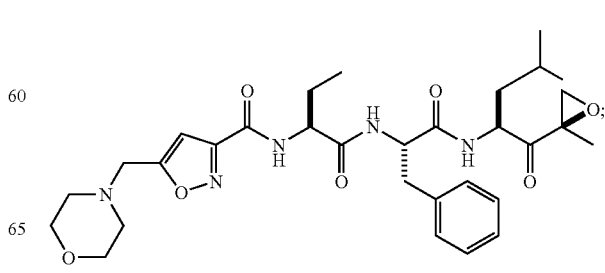

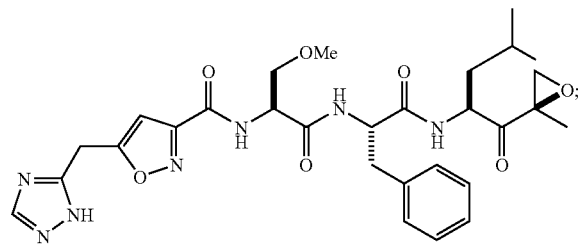
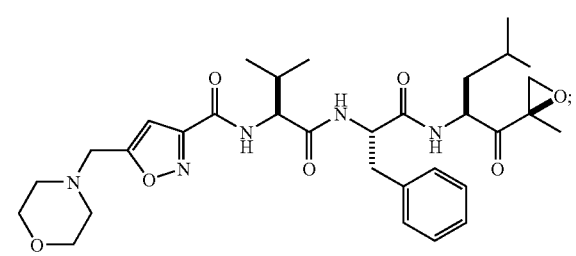
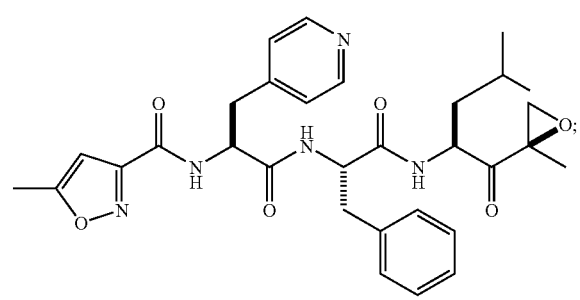
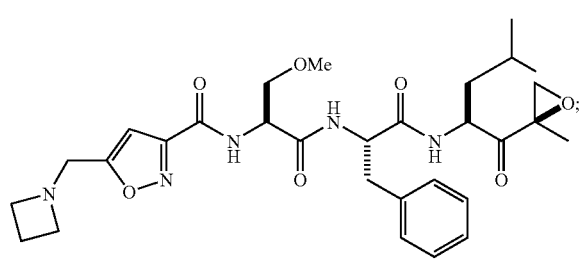
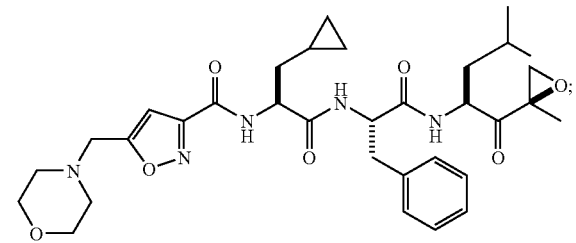
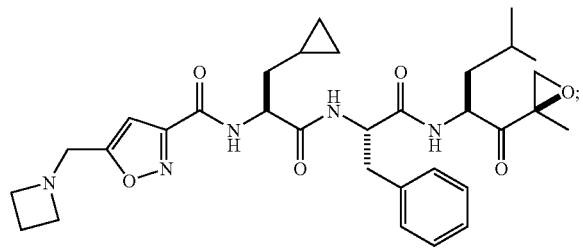
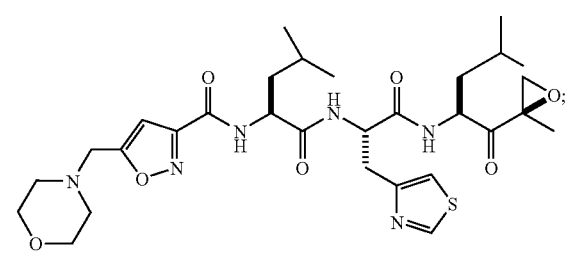
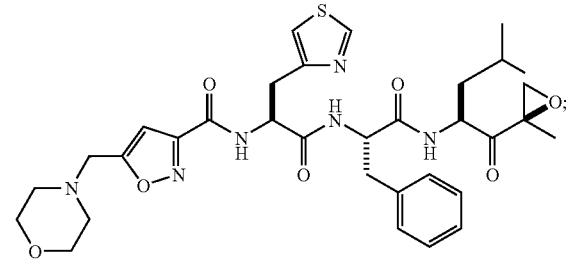
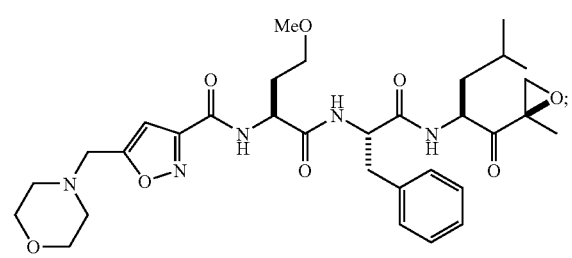
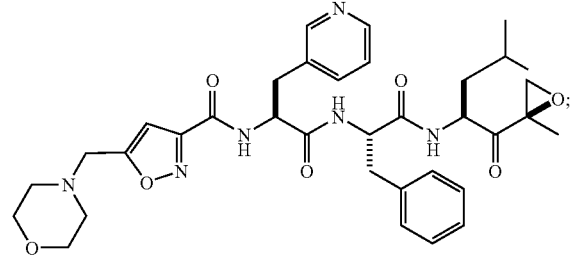
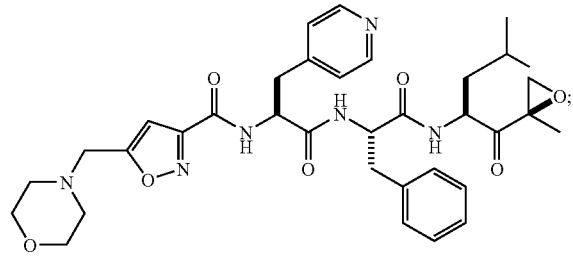
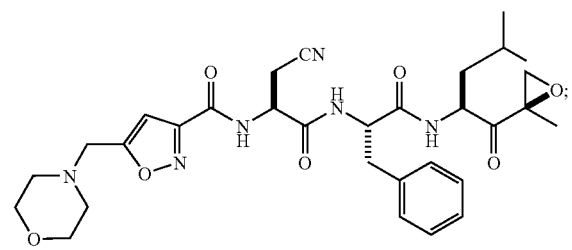

-continued
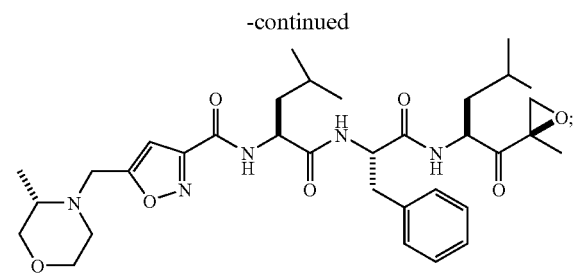
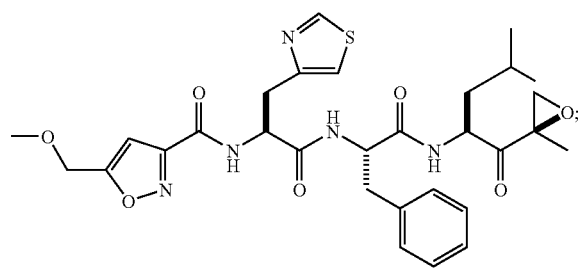
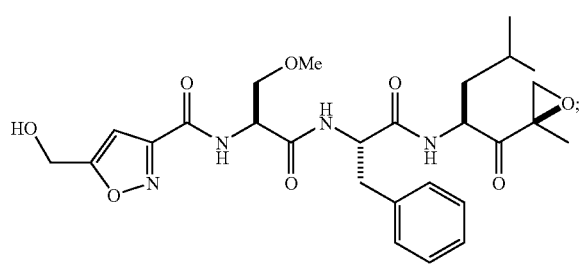
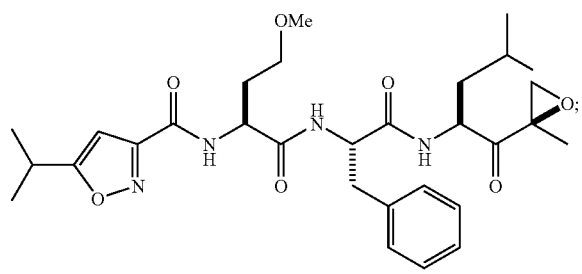
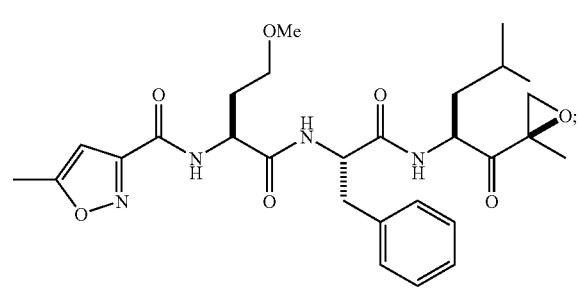
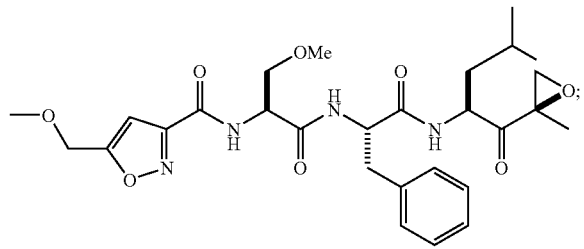
-continued
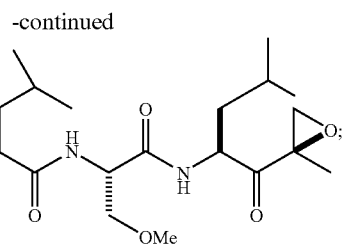
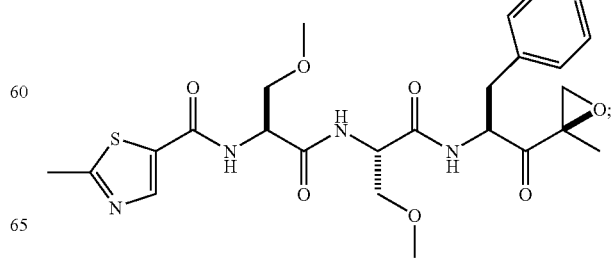

-continued
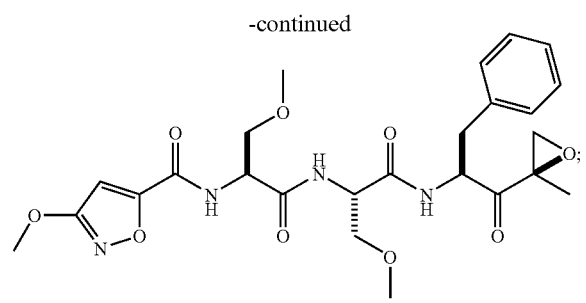
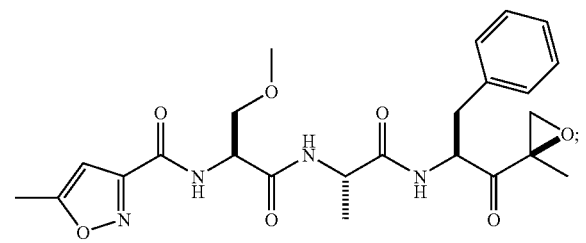
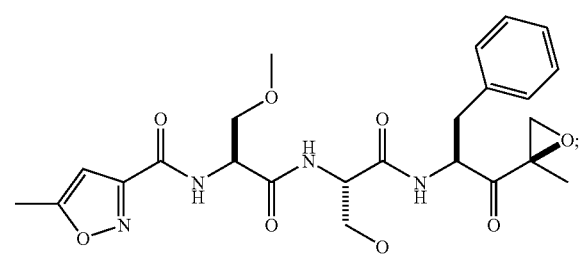
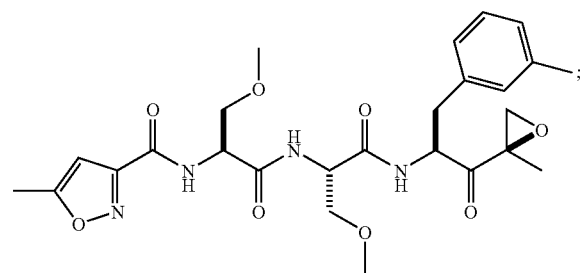
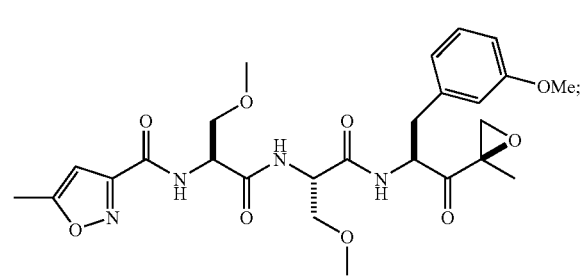
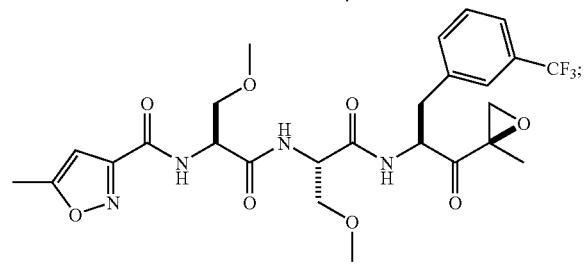
-continued
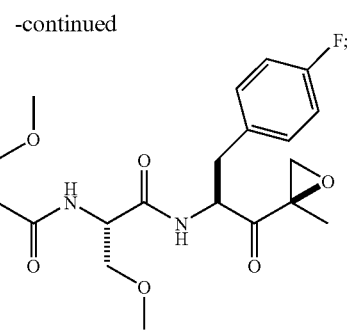
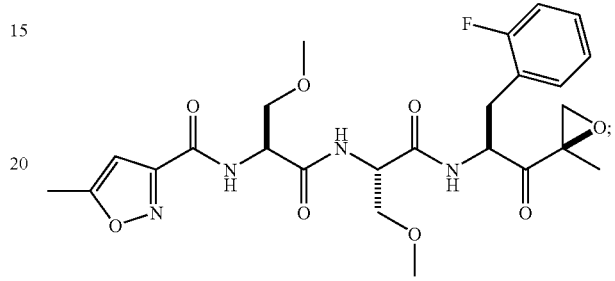
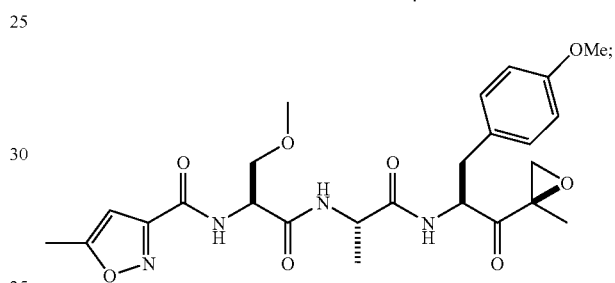
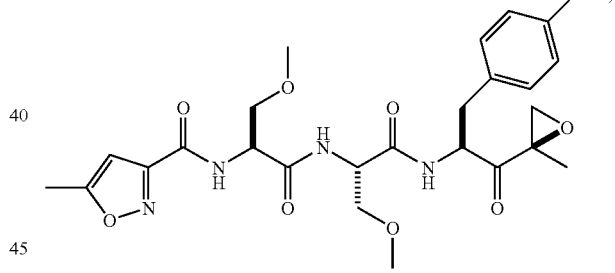
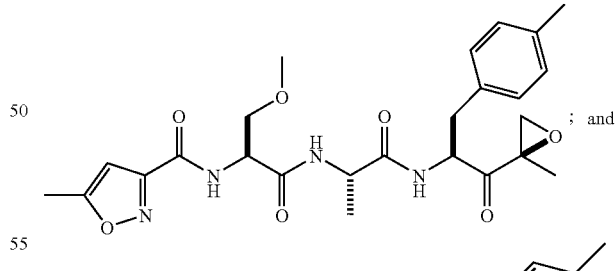
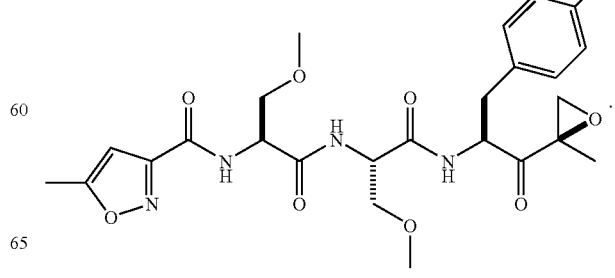

One aspect of the invention relates to a medical device including composition disclosed herein that include an inhibitor having a structure of formula I. In one embodiment, the composition is incorporated within a medical device. In certain embodiments, the medical device is a gel comprising a polymer matrix or ceramic matrix and an inhibitor. Said polymer can be either naturally occurring or synthetic. In another embodiment, said gel serves as a drug depot, an adhesive, a suture, a barrier or a sealant.

Another aspect of the invention relates to a medical device comprising a substrate having a surface onto which an inhibitor having a structure of formula I is disposed. In one embodiment, the inhibitor is directly disposed on a medical device. In another embodiment, a coating is so disposed, the coating comprising a polymer matrix or ceramic matrix with an inhibitor having a structure of formula I dispersed or dissolved therein.

In one embodiment, the medical device is a coronary, vascular, peripheral, or biliary stent. More particularly, the stent of the present invention is an expandable stent. When coated with a matrix containing an inhibitor having a structure formula I, the matrix is flexible to accommodate compressed and expanded states of such an expandable stent. In another embodiment of this invention, the stent has at least a portion which is insertable or implantable into the body of a patient, wherein the portion has a surface which is adapted for exposure to body tissue and wherein at least a part of the surface is coated with an inhibitor having a structure of formula I, or a coating comprising a matrix having an inhibitor having a structure of formula I is dispersed or dissolved therein. An example of a suitable stent is disclosed in U.S. Pat. No. 4,733,665, which is incorporated herein by reference in its entirety.

In another embodiment, the medical device of the present invention is a surgical implement such as a vascular implant, an intraluminal device, surgical sealant or a vascular support. More particularly, the medical device of the present invention is a catheter, an implantable vascular access port, a central venous catheter, an arterial catheter, a vascular graft, an intraaortic balloon pump, a suture, a ventricular assist pump, a drug-eluting barrier, an adhesive, a vascular wrap, an extra/perivascular support, a blood filter, or a filter adapted for deployment in a blood vessel, coated with an inhibitor having a structure of formula I either directly or by a matrix containing an inhibitor having a structure of formula I.

In certain embodiments, the intraluminal medical device is coated with an inhibitor having a structure of formula I or a coating comprising biologically tolerated matrix and an inhibitor having a structure of formula I dispersed in the polymer, said device having an interior surface and an exterior surface, having the coating applied to at least a part of the interior surface, the exterior surface, or both.

In certain embodiments, the medical device may be useful to prevent restenosis after angioplasty. The medical device may also be useful for the treatment of various diseases and conditions by providing localized administration of an inhibitor having a structure of formula I. Such diseases and conditions include restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation. Examples of diseases and conditions that are subject to a treatment including the drug coated medical devices of the present invention include atherosclerosis, acute coronary syndrome, Alzheimer's disease, cancer, fever, muscle disuse (atrophy), denervation, vascular occlusions, stroke, HIV infection, nerve injury, renal failure associated with acidosis, and hepatic failure. See, e.g., Goldberg, U.S. Pat. No. 5,340, 736.

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

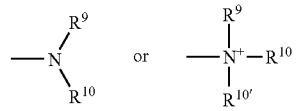

wherein $R^9$, $R^{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, the amino group is basic, meaning the protonated form has a $pK_a \geq 7.00$.

The terms "amide" and "amido" are art-recognized as an amino-substituted carbonyl and includes a moiety that can be represented by the general formula:

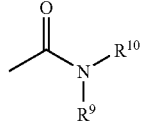

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

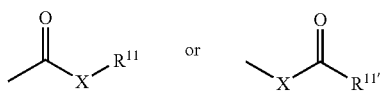

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R^{11'}$ represents a hydrogen, an alkyl, an alkenyl or —$(CH_2)_m$—$R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "$C_{1-6}$heteroaralkyl", as used herein, refers to a $C_{1-6}$alkyl group substituted with a heteroaryl group.

The terms "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, isoxazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The terms "heterocyclyl" or "heterocyclic group" refer to substituted or unsubstituted non-aromatic 3- to 10-membered ring structures, more preferably 3- to 7-membered rings, whose ring structures include one to four heteroatoms. The term terms "heterocyclyl" or "heterocyclic group" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, tetrahydrofuran, piperidine, piperazine, pyrrolidine, morpholine, lactones, lactams, and the like.

The term "$C_{1-6}$heterocycloalkyl", as used herein, refers to a $C_{1-6}$alkyl group substituted with a heterocyclyl group.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "orally bioavailable" is meant to describe a compound administered to a mouse at 40 mg/kg or less, 20 mg/kg or less, or even 10 mg/kg or less, wherein one hour after oral administration such a compound shows at least about 50%, at least about 75% or even at least about 90% inhibition of proteasome CT-L activity in the blood.

As used herein, the term "peptide" includes not only standard amide linkage with standard α-substituents, but commonly utilized peptidomimetics, other modified linkages, non-naturally occurring side chains, and side chain modifications, as detailed below.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S-alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Selectivity for 20S Proteasome

The enzyme inhibitors disclosed herein are useful in part because they inhibit the action of the 20S proteasome. Additionally, unlike other 20S proteasome inhibitors, the compounds disclosed herein are highly selective toward the 20S proteasome, with respect to other protease enzymes. That is, the instant compounds show selectivities for the 20S proteasome over other proteases such as cathepsins, calpains, papain, chymotrypsin, trypsin, tripeptidyl pepsidase II. The selectivities of the enzyme inhibitors for 20S proteasome are such that at concentrations below about 50 μM, the enzyme inhibitors show inhibition of the catalytic activity of the 20S proteasome, while not showing inhibition of the catalytic activity of other proteases such as cathepsins, calpains, papain, chymotrypsin, trypsin, tripeptidyl pepsidase II. In preferred embodiments, the enzyme inhibitors show inhibition of the catalytic activity of the 20S proteasome at concentrations below about 10 μM, while not showing inhibition of the catalytic activity of other proteases at these concentrations. In even more preferred embodiments, the enzyme inhibitors show inhibition of the catalytic activity of the 20S proteasome at concentrations below about 1 μM, while not showing inhibition of the catalytic activity of other proteases at these concentrations. Enzyme kinetic assays are disclosed in U.S. application Ser. No. 09/569,748, Example 2 and Stein et al., *Biochem.* (1996), 35, 3899-3908.

Selectivity for Chymotrypsin-Like Activity

Particular embodiments of the enzyme inhibiting compounds described herein are further useful because they can efficiently and selectively inhibit the chymotrypsin-like activity of the 20S proteasome, as compared to the trypsin-like, and PGPH activities. The chymotrypsin-like activity of 20S proteasome is characterized by cleavage of peptides in the immediate vicinity of large hydrophobic residues. In particular, the chymotrypsin-like activity of Ntn hydrolases can be determined by cleavage of a standard substrate. Examples of such substrates are known in the art. For example, a leucylvalinyltyrosine derivative can be used. Enzyme kinetic assays are disclosed in U.S. application Ser. No. 09/569,748, Example 2 and Stein et al., *Biochem.* (1996), 35, 3899-3908.

Uses of Enzyme Inhibitors

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, immune-related diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, proteasome inhibitor compositions, such as the orally bioavailable peptide epoxy ketone class of molecules as described herein, provide a means of treating patients with these conditions.

Proteasome inhibitor compositions may be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

At the cellular level, the accumulation of polyubiquitinated proteins, cell morphological changes, and apoptosis have been reported upon treatment of cells with various proteasome inhibitors. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. One aspect of the invention relates to the treatment of cachexia and muscle-wasting diseases. Compounds of the invention may be useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736. Certain embodiments of the invention therefore encompass compositions for: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a pharmaceutical composition comprising a proteasome inhibitor disclosed herein.

Intracellular proteolysis generates small peptides for presentation to T-lymphocytes to induce MHC class I-mediated immune responses. The immune system screens for autologous cells that are virally infected or have undergone oncogenic transformation. In certain embodiments, the invention relates to a method for inhibiting antigen presentation in a cell, comprising exposing the cell to a compound described herein. Proteasome inhibitors of the invention may be used to treat immune-related conditions such as allergy, asthma, organ/tissue rejection (graft-versus-host disease), and autoimmune diseases, including, but not limited to, lupus, rheumatoid arthritis, psoriasis, multiple sclerosis, and inflammatory bowel diseases (such as ulcerative colitis and Crohn's disease). Thus, in certain embodiments, the invention relates to a method for suppressing the immune system of a subject comprising administering to the subject an effective amount of a proteasome inhibitor compound described herein.

In certain embodiments, the invention relates to a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Another aspect of the invention relates to the use of proteasome inhibitor compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the subunit of human macropain (Kojima, S. et al., *Fed. Eur. Biochem. Soc.*, (1992) 304:57-60). The APP-processing enzyme cleaves at the $Gln^{15}$-$Lys^{16}$ bond; in the presence of calcium ion, the enzyme also cleaves at the $Met^{-1}$-$Asp^1$ bond, and the $Asp^1$-$Ala^2$ bonds to release the extracellular domain of β-AP.

One aspect of the invention, therefore, relates to a method of treating Alzheimer's disease, comprising administering to a subject an effective amount of a proteasome inhibitor composition disclosed herein. Such treatment includes reducing the rate of β-AP processing, reducing the rate of β-AP plaque formation, reducing the rate of β-AP generation, and reducing the clinical signs of Alzheimer's disease.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity (Xu et al., 2000). However, accelerated degradation of the TGF-β signaling components has been observed in cancers and other hyperproliferative conditions. Thus, in certain embodiments the invention relates to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of bum victims is often hampered by fibrosis, thus, in certain embodiments, the invention relates to the topical or systemic administration of the inhibitors to treat bums. Wound closure following surgery is often associated with disfiguring scars, which may be prevented by inhibition of fibrosis. Thus, in certain embodiments, the invention relates to a method for the prevention or reduction of scarring.

Certain proteasome inhibitors block both degradation and processing of ubiquitinated NF-κB in vitro and in vivo. Proteasome inhibitors also block IκB-A degradation and NF-κB activation (Palombella, et al. *Cell* (1994) 78:773-785; and Traenckner, et al., *EMBO J.* (1994) 13:5433-5441). One aspect of the invention relates to a method for inhibiting IκB-α degradation, comprising contacting the cell with a compound described herein. In certain embodiments, the invention relates to a method for reducing the cellular content of NF-κB in a cell, muscle, organ, or subject, comprising contacting the cell, muscle, organ, or subject with a proteasome inhibitor compound described herein.

NF-κB is a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., *Cell* (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). In certain embodiments, the invention relates to methods of affecting the level of expression of IL-2, MHC-I, IL-6, TNFα, IFN-β or any of the other previously-mentioned proteins, each method comprising administering to a subject an effective amount of a proteasome inhibitor composition disclosed herein. Complexes including p50 are rapid mediators of acute inflammatory and immune responses (Thanos, D. and Maniatis, T., *Cell* (1995) 80:529-532).

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, the proteasome inhibitor compositions may be used for the inhibition of TNFα to prevent and/or treat septic shock.

NF-κB also participates in the expression of the cell adhesion genes that encode E-selectin, P-selectin, ICAM, and VCAM-1 (Collins, T., *Lab. Invest.* (1993) 68:499-508). In certain embodiments the invention relates to a method for inhibiting cell adhesion (e.g., cell adhesion mediated by E-selectin, P-selectin, ICAM, or VCAM-1), comprising contacting a cell with (or administering to a subject) an effective amount of a pharmaceutical composition comprising a proteasome inhibitor disclosed herein.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, J., *Science,* (1995) 267:960). In certain embodiments, the invention relates to a method for inhibiting or reducing HIV infection in a subject, or a method for decreasing the level of viral gene expression, each method comprising administering to the subject an effective amount of a proteasome inhibitor composition disclosed herein.

Viral infections contribute to the pathology of many diseases. Heart conditions such as ongoing myocarditis and dilated cardiomyopathy have been linked to the coxsackievirus B3. In a comparative whole-genome microarray analyses of infected mouse hearts, specific proteasome subunits were uniformly up-regulated in hearts of mice which developed chronic myocarditis (Szalay et al, Am J Pathol 168:1542-52, 2006). Some viruses utilize the ubiquitin-proteasome system in the viral entry step where the virus is released from the endosome into the cytosol. The mouse hepatitis virus (MHV) belongs to the Coronaviridae family, which also includes the severe acute respiratory syndrome (SARS) coronvirus. Yu and Lai (J Virol 79:644-648, 2005) demonstrated that treatment of cells infected with MHV with a proteasome inhibitor resulted in a decrease in viral replication, correlating with reduced viral titer as compared to that of untreated cells. The human hepatitis B virus (HBV), a member of the Hepadnaviridae virus family, likewise requires virally encoded envelop proteins to propagate. Inhibiting the proteasome degradation pathway causes a significant reduction in the amount of secreted envelope proteins (Simsek et al, J Virol 79:12914-12920, 2005). In addition to HBV, other hepatitis viruses (A, C, D and E) may also utilize the ubiquitin-proteasome degradation pathway for secretion, morphogenesis and pathogenesis. Accordingly, in certain embodiments, the invention relates to a method for treating viral infection, such as SARS or hepatitis A, B, C, D and E, comprising contacting a cell with (or administering to a subject) an effective amount of a compound disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of a proteasome inhibitor compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

In certain embodiments, the invention relates to methods for affecting cyclin-dependent eukaryotic cell cycles, comprising exposing a cell (in vitro or in vivo) to a proteasome inhibitor composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with p34$^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., Cell, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). One aspect of the invention relates to a method for treating a proliferative disease in a subject (e.g., cancer, psoriasis, or restenosis), comprising administering to the subject an effective amount of a proteasome inhibitor composition disclosed herein. The invention also relates to a method for treating cyclin-related inflammation in a subject, comprising adminstering to a subject a therapeutically effective amount of a proteasome inhibitor composition described herein.

Additional embodiments of the invention relate to methods for affecting the proteasome-dependent regulation of oncoproteins and methods of treating or inhibiting cancer growth, each method comprising exposing a cell (in vivo, e.g., in a subject, or in vitro), to a proteasome inhibitor composition disclosed herein. HPV-16 and HPV-18-derived E6 proteins stimulate ATP-and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. In certain embodiments, the invention relates to a method for treating p53-related apoptosis, comprising administering to a subject an effective amount of a proteasome inhibitor composition disclosed herein.

In certain embodiments, the disclosed compositions may be useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, entamoeba species have been shown to lose encystation capacity when exposed to proteasome inhibitors (Gonzales, et al., Arch. Med. Res. 1997, 28, Spec No: 139-140). In certain such embodiments, the administrative protocols for the proteasome inhibitor compositions are useful for the treatment of parasitic infections in humans caused by a protozoan parasite selected from *Plasmodium* sps. (including *P. falciparum, P. vivax, P. malariae,* and *P. ovale,* which cause malaria), *Trypanosoma* sps. (including *T. cruzi,* which causes Chagas' disease, and *T. brucei* which causes African sleeping sickness), *Leishmania* sps. (including *L. amazonesis, L. donovani, L. infantum, L. mexicana,* etc.), *Pneumocystis carinii* (a protozoan known to cause pneumonia in AIDS and other immunosuppressed patients), *Toxoplasma gondii, Entamoeba histolytica, Entamoeba invadens,* and *Giardia lamblia.* In certain embodiments, the disclosed proteasome inhibitor compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona,* and *Neurospora crassa.* Other compounds useful as proteasome inhibitors in the treatment of parasitic diseases are described in WO 98/10779, which is incorporated herein in its entirety.

In certain embodiments, the proteasome inhibitor compositions inhibit proteasome activity in a parasite without recovery in red blood cells and white blood cells. In certain such embodiments, the long half-life of blood cells may provide prolonged protection with regard to therapy against recurring exposures to parasites. In certain embodiments, the proteasome inhibitor compositions may provide prolonged protection with regard to chemoprophylaxis against future infection.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed proteasome inhibitor compositions may be useful in the treatment and/or prevention of diseases associated with bone loss, such as osteoporosis.

Proteasome inhibition has already been validated as a therapeutic strategy for the treatment of cancer, particularly multiple myeloma. However, based on both in vitro and in vivo models, one would predict that it could serve as a strategy against other cancers, particularly heme-related malignancies and solid tumors. Therefore, certain embodiments of the invention relate to a method of treating cancers comprising administering to a subject in need of such treatment an effective amount of a proteasome inhibitor compound disclosed herein.

Administration

Compounds prepared as described herein can be administered in various forms, depending on the disorder to be treated and the age, condition, and body weight of the patient, as is well known in the art. For example, where the compounds are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means, and if desired, the active ingredient may be mixed with any conventional additive or excipient, such as a binder, a disintegrating agent, a lubricant, a corrigent, a solubilizing agent, a suspension aid, an emulsifying agent, a coating agent, a cyclodextrin, and/or a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", J. Pharm. Sci. 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in microencapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of theses substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, oleic acid, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

Another aspect of the invention provides a conjoint therapy wherein one or more other therapeutic agents are administered with the proteasome inhibitor. Such conjoint treatment may be achieved by way of the simultaneous, sequential, or separate dosing of the individual components of the treatment.

In certain embodiments, a compound of the invention is conjointly administered with one or more other proteasome inhibitor(s).

In certain embodiments, a compound of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); anti-platelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates (busulfan), nitrosoureas (carmustine (BCNU) and analogs, streptozocin), trazenes—dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; histone deacetylase (HDAC) inhibitors; hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a compound of the invention is conjointly administered with a cytokine. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In certain embodiments, a compound of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, pred-

EXEMPLIFICATION

Example 1

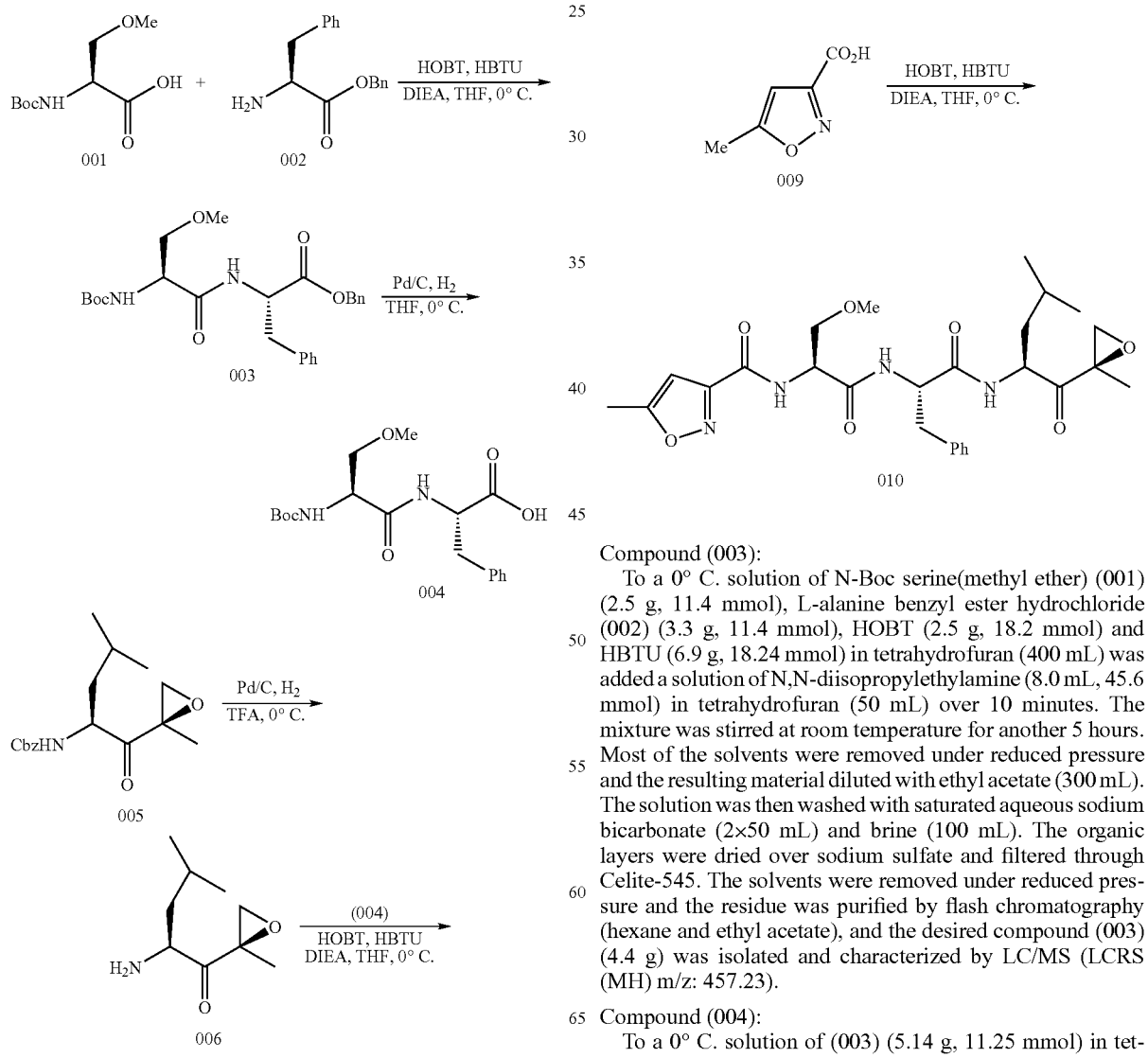

Compound (003):

To a 0° C. solution of N-Boc serine(methyl ether) (001) (2.5 g, 11.4 mmol), L-alanine benzyl ester hydrochloride (002) (3.3 g, 11.4 mmol), HOBT (2.5 g, 18.2 mmol) and HBTU (6.9 g, 18.24 mmol) in tetrahydrofuran (400 mL) was added a solution of N,N-diisopropylethylamine (8.0 mL, 45.6 mmol) in tetrahydrofuran (50 mL) over 10 minutes. The mixture was stirred at room temperature for another 5 hours. Most of the solvents were removed under reduced pressure and the resulting material diluted with ethyl acetate (300 mL). The solution was then washed with saturated aqueous sodium bicarbonate (2×50 mL) and brine (100 mL). The organic layers were dried over sodium sulfate and filtered through Celite-545. The solvents were removed under reduced pressure and the residue was purified by flash chromatography (hexane and ethyl acetate), and the desired compound (003) (4.4 g) was isolated and characterized by LC/MS (LCRS (MH) m/z: 457.23).

Compound (004):

To a 0° C. solution of (003) (5.14 g, 11.25 mmol) in tetrahydrofuran (100 mL) was added 10% Pd/C (500 mg). The nylidene, rimexolone, tixocortol, triamcinolone, triamcinolone acetonide, triamcinolone benetonide, triamcinolone hexacetonide, and salts and/or derivatives thereof.

In certain embodiments, a compound of the invention is conjointly administered with an immunotherapeutic agent. Suitable immunotherapeutic agents may include, but are not limited to, MDR modulators (verapamil, valspordar, biricodar, tariquidar, laniquidar), rapamycin, mycophenylate mofetil, cyclophosomide, cyclosporine, thalidomide, and monoclonal antibodies. The monoclonal antibodies can be either naked or conjugated such as rituximab, tositumomab, alemtuzumab, daclizumab, epratuzumab, ibritumomab tiuxetan, gemtuzumab ozogamicin, bevacizumab, cetuximab, erlotinib and trastuzumab.

resulting mixture was allowed to stir under 1 atmosphere of hydrogen for 4 hours. The mixture was filtered through Celite-545 and the filter cake was washed with tetrahydrofuran. The organic filtrate was concentrated under reduced pressure and placed under high vacuum for 2 hours to provide (004) as confirmed by LC/MS (LCRS (MH) m/z: 367.18) which was used without further purification.

Compound (006):

To a solution of (005) (for a synthesis of (005) see U.S. patent application Ser. No. 11/131,688) (3.9 g, 13 mmol) in trifluoroacetic acid (50 mL) was added 10% Pd/C (600 mg). The resulting mixture was allowed to stir under 1 atmosphere of hydrogen for 6 hours. The mixture was filtered through Celite-545 and the filter cake washed with dichloromethane (200 mL). The filtrate was concentrated under reduced pressure and placed under high vacuum overnight to provide (006) as confirmed by LC/MS (LCRS (MH) m/z: 172.13) and was used in the subsequent transformation without further purification.

Compound (007):

To a 0° C. solution of (004) and (006), HOBT (2.5 g, 18 mmol) and HBTU (6.9 g, 18 mmol) in tetrahydrofuran (400 mL) was added a solution of N,N-diethylisopropylamine (8 mL, 46 mmol) in tetrahydrofuran (50 mL) over 10 minutes. The mixture was stirred at room temperature for another 5 hours. Most of the solvents were removed under reduced pressure and the remaining material was diluted with ethyl acetate (400 mL). The resulting solution was washed with saturated aqueous sodium bicarbonate (2×100 mL) and brine (100 mL). The organic layers were dried over sodium sulfate and filtered through Celite-545. The solvents were removed under reduced pressure and the residue was purified by flash chromatography (hexane and ethyl acetate), to provide (007) (3.5 g) as characterized by LC/MS (LCRS (MH) m/z: 520.29).

Compound (008):

To a 0° C. solution of (007) (320 mg, 0.616 mmol) in dichloromethane (10 mL) was added trifluoroacetic acid (10 mL) and the resulting solution was stirred at the same temperature for another hour. The organic layers were concentrated under reduced pressure and then placed under high vacuum for 2 hours to provide (008) as confirmed by LC/MS (LCRS (MH) m/z: 420.24) which was used without further purification.

Compound (010):

To a 0° C. solution of (008), 5-methyl-isoxazole-3-carboxylic acid (009) (94 mg, 0.74 mmol), HOBT (135 mg, 1.0 mmol) and HBTU (350 mg, 1.0 mmol) in tetrahydrofuran (100 mL) was added a solution of N,N-diisopropylethylamine (0.5 mL, 2.5 mmol) in tetrahydrofuran (2 mL) over 5 minutes. The mixture was stirred at room temperature for another 5 hours and then diluted with ethyl acetate (200 mL). It was then washed with saturated aqueous sodium bicarbonate (2×10 mL) and brine (10 mL) and the organic layers were dried over sodium sulfate and filtered through Celite-545. The solvents were removed under reduced pressure and the residue was purified by HPLC (aqueous ammonium acetate and acetonitrile) to provide (010) (195 mg) as characterized by LC/MS (LCRS (MH) m/z: 529.26); >90% proteasome CT-L inhibition at 40 mg/kg PO.

Example 2

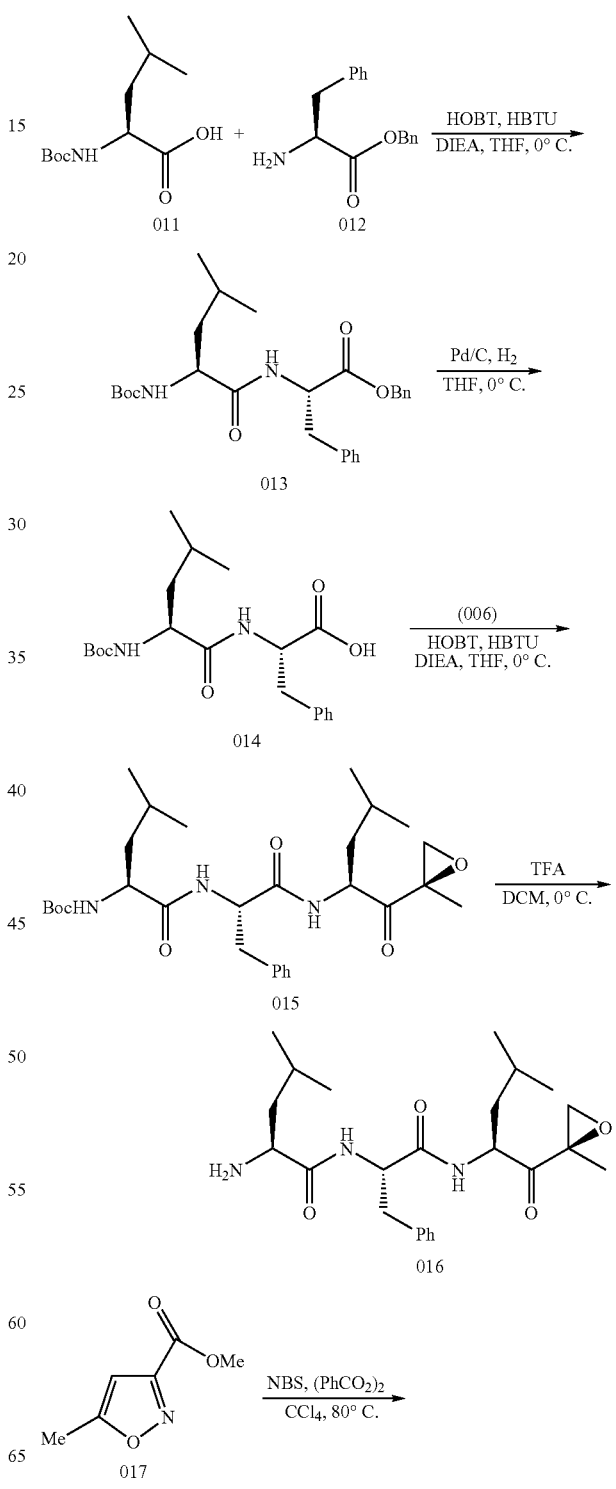

Scheme 2: Synthesis of Example 023

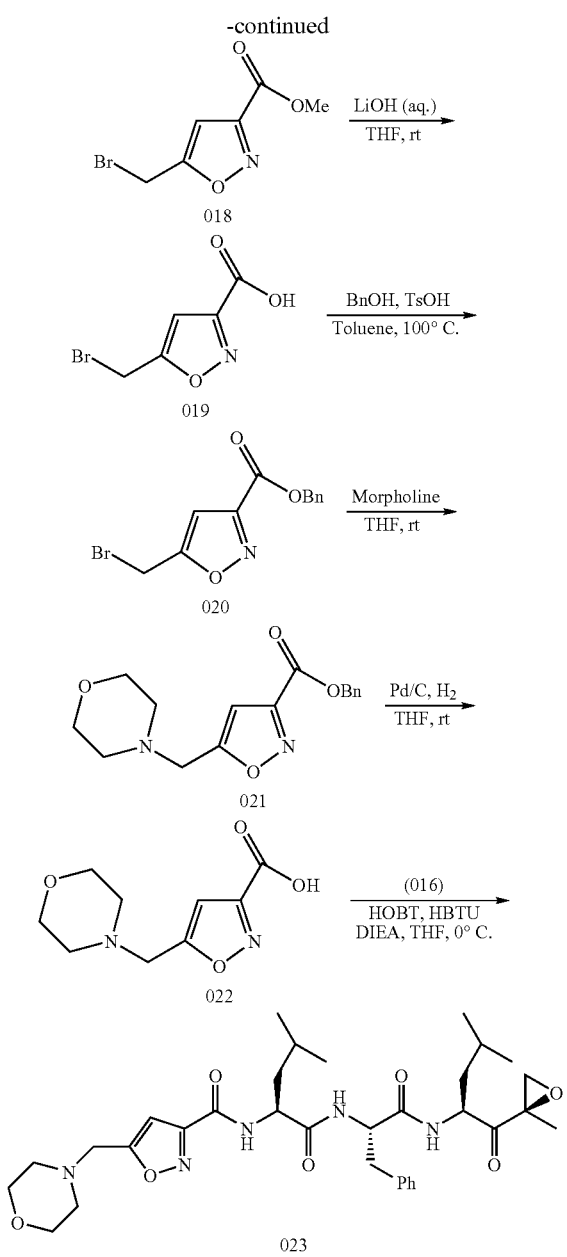

Compound (013):

To a 0° C. solution of N-Boc L-leucine (011) (2.6 g, 11 mmol), L-phenylalanine benzyl ester hydrochloride (012) (2.9 g, 10 mmol), HOBT (1.7 g, 11 mmol) and HBTU (3.9 g, 11 mmol) in tetrahydrofuran (200 mL) was added a solution of N,N-diisopropylethylamine (4.9 mL, 30 mmol) in tetrahydrofuran (10 mL) over 5 minutes. The mixture was stirred at room temperature for another 5 hours and became homogenous. It was then diluted with ethyl acetate (300 mL) and washed with saturated aqueous sodium bicarbonate (2×50 mL) and brine (100 mL). The organic layers were dried over sodium sulfate and filtered through Celite-545. The solvents were removed under reduced pressure and the residue was purified by flash chromatography (hexane and ethyl acetate) to provide (013) (4.4 g) as characterized by LC/MS (LCRS (MH) m/z: 469.26).

Compound (014):

To a 0° C. solution of (013) (4.32 g, 9.24 mmol) in tetrahydrofuran (100 mL) was added 10% Pd/C (500 mg). The resulting mixture was allowed to stir under 1 atmosphere of hydrogen for 4 hours. The mixture was filtered through Celite-545 and the filter cake was washed with tetrahydrofuran. The organic filtrate was concentrated under reduced pressure and placed under high vacuum to provide (014) (3.5 g) as confirmed by LC/MS (LCRS (MH) m/z: 378.22) which was used without further purification.

Compound (015):

To a 0° C. solution of (014) (3.5 g, 9.24 mmol) and (006) (2.4 g, 11 mmol), HOBT (1.7 g, 11 mmol) and HBTU (3.9 g, 11 mmol) in tetrahydrofuran (200 mL) was added a solution of N,N-diisopropylethylamine (4.9 mL, 30 mmol) in tetrahydrofuran (10 mL) over 5 minutes. The mixture was stirred at room temperature for another 5 hours and became homogenous. It was then diluted with ethyl acetate (400 mL), and washed with saturated aqueous sodium bicarbonate (2×100 mL) and brine (100 mL). The organic layers were dried over sodium sulfate and filtered through Celite-545. The solvents were removed under reduced pressure and the residue was purified by flash chromatography (hexane and ethyl acetate), and the desired compound (015) (5.0 g) was isolated and characterized by LC/MS (LCRS (MH) m/z: 532.33).

Compound (016):

To a 0° C. solution of (015) (5.0 g, 9.40 mmol) in dichloromethane (50 mL) was added trifluoroacetic acid (20 mL) over 5 minutes, and the resulting solution was stirred at the same temperature for another hour. The organic layers were concentrated under reduced pressure and placed under high vacuum to provide (016) as confirmed by LC/MS (LCRS (MH) m/z: 432.33) which was used without further purification.

Compound (018):

To a solution of methyl 5-methyl-3-isoxazolecarboxylate (017) (14.1 g, 100 mmol) in carbon tetrachloride (500 mL) was added N-bromosuccunimide (23 g, 130 mmol) and benzoyl peroxide (2.5 g, 10 mmol) at room temperature. The resulting mixture was stirred at 80° C. under an atmosphere of argon overnight. The reaction was the cooled and diluted with 500 mL of dichloromethane and washed with saturated aqueous sodium bicarbonate (3×100 mL). The aqueous phase was extracted with 200 mL of dichloromethane, and the combined organic layers were washed with brine and dried over MgSO$_4$. The solvents were removed and the residue was purified by flash chromatography (hexane and ethyl acetate) to provide (018) (7.9 g) which was characterized by LC/MS (LCRS (MH) m/z: 219.95).

Compound (019):

To a 0° C. solution of (018) (12 g, 55 mmol) in tetrahydrofuran (20 mL) was added aqueous lithium hydroxide (35 mL, 4N). The resulting mixture was stirred at room temperature overnight. It was then acidified with hydrochloric acid (2N) to pH=1 and extracted with tetrahydrofuran (3×200 mL). The combine organic layers were washed with brine (10 mL), dried over sodium sulfate, and filtered. The solvents were removed and the residue was lyophilized to yield (019) (8.2 g), which was confirmed by LC/MS (LCRS (MH) m/z: 205.95) and used without further purification.

Compound (020):

A solution of (019) (6.0 g, 30 mmol), benzyl alcohol (3.5 mL), and p-toluenesulfonyl acid (1.1 g, 6 mmol) in toluene (100 mL) was stirred at 100° C. overnight. It was then allowed to cool, diluted with 300 mL of ethyl acetate and washed with saturated aqueous sodium bicarbonate. The aqueous phase was then extracted with 200 mL of ethyl acetate. The combine organic layers were washed with brine, dried over sodium sulfate, and filtered. The solvents were removed and the residue was purified by flash chromatography (hexane and ethyl acetate), to provide (020) (5.8 g) which was characterized by LC/MS (LCRS (MH) m/z: 295.98).

Compound (021):

A solution of (020) (2.0 g, 6.8 mmol) and morpholine (3.0 mL) in tetrahydrofuran (50 mL) was stirred at room temperature for two hours. The solvents were then removed and the residue was purified by flash chromatography (hexane and ethyl acetate/methanol) to provide (021) (820 mg) which was characterized by LC/MS (LCRS (MH) m/z: 303.13).

Compound (022):

To a solution of (021) (400 mg, 1.32 mmol) in tetrahydrofuran (40 mL) was added 10%Pd/C (100 mg) and the mixture was stirred at room temperature under one atmosphere of hydrogen for 2 hours. It was then filtered through Celite and concentrated to give (022), which was confirmed by LC/MS (LCRS (MH) m/z: 213.08) and was used without further purification.

Compound (023):

To a 0° C. solution of (016) (130 mg, 0.3 mmol) and (022) (70 mg, 0.4 mmol), HOBT (70 mg, 0.5 mmol) and HBTU (170 mg, 0.5 mmol) in tetrahydrofuran (50 mL) was added a solution of N,N-diisopropylethylamine (0.5 mL, 2.5 mmol) in tetrahydrofuran (5 mL). The mixture was stirred at room temperature for another 5 hours and became homogenous. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide compound (023) (125 mg) which was characterized by LCIMS (LCRS (MH) m/z: 626.35); >80% proteasome CT-L inhibition at 40 mg/kg PO.

Example 3

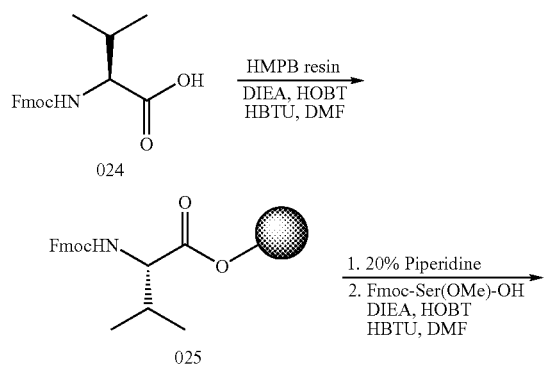

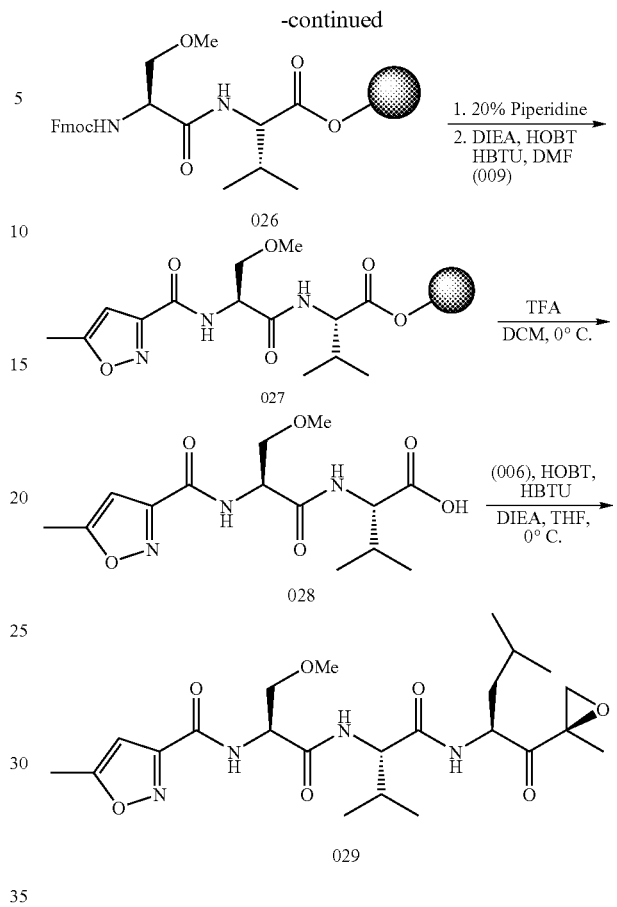

Compound (025):

To a 0° C. solution of Fmoc-Val-OH (024) (348 mg, 1.6 mmol) in dichloromethane (4 mL) were added MSNT (474 mg, 1.6 mmol) and N-methyl-imidazole (0.13 mL, 1.6 mmol). HMPB resin (400 mg, 0.32 mmol) was added once the mixture became homogenous. The resulting reaction mixture was allowed to shake for two hours at room temperature. The resin was filtered off, washed with N,N-dimethylformamide (3×10 mL) and dichloromethane (3×10 mL), and was allowed to air dry to yield (025).

Compound (026):

Resin (025) was placed in a solution of 20% piperidine in N,N-dimethylformamide (20 ml) and the resulting mixture was shaken at room temperature for 1 hour. The resin was filtered off and washed with N,N-dimethylformamide (3×10 mL) and dichloromethane (3×10 mL).

To a 0° C. solution of Fmoc-Ser(OMe)-OH (546 mg, 1.6 mmol) in N,N-dimethylformamide (4 mL) were added HOBT (245 mg, 1.6 mmol), HBTU (606 mg, 1.6 mmol,) and N,N-diisopropylethylamine (0.6 mL, 3.2 mmol). The resin was added once the reaction mixture became homogenous. The resulting mixture was allowed to shake overnight. The resin was then filtered off and washed with N,N-dimethylformamide (3×10 mL) and dichloromethane (3×10 mL), and allowed to air dry to yield (026).

Compound (027):

Resin (026) was placed in a solution of 20% piperidine in N,N-dimethylformamide (20 mL) and the resulting mixture was shaken at room temperature for 1 hour. The resin was filtered off and washed with N,N-dimethylformamide (3×10 mL) and dichloromethane (3×10 mL).

To a 0° C. solution of 5-methyl-isoxazole-3-carboxylic acid (009) (162 mg, 1.6 mmol) in N,N-dimethylformamide (4 mL) were added HOBT (245 mg, 1.6 mmol), HBTU (606 mg, 1.6 mmol) and N,N-diisopropylethylamine (0.6 mL, 3.2 mmol). Once the resulting mixture became homogenous, the resin was added and the resulting reaction mixture was allowed to shake overnight. The resin was then filtered off and washed with N,N-dimethylformamide (3×10 mL) and dichloromethane (3×10 mL), and the resin was allowed to air dry to yield (027).

Compound (028):

To resin (027) was added a solution of 50% trifluoroacetic acid in dichloromethane (10 mL), and the resulting mixture was allowed to shake for 30 minutes. The resin was then filtered off and washed with dichloromethane (3×10 mL). The volatiles were removed under reduced pressure to provide (028) which was characterized by LC/MS (LCRS (MH) m/z: 328.14) and used without further purification.

Compound (029):

To a 0° C. solution of (029) and (006) (117 mg, 0.4 mmol), HOBT (70 mg, 0.5 mmol) and HBTU (170 mg, 0.5 mmol) in tetrahydrofuran (50 mL) was added a solution of N,N-diisopropylethylamine (0.5 mL, 2.5 mmol) in tetrahydrofuran (5 mL). The mixture was stirred at room temperature for another 5 hours and became homogenous. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (029) (125 mg) which was characterized by LC/MS (LCRS (MH) m/z: 481.26); >70% proteasome CT-L inhibition at 20 mg/kg PO.

Example 4

Scheme 4: Synthesis of Example 035

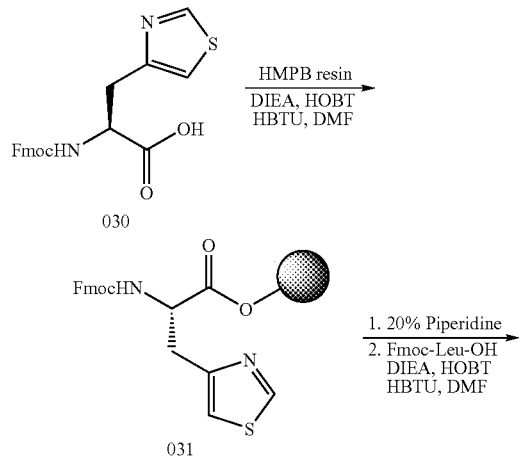

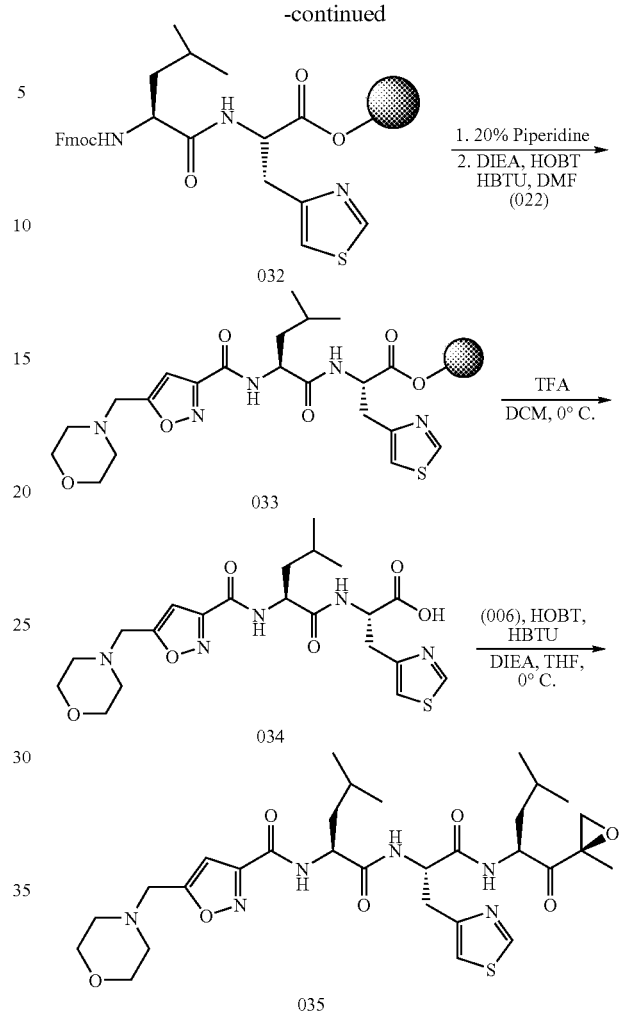

Compound (031):

To a 0° C. solution of Fmoc-L-4-thiazolylalanine (030) (1.0 g, 2.5 mmol) in dichloromethane (4 mL) were added N-methyl-imidazole (150 uL, 1.9 mmol), MSNT (755 mg, 2.55 mmol) and HMPB resin (800 mg, 0.51 mmol) was added once the mixture became homogenous. The resulting reaction mixture was allowed to shake for two hours at room temperature. The resin was then filtered off and washed with N,N-dimethylformamide (3×20 mL) and dichloromethane (3×20 mL), and allowed to air dry to yield (031).

Compound (032):

Resin (031) (360 mg, 0.23 mmol) was placed in a solution of 20% piperidine in N,N-dimethylformamide (20 mL) and the resulting mixture was shaken at room temperature for 1 hour. The resin was then filtered off and washed with N,N-dimethylformamide (3×10 mL) and dichloromethane (3×10 mL).

To a 0° C. solution of Fmoc-L-Leucine (204 mg, 0.58 mmol) in N,N-dimethylformamide (4 mL) were added HOBT (124 mg, 0.92 mmol), HBTU (349 mg 0.92 mmol) and N,N-diisopropylethylamine (402 uL, 2.3 mmol). The resin was then added once the reaction mixture became homogenous. The resulting mixture was allowed to shake at 5° C. for five 5 hours. The resin was then filtered off and washed with N,N-dimethylformamide (3×20 mL) and dichloromethane (3×20 mL), and the resulting resin was allowed to air dry to yield (032).

Compound (033):

Resin (032) (0.23 mmol) was placed in a solution of 20% piperidine in N,N-dimethylformamide (20 mL) and the resulting mixture was shaken at room temperature for 1 hour. The resin was then filtered off and washed with N,N-dimethylformamide (3×10 mL) and dichloromethane (3×10 mL).

To a 0° C. solution of (022) (123 mg 0.58 mmol) in N,N-dimethylformamide (4 mL) were added HOBT (124 mg, 0.92 mmol), HBTU (349 mg 0.92 mmol) and N,N-diisopropylethylamine (402 uL, 2.3 mmol). Once the resulting mixture became homogenous, the resin was added and the resulting reaction mixture was allowed to shake at room temperature overnight. The resin was then filtered off, washed with N,N-dimethylformamide (3×10 mL) and dichloromethane (3×10 mL), and the resulting resin was allowed to air dry to yield (033).

Compound (034):

To resin (033) was added a solution of 50% of trifluoroacetic acid in dichloromethane (10 mL), and the resulting mixture was allowed to shake for 30 minutes. It was then filtered off and the resin washed with dichloromethane (3×10 mL). The volatiles were removed under reduced pressure to provide (34) as characterized by LC/MS (LCRS (MH) m/z: 480.18) which was used without further purification.

Compound (035):

To a 0° C. solution of (034) and (006) (70 mg, 0.23 mmol), HOBT (50 mg, 0.37 mmol) and HBTU (140 mg, 0.37 mmol) in tetrahydrofuran (50 mL) was added a solution of N,N-diisopropylethylamine (0.5 mL, 2.5 mmol) in tetrahydrofuran (5 mL). The mixture was stirred at room temperature for 5 hours and then diluted with ethyl acetate (200 mL). It was then washed with saturated aqueous sodium bicarbonate (2×10 mL) and brine (10 mL). The organic layers were dried over sodium sulfate and filtered through Celite-545 and the solvents were removed under reduced pressure. The resulting residue was purified by HPLC (aqueous ammonium acetate and acetonitrile) to provide (035) (15 mg) which was characterized by LC/MS (LCRS (MH) m/z: 633.3); >90% proteasome CT-L inhibition at 40 mg/kg PO.

Example 5

Scheme 5: Synthesis of Example 039

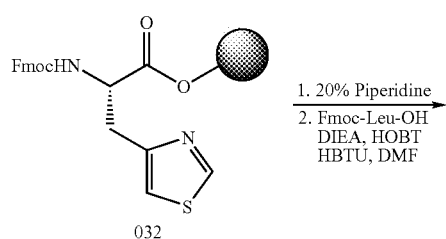

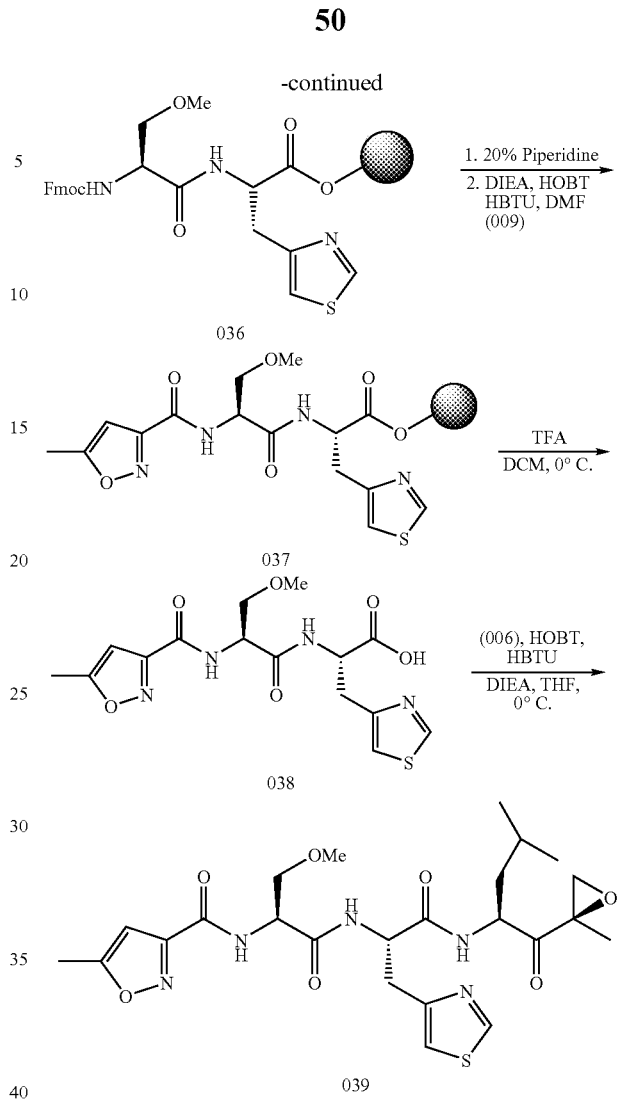

Compound (036):

Resin (031) (800 mg, 0.23 mmol) was placed in a solution of 20% piperidine in N,N-dimethylformamide (20 mL) and the resulting mixture was shaken at room temperature for 1 hour. The resin was filtered off and washed with N,N-dimethylformamide (3×10 mL) and dichloromethane (3×10 mL).

To a 0° C. solution of Fmoc-L-Ser(OMe)-OH (435 mg, 1.3 mmol) in N,N-dimethylformamide (10 mL) were added HOBT (276 mg, 2.0 mmol), HBTU (710 mg, 2.0 mmol) and N,N-diisopropylethylamine (0.9 mL, 5.1 mmol). The resin was then added once the reaction mixture became homogenous. The resulting mixture was allowed to shake at 5° C. for 5 hours. The resin was then filtered off and washed with N,N-dimethylformamide (3×20 mL) and dichloromethane (3×20 mL) and allowed to air dry to yield (036).

Compound (037):

Resin (036) was placed in a solution of 20% piperidine in N,N-dimethylformamide (20 mL) and the resulting mixture was shaken at room temperature for 1 hour. The resin was filtered off and washed with N,N-dimethylformamide (3×20 mL) and dichloromethane (3×20 mL).

To a 0° C. solution of (009) (162 mg, 1.3 mmol) in N,N-dimethylformamide (4 mL) were added HOBT (276 mg, 2.0 mmol), HBTU (710 mg, 2.0 mmol) and N,N-diisopropylethylamine (0.9 mL, 5.1 mmol). Once the resulting mixture became homogenous, the resin was added and the resulting reaction mixture was allowed to shake at room temperature overnight. The resin was then filtered off, washed with N,N-dimethylformamide (3×10 mL) and dichloromethane (3×10 mL), and allowed to air dry to yield (037).

Compound (038):

To (037) was added a solution of 50% of trifluoroacetic acid in dichloromethane (10 mL), and the resulting mixture was allowed to shake for 30 minutes. The resin was then filtered off and washed with dichloromethane (3×10 mL). The volatiles were removed under reduced pressure to provide (38) which was characterized by LC/MS (LCRS (MH) m/z: 383.09) and used without further purification.

Compound (039):

To a 0° C. solution of (038) and (006) (156 mg, 0.51 mmol), HOBT (111 mg, 0.82 mmol) and HBTU (311 mg, 0.82 mmol) in tetrahydrofuran (50 mL) was added a solution of N,N-diisopropylethylamine (0.5 mL, 2.5 mmol) in tetrahydrofuran (5 mL). The mixture was stirred at room temperature for 5 hours and became homogenous. It was then diluted with ethyl acetate (200 mL) and washed with saturated aqueous sodium bicarbonate (2×10 mL). and brine (10 mL). The organic layers were dried over sodium sulfate and filtered through Celite-545. The solvents were removed under reduced pressure and the residue was purified by HPLC (aqueous ammonium acetate and acetonitrile) to provide (039) (22 mg) which was characterized by LC/MS (LCRS (MH) m/z: 536.21); >75% proteasome CT-L inhibition at 20 mg/kg PO.

Example 6

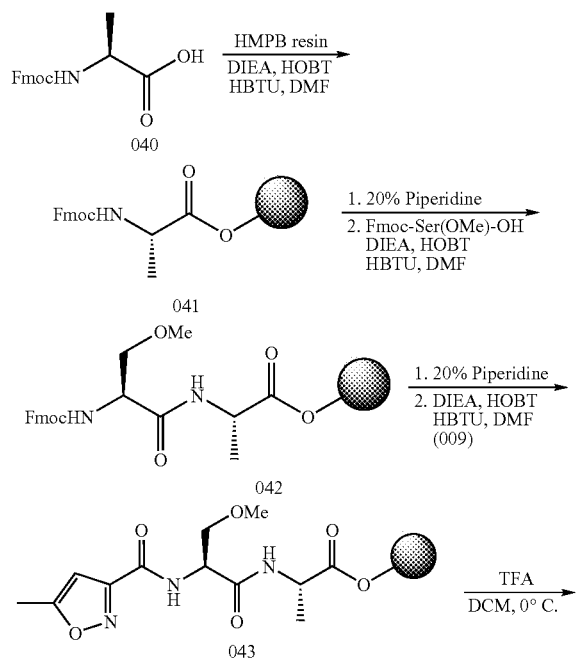

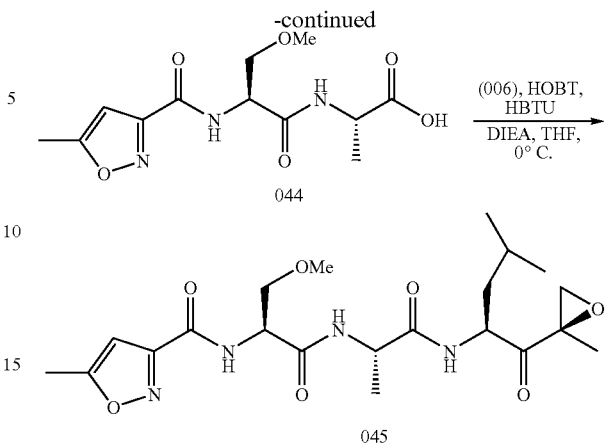

Compound (041):

To a 0° C. solution of Fmoc-L-alanine (040) (1.0 g, 3.2 mmol) in dichloromethane (30 mL) were added N-methylimidazole (190 μL, 12.4 mmol), MSNT (950 mg, 3.2 mmol), and HMPB resin (1.0 g, 0.64 mmol) which was then added once mixture became homogenous. The resulting reaction mixture was allowed to shake for two hours at room temperature. The resin was then filtered off and washed with N,N-dimethylformamide (3×20 mL) and dichloromethane (3×20 mL) to yield (041).

Compound (042):

Resin (041) was placed in a solution of 20% piperidine in N,N-dimethylformamide (20 mL) and the resulting mixture was shaken at room temperature for 1 hour. The resin was filtered off and washed with N,N-dimethylformamide (3×20 mL) and dichloromethane (3×20 mL).

To a 0° C. solution of Fmoc-Ser(OMe)-OH (546 mg, 1.6 mmol) in N,N-dimethylformamide (10 mL) were added HOBT (346 mg, 2.6 mmol), HBTU (970 mg 2.6 mmol) and N,N-diisopropylethylamine (1.1 mL, 6.4 mmol). The resin was then added once the reaction mixture became homogenous. The resulting mixture was allowed to shake at 5° C. for 5 hours. The resin was then filtered off and washed with N,N-dimethylformamide (3×20 mL) and dichloromethane (3×20 mL), and allowed to air dry to yield (042).

Compound (043):

Resin (042) (0.23 mmol) was placed in a solution of 20% piperidine in N,N-dimethylformamide (20 mL) and the resulting mixture was shaken at room temperature for 1 hour. The resin was filtered off and washed with N,N-dimethylformamide (3×10 mL) and dichloromethane (3×10 mL).

To a 0° C. solution of (009) (203 mg, 1.6 mmol) in N,N-dimethylformamide (10 mL) were added HOBT (346 mg, 2.6 mmol), HBTU (970 mg, 2.6 mmol) and N,N-diisopropylethylamine (1.1 mL, 6.4 mmol). Once the resulting mixture became homogenous, the resin was added and the resulting reaction mixture was allowed to shake at room temperature overnight. The resin was then filtered off, washed with N,N-dimethylformamide (3×20 mL) and dichloromethane (3×20 mL), and allowed to air dry to yield (043).

Compound (044):

To (043) was added a solution of 50% of trifluoroacetic acid in dichloromethane (10 mL), and the resulting mixture was allowed to shake for 30 minutes. The resin was then filtered off and washed with dichloromethane (3×10 mL). The volatiles were removed under reduced pressure to provide (044) which was characterized by LC/MS (LCRS (MH) m/z: 300.11) and used without further purification.

Compound (045):

To a 0° C. solution of aforementioned intermediates (044) and (006) (195 mg, 0.64 mmol), HOBT (137 mg, 1.0 mmol) and HBTU (357 mg, 1.0 mmol) in tetrahydrofuran (50 mL) was added a solution of N,N-diisopropylethylamine (0.5 mL, 2.5 mmol) in tetrhydrofuran (5 mL). The mixture was stirred at room temperature for 4 hours. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (045) (84 mg) which was characterized by LC/MS (LCRS (MH) m/z: 453.23); >80% proteasome CT-L inhibition at 20 mg/kg PO.

Example 7

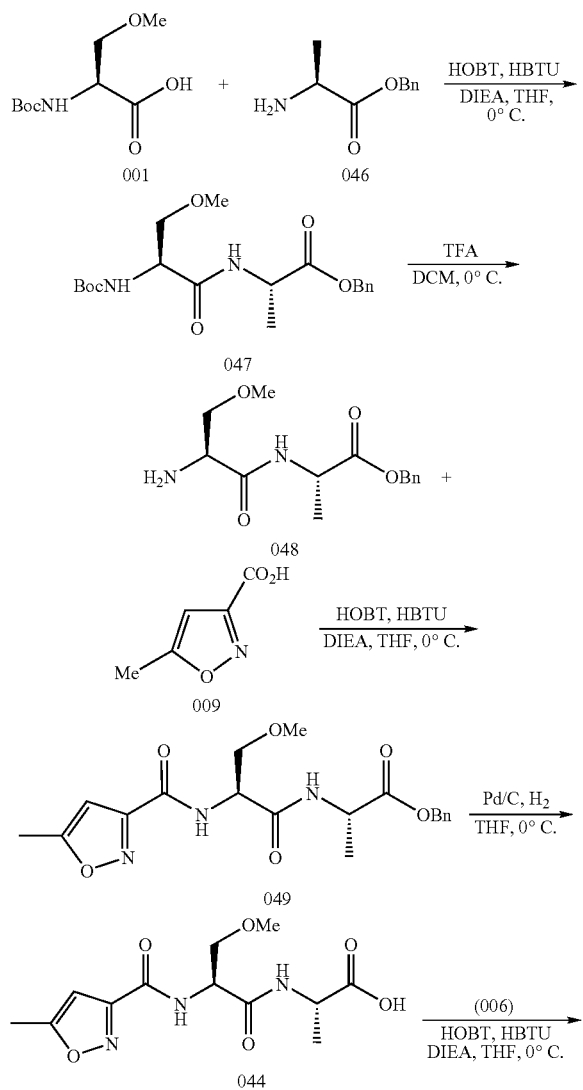

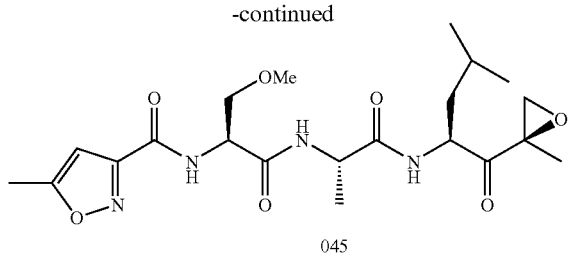

Compound (047):

To a 0° C. solution of N-Boc-serine(methyl ether) (001) (6.57 g, 33 mmol), L-alanine benzyl ester hydrochloride (046) (6.45 g, 30 mmol), HOBT (5.05 g, 33 mmol) and HBTU (11.8 g, 33 mmol) in tetrahydrofuran (400 mL) was added a solution of N,N-diisopropylethylamine (9.0 g, 70 mmol) in tetrahydrofuran (50 mL) over 10 minutes. The mixture became homogenous and was stirred at room temperature for another 5 hours. Most of the solvent was then removed under reduced pressure and the resulting material diluted with ethyl acetate (500 mL). It was washed with saturated aqueous sodium bicarbonate (2×150 mL) and brine (200 mL) and the organic layers were dried over sodium sulfate and filtered through Celite-545. The solvents were removed under reduced pressure and the residue was purified by flash chromatography (hexane and ethyl acetate) to provide (047) (11.8 g) which was characterized by LC/MS (LCRS (MH) m/z: 381.19).

Compound (048):

To a 0° C. solution of (047) (11.8 g, 31.0 mmol) in dichloromethane (100 mL) was added trifluoroacetic acid (50 mL) over 10 minutes, and the resulting mixture was stirred at the same temperature for another 3 hours. The solvents were then removed under reduced pressure and the residue was placed under high vacuum overnight to provide the TFA salt of (048), which was characterized by LC/MS (LCRS (MH) m/z: 281.15) and was used without further purification.

Compound (049):

To a 0° C. solution of (048), 5-methyl-isoxazole-3-carboxylic acid (009) (3.93 g, 31 mmol), HOBT (4.7 g, 35 mmol) and HBTU (12.5 g, 35 mmol) in tetrahydrofuran (400 mL) was added a solution of N,N-diisopropylethylamine (20 mL) in tetrahydrofuran (100 mL) over 10 minutes, and the pH of the resulting mixture was ~8. The mixture was stirred at room temperature for another 5 hours. Most of the solvent was then removed under reduced pressure and diluted with ethyl acetate (1.0 L). It was then washed with saturated aqueous sodium bicarbonate (2×100 mL) and brine (100 mL) and the organic layers were dried over sodium sulfate and filtered through Celite-545. The solvents were removed under reduced pressure and residue was purified by flash chromatography (hexane and ethyl acetate) to provide (049) (10.8 g) which was characterized by LC/MS (LCRS (MH) m/z: 390.16).

Compound (044):

To a 0° C. solution of (049) (3.28 g, 8.4 mmol) in tetrahydrofuran (100 mL) was added 10% Pd/C (500 mg). The resulting mixture was allowed to stir under 1 atmosphere of hydrogen for 4 hours. The mixture was then filtered through Celite-545 and the filter cake was washed with tetrahydrofuran. The organic filtrate was concentrated under reduced pressure and placed under high vacuum for 2 hrs to yield (044), which was characterized by LC/MS (LCRS (MH) m/z: 281.15) and was used without further purification.

Compound (045):

To a 0° C. solution of (044) and (006) (1.9 g, 8.5 mmol), HOBT (2.0 g, 13 mmol) and HBTU (5.4 g, 14 mmol) in tetrahydrofuran (200 mL) was added a solution of N,N-diisopropylethylamine (5.4 g, 42 mmol) in tetrahydrofuran (10 mL). The mixture was stirred at room temperature for another 5 hours. Most of the solvent was then removed under reduced pressure and the resulting material diluted with ethyl acetate (400 mL). It was then washed with saturated aqueous sodium bicarbonate (2×50 mL) and brine (50 mL) and the organic layers were dried over sodium sulfate and filtered through Celite-545. The solvents were removed under reduced pressure and residue was purified by HPLC (aqueous ammonium acetate and acetonitrile) to provide (045) (1.35 g) which was characterized by LC/MS (LCRS (MH) m/z: 453.23).

Example 8

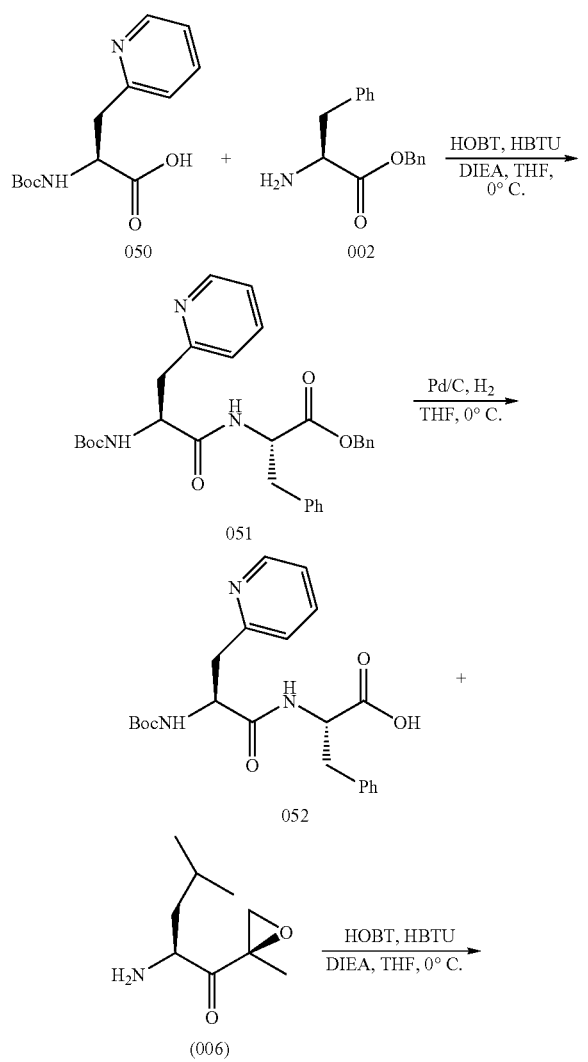

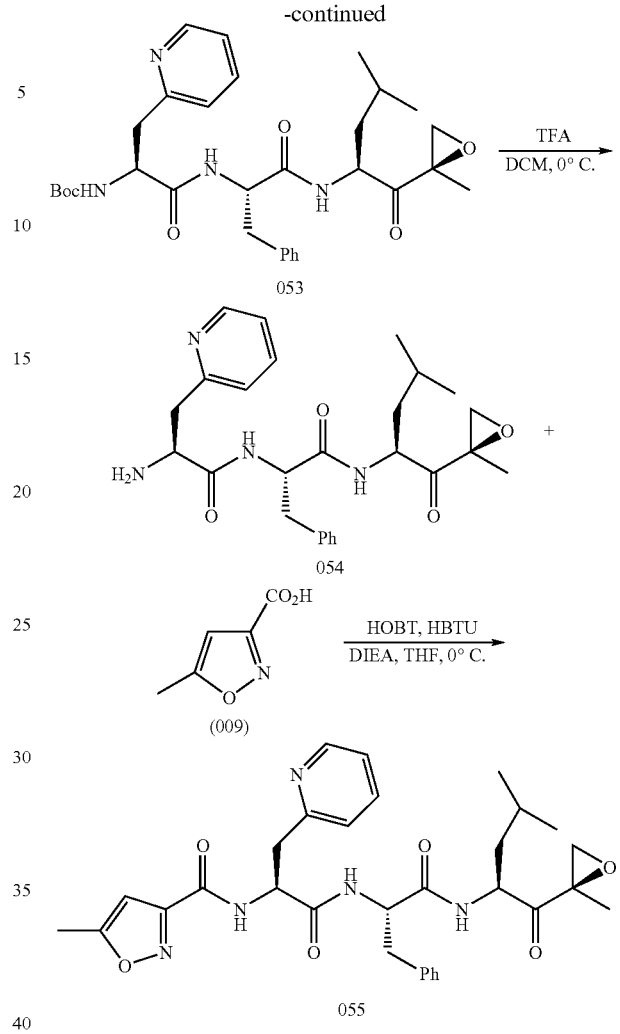

Compound (051):

To a 0° C. solution of N-Boc-L-2-pyridylalanine (050) (1.0 g, 3.76 mmol), L-phenylalanine benzyl ester hydrochloride (002) (1.3 g, 3.76 mmol), HOBT (0.68 g, 5.0 mmol) and HBTU (1.8 g, 5.0 mmol) in tetrahydrofuran (100 mL) was added a solution of N,N-diisopropylethylamine (1.6 mL) in tetrahydrofuran (10 mL). The mixture was stirred at room temperature for another 3 hours and then diluted with ethyl acetate (200 mL), washed with saturated aqueous sodium bicarbonate (2×50 mL) and brine (100 mL) and the organic layers were dried over sodium sulfate and filtered through Celite-545. The solvent was removed under reduced pressure and the residue was purified by flash chromatography (hexane and ethyl acetate) to provide (051) (1.45 g) which was characterized by LC/MS (LCRS (MH) m/z: 504.24).

Compound (052):

To a 0° C. solution of (051) in tetrahydrofuran (100 mL) was added 10% Pd/C (100 mg) and the resulting mixture was allowed to stir under 1 atmosphere of hydrogen for 4 hours. The mixture was then filtered through Celite-545 and the filter cake was washed with tetrahydrofuran. The organic filtrate was then concentrated under reduced pressure and placed under high vacuum to provide (052) by LC/MS (LCRS (NH) m/z: 414.2) which was used without further purification.

Compound (053):

To a 0° C. solution of (052) and (006) (0.85 g, 3.9 mmol), HOBT (0.70 g, 5.3 mmol) and HBTU (1.70 g, 4.9 mmol) in tetrahydrofuran (100 mL) was added a solution of N,N-diisopropylethylamine (3 mL) in tetrahydrofuran (10 mL) and the mixture was stirred at room temperature overnight. It was then diluted with ethyl acetate (200 mL) and washed with saturated aqueous sodium bicarbonate (2×50 mL) and brine (50 mL). The organic layers were dried over sodium sulfate and filtered through Celite-545, and the solvents were removed under reduced pressure and the residue was purified by flash chromatography (hexane and ethyl acetate) and HPLC (aqueous ammonium acetate and acetonitrile) to provide (053) (1.51 g) which was characterized by LC/MS (LCRS (MH) m/z: 567.21).

Compound (054):

To a 0° C. solution of (053) (200 mg, 0.352 mmol) in dichloromethane (10 mL) was added trifluoroacetic acid (10 mL), and the resulting solution was stirred at the same temperature for another hour. The solution was concentrated under reduced pressure and placed under high vacuum to provide (054) as confirmed by LC/MS (LCRS (MH) m/z: 467.26) which was used without further purification.

Compound(055):

To a 0° C. solution of (054) and 5-methyl-isoxazole-3-carboxylic acid (009) (127 mg, 1.0 mmol), HOBT (135 mg, 1.0 mmol) and HBTU (350 mg, 1.0 mmol) in tetrahydrofuran (100 mL) was added a solution of N,N-diisopropylethylamine (0.5 mL) in tetrahydrofuran (2 mL). The mixture was stirred at room temperature for 5 hours. It was then diluted with ethyl acetate (200 mL) and washed with saturated aqueous sodium bicarbonate (2×10 mL) and brine (10 mL). The organic layers were dried over sodium sulfate and filtered through Celite-545, the solvents were removed under reduced pressure and the residue was purified by HPLC (aqueous ammonium acetate and acetonitrile) to provide (055) (40 mg) which was characterized by LC/MS (LCRS (MH) m/z: 576.27); >80% proteasome CT-L inhibition at 20 mg/kg PO.

Example 9

Scheme 9: Synthesis of Example 061

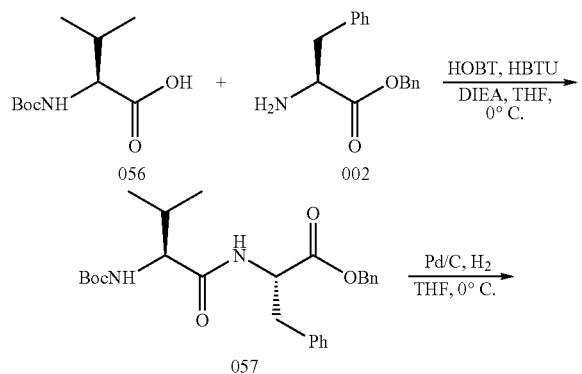

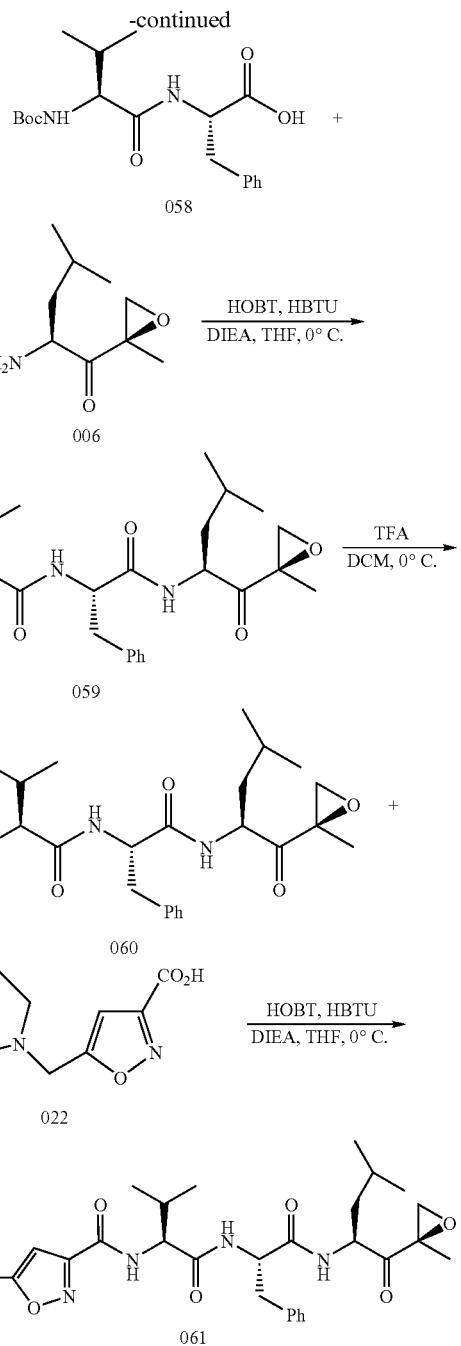

Compound (057):

To a 0° C. solution of N-Boc-L-n-valine (056) (1.0 g, 4.6 mmol), L-phenylalanine benzyl ester hydrochloride (002) (1.4 g, 4.6 mmol), HOBT (1.0 g, 7.4 mmol) and HBTU (2.8 g, 7.4 mmol) in tetrahydrofuran (100 mL) was added a solution of N,N-diisopropylethylamine (3.2 mL, 18.4 mmol) in tetrahydrofuran (10 mL). The mixture was stirred at room temperature for 3 hours and then diluted with ethyl acetate (200 mL), washed with saturated aqueous sodium bicarbonate (2×50 mL) and brine (100 mL), and the organic layers were dried over sodium sulfate and filtered through Celite-545. The solvent was removed under reduced pressure and the residue was purified by flash chromatography (hexane and ethyl acetate) to provide (057) which was characterized by LC/MS (LCRS (MH) m/z: 455.25).

Compound (058):

To a 0° C. solution of (057) (1.30 g, 2.875 mmol) in tetrahydrofuran (100 mL) was added 10% Pd/C (100 mg). The resulting mixture was allowed to stir under 1 atmosphere of hydrogen for 4 hours. The mixture was filtered through Celite-545 and the filter cake was washed with tetrahydrofuran. The filtrate was then concentrated under reduced pressure and placed under high vacuum to provide (058) as confirmed by LC/MS (LCRS (MH) m/z: 365.2) which was used without further purification.

Compound (059):

To a 0° C. solution of (058) and (006) (0.99 g, 4.6 mmol), HOBT (0.62 g, 4.6 mmol) and HBTU (1.70 g, 4.9 mmol) in tetrahydrofuran (100 mL) was added a solution of N,N-diisopropylethylamine (2.4 mL) in tetrahydrofuran (10 mL). The mixture was stirred at room temperature overnight and was then diluted with ethyl acetate (200 mL) and washed with saturated aqueous sodium bicarbonate (2×50 mL) and brine (50 mL). The organic layers were dried over sodium sulfate and filtered through Celite-545. The solvents were then removed under reduced pressure and the residue was purified by HPLC (aqueous ammonium acetate and acetonitrile) to provide (059) (1.21 g) which was characterized by LC/MS (LCRS (MH) m/z: 518.32).

Compound (060):

To a 0° C. solution of (059) (250 mg, 0.48 mmol) in dichloromethane (10 mL) was added trifluoroacetic acid (10 mL), and the resulting solution was stirred at the same temperature for another hour. The organic layers were concentrated under reduced pressure and placed under high vacuum to provide (060) as confirmed by LC/MS (LCRS (MH) m/z: 418.26) which was used without further purification.

Compound (061):

To a 0° C. solution of (060) and (022) (122 mg, 0.58 mmol), HOBT (104 mg, 0.77 mmol) and HBTU (292 mg, 0.72 mmol) in tetrahydrofuran (100 mL) was added a solution of N,N-diisopropylethylamine (0.35 mL) in tetrahydrofuran (2 mL) and the mixture was stirred at room temperature for another 4 hours. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (061) (88.4 mg) which was characterized by LC/MS (LCRS (MH) m/z: 612.33); >80% proteasome CT-L inhibition at 40 mg/kg PO.

Example 10

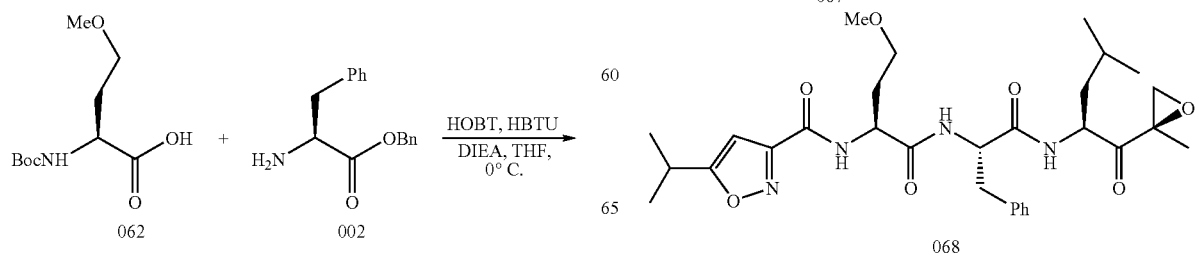

Compound (063):

To a 0° C. solution of N-Boc-HoSer(OMe)-OH (062) (1.0 g, 4.3 mmol), L-phenylalanine benzyl ester hydrochloride (002) (1.3 g, 4.3 mmol), HOBT (0.88 g, 6.5 mmol) and HBTU (2.3 g, 6.5 mmol) in tetrahydrofuran (100 mL) was added a solution of N,N-diisopropylethylamine (2.0 mL) in tetrahydrofuran (5 mL). The mixture was stirred at room temperature for another 3 hours and then diluted with ethyl acetate (200 mL) and washed with saturated aqueous sodium bicarbonate (2×50 mL) and brine (100 mL). The organic layers were dried over sodium sulfate and filtered through Celite-545. The solvents were removed under reduced pressure and the residue was purified by flash chromatography (hexane and ethyl acetate) to provide (063) (1.81 g) which was characterized by LC/MS (LCRS (MH) m/z: 471.24).

Compound (064):

To a 0° C. solution of (063) (1.35 g, 2.875 mmol) in tetrahydrofuran (100 mL) was added 10% Pd/C (100 mg). The resulting mixture was allowed to stir under 1 atmosphere of hydrogen for 4 hours. The mixture was filtered through Celite-545 and the filter cake was washed with tetrahydrofuran. The organic filtrate was concentrated under reduced pressure and placed under high vacuum to provide (064) as confirmed by LC/MS (LCRS (MH) m/z: 381.19) which was used without further purification.

Compound (065):

To a 0° C. solution of (065) and (006) (0.99 g, 4.6 mmol), HOBT (0.62 g, 4.6 mmol) and HBTU (1.70 g, 4.9 mmol) in tetrahydrofuran (100 mL) was added a solution of N,N-diisopropylethylamine (2.4 mL) in tetrahydrofuran (10 mL). The mixture was stirred at room temperature overnight and then diluted with ethyl acetate (200 mL) and washed with saturated aqueous sodium bicarbonate (2×50 mL) and brine (50 mL). The organic layers were dried over sodium sulfate and filtered through Celite-545. The solvents were removed under reduced pressure and the residue was purified by HPLC (aqueous ammonium acetate and acetonitrile) to provide (065) (1.11 g) which was characterized by LC/MS (LCRS (MH) m/z: 534.31).

Compound (066):

To a 0° C. solution of (065) (230 mg, 0.43 mmol) in dichloromethane (20 mL) was added trifluoroacetic acid (10 mL), and the resulting solution was stirred at the same temperature for another one hour. The reaction mixture was then concentrated under reduced pressure and placed under high vacuum to provide (066) as confirmed by LC/MS (LCRS (MH) m/z: 434.26) which was used without further purification.

Compound (068):

To a 0° C. solution of (066) and 5-isopropylisoxazole-3-carboxylic acid (067) (81 mg, 0.52 mmol), HOBT (93 mg, 0.69 mmol) and HBTU (262 mg, 0.69 mmol) in tetrahydrofuran (100 mL) was added a solution of N,N-diisopropylethylamine (0.30 mL) in tetrahydrofuran (2 mL) and the mixture was stirred at room temperature for another 4 hours. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (068) (75.7 mg) which was characterized by LC/MS (LCRS (MH) m/z: 571.31); >70% proteasome CT-L inhibition at 40 mg/kg PO.

Example 11

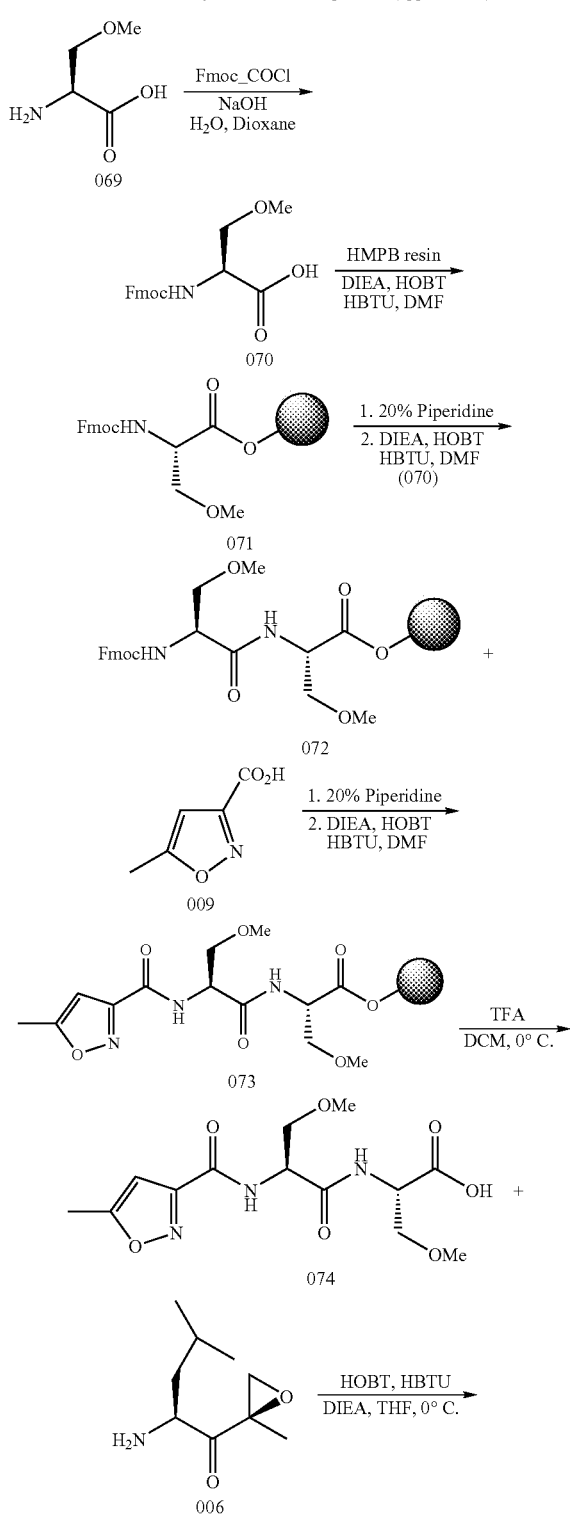

Scheme 11: Synthesis of Example 075 (approach A)

-continued

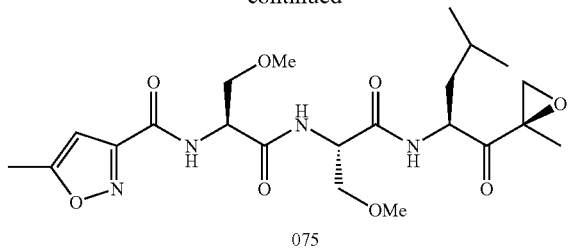

075

Compound (070):

To a solution of L-serine (methyl ether) hydrochloride (069) (1.0 g, 6.4 mmol) in water/dioxane (1:1, 80 ml) was added sodium hydroxide (768 mg, 19.2 mmol). After the mixture was stirred at room temperature for 30 minutes, it was cooled to 0 °C., and a solution of 9-fluorenylmethyl chloroformate (1.65 g, 6.4 mmol) in dioxane (16 mL) was added dropwisely. The reaction mixture was allowed to stir at room temperature for another 4 hours. The solvents were then removed, the residue was diluted with water and the pH was adjusted to ~1 with 1N HCl, and the aqueous layer was extracted with ethyl acetate (4×100 mL). The organic layers were concentrated under reduced pressure and placed under high vacuum to provide (070) (1.8 g) as confirmed by LC/MS (LCRS (MH) m/z: 342.13) which was used without further purification.

Compound (071):

The resin HMPB-BHA (500 mg, 0.32 mmol ) was washed with dichloromethane. In a dry flask, Fmoc-Ser(Me)-OH (070) (546 mg, 1.6 mmol) was dissolved in dichloromethane and to the solution was added 1-methylimidazole (95 µL, 1.2 mmol) followed by MSNT (474 mg, 1.6 mmol). Once the resulting mixture had become homogenous (10 minutes) it was added to the HMPB-BHA resin as a suspension in dichloromethane (5 mL). The resulting reaction mixture was allowed to shake overnight. The resin was then filtered off and washed with DMF (3×20 mL), MeOH (3×20 mL), DCM (3×20 mL), and allowed to air dry to yield (071).

Compound (072):

Resin (071) (300 mg, 0.192 mmol) was placed in a solution of 20% piperidine in N,N-dimethylformamide (20 mL) and the resulting mixture was shaken at room temperature for 30 minutes. The resin was filtered off and washed with N,N-dimethylformamide (3×20 mL) and dichloromethane (3×20 mL) twice.

To a 0° C. solution of Fmoc-Ser(Me)-OH (070) (0.48 mmol, 163 mg) in N,N-dimethylformamide (10 mL) was added HOBT (104 mg, 0.77 mmol), HBTU (291 mg, 0.77 mmol) and diisopropylethylamine (0.34 mL, 1.92 mmol). Once the resulting mixture became homogenous, the resin (0.13 mmol, 200 mg) was added and the resulting reaction mixture was allowed to shake overnight. The resin was then filtered off and washed with DMF (10 mL), DCM (10 mL), MeOH (10 mL), H$_2$O (10 mL), DMF (10 mL), MeOH (10 mL), and DCM (10 mL), and allowed to air dry to yield (072).

Compound (073):

To (072) (300 mg, 0.19 mmol) was added a solution of 20% piperidine in N,N-dimethylformamide (20 mL) and the resulting mixture was shaken at room temperature for 30 minutes. The resin was filtered off and washed with N,N-dimethylformamide (3×20 mL) and dichloromethane (3×20 mL) twice.

To a 0° C. solution of (009) (61 mg, 0.48 mmol) in N,N-dimethylformamide (2 mL) was added HOBT (104 mg, 0.77 mmol), HBTU (291 mg 0.77 mmol) and N,N-diisopropylethylamine (0.34 mL, 1.92 mmol). Once the resulting mixture became homogenous, the resin (300 mg, 0.192 mmol) was added and the resulting reaction mixture was allowed to shake at room temperature overnight. The resin was then filtered off, washed with DMF (10 mL), DCM (10 mL), MeOH (10 mL), H$_2$O (10 mL), DMF (10 mL), MeOH (10 mL), and DCM (10 mL), and allowed to air dry to yield (073).

Compound (074):

To (073) was added a solution of 50% of trifluoroacetic acid in dichloromethane (10 mL), and the resulting mixture was allowed to shake for 30 minutes. The resin was then filtered off and washed with dichloromethane (3×10 mL). The volatiles were removed under reduced pressure, and the desired compound (074) was characterized by LC/MS (LCRS (MH) m/z: 330.12) and used without further purification.

Compound (075):

To a 0° C. solution of (074) and (006) (78 mg, 0.38 mmol), HOBT (41 mg, 0.30 mmol) and HBTU (116 mg, 0.30 mmol) in acetonitrile (50 mL) was added a solution of N,N-diisopropylethylamine (0.1 mL, 0.6 mmol). The mixture was stirred at 0-4° C. overnight and then diluted with ethyl acetate (200 mL). It was then washed with saturated aqueous sodium bicarbonate (2×10 mL) and brine (10 mL) and the organic layers were dried over sodium sulfate and filtered through Celite-545. The solvents were removed under reduced pressure and the residue was purified by HPLC (aqueous ammonium acetate and acetonitrile) to provide (075) (29 mg) which was characterized by LC/MS (LCRS (MH) m/z: 483.24); >80% proteasome CT-L inhibition at 20 mg/kg PO.

Example 12

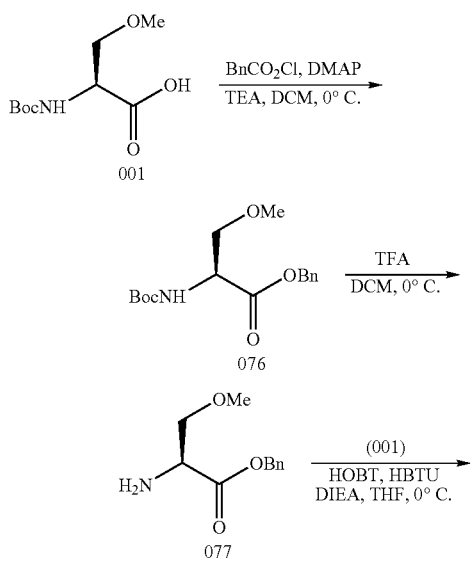

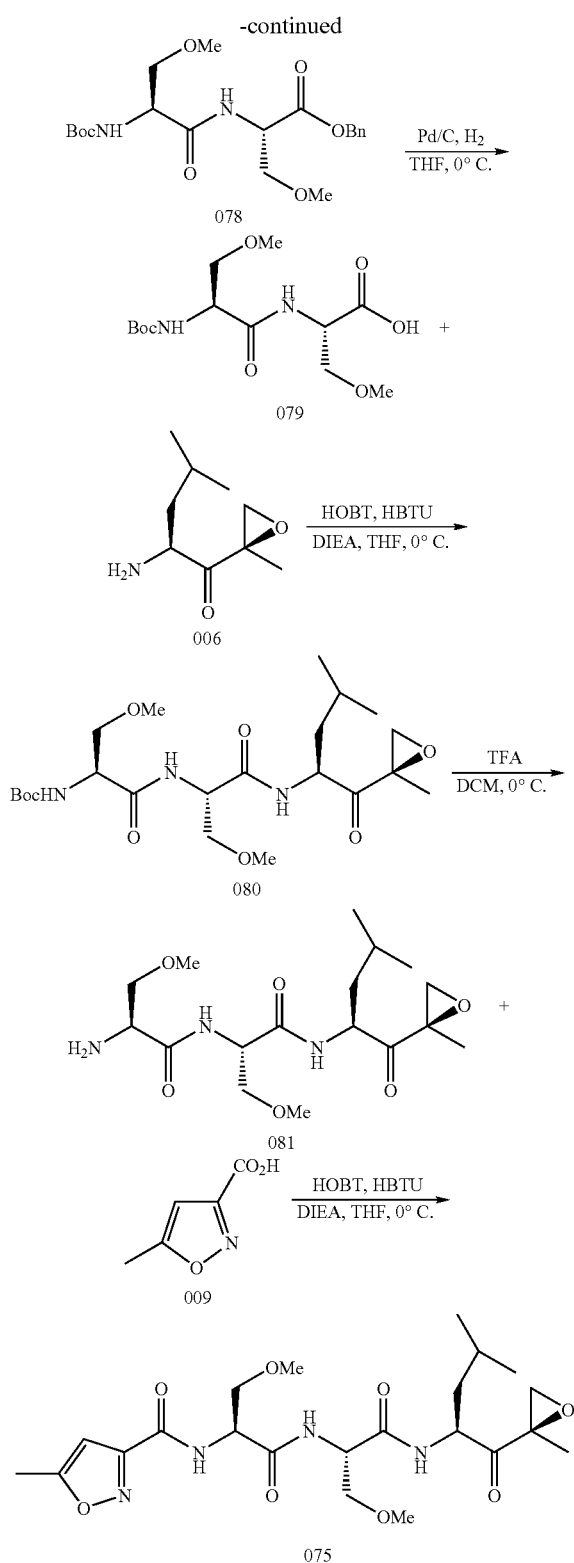

dichloromethane (250 mL) over 30 minutes and the resulting mixture was stirred at the same temperature for another 3 hours. Saturated aqueous sodium bicarbonate (200 mL) was then added and the organic layer was washed with saturated aqueous sodium bicarbonate (200 mL) and brine (200 mL). The organic layers were dried over sodium sulfate and filtered through Celite-545. The solvents were removed under reduced pressure and residue was purified by flash chromatography (hexane and ethyl acetate) to provide (076) (54 g) which was characterized by LC/MS (LCRS (MH) m/z: 310.16).

Compound (077):

To a 0° C. solution of (076) (54 g, 174.6 mmol) in dichloromethane (200 mL) was added trifluoroacetic acid (200 mL) over 10 minutes, and the resulting mixture was stirred at the same temperature for another 3 hours. The solvents were then removed under reduced pressure and the residue was placed under high vacuum overnight giving the TFA salt of (077), confirmed by LC/MS (LCRS (MH) m/z: 210.11), and was used without further purification.

Compound (078):

To a 0° C. solution of (077) (43.8 g, 200 mmol), N-Boc serine(methyl ether)-OH (36.7 g, 167 mmol), HOBT (27 g, 200 mmol) and HBTU (71.4 g, 200 mmol) in tetrahydrofuran (1.2 L) was added a solution of N,N-diisopropylethylamine (75 g, 600 mmol) in tetrahydrofuran (250 mL) over 10 minutes, and pH of the resulting mixture was ~8. The mixture was stirred at room temperature for another 5 hours. Most of the solvent was then removed under reduced pressure and the resulting material diluted with ethyl acetate (1.0 L). It was then washed with saturated aqueous sodium bicarbonate (2×150 mL) and brine (200 mL) and the organic layers were dried over sodium sulfate and filtered through Celite-545. The solvents were removed under reduced pressure and residue was purified by flash chromatography (hexane and ethyl acetate) to provide (078) (65 g) which was characterized by LC/MS (LCRS (MH) m/z: 411.21).

Compound (079):

To a 0° C. solution of (079) (13.4 g, 32.7 mmol) in tetrahydrofuran (300 mL) was added 10% Pd/C (2.7 g) and the resulting mixture was allowed to stir under 1 atmosphere of hydrogen for 4 hours. The mixture was filtered through Celite-545 and the filter cake was washed with tetrahydrofuran. The organic layers were concentrated under reduced pressure and placed under high vacuum to provide (079) as confirmed by LC/MS (LCRS (MH) m/z: 321.16) which was used without further purification.

Compound (080):

To a 0° C. solution of (079) and (006) (5.6 g, 26 mmol), HOBT (6.0 g, 41.4 mmol) and HBTU (14.8 g, 41.4 mmol) in tetrahydrofuran (400 mL) was added a solution of N,N-diisopropylethylamine (23 mL) in tetrahydrofuran (40 mL) and the mixture was stirred at room temperature overnight. Most of the solvent was then removed under reduced pressure and the resulting material diluted with ethyl acetate (500 mL) and washed with saturated aqueous sodium bicarbonate (2×100 mL) and brine (100 mL). The organic layers were dried over sodium sulfate and filtered through Celite-545. The solvents were removed under reduced pressure and the residue was purified by flash chromatography (hexane and ethyl acetate) to provide (080) (9.2 g) which was characterized by LC/MS (LCRS (MH) m/z: 474.27).

Compound (076):

To a 0° C. solution of N-Boc serine(methyl ether)-OH (43.8 g, 200 mmol), triethylamine (26.5 g, 260 mmol) and 4-(dimethylamino)pyridine in dichloromethane (1.2 L) was added a solution of benzyl chloroformate (41 g, 240 mmol) in Compound (081):

To a 0° C. solution of (080) (200 mg, 0.43 mmol) in dichloromethane (10 mL) was added trifluoroacetic acid (10 mL), and the resulting solution was stirred at the same temperature for another hour. The organic layers were concentrated under reduced pressure and placed under high vacuum to provide (081) as confirmed by LC/MS (LCRS (MH) m/z: 374.22) which was used without further purification.

Compound (075):

To a 0° C. solution of (081) and 5-methyl-isoxazole-3-carboxylic acid (009) (65 mg, 0.5 mmol), HOBT (65 mg, 0.5 mmol) and HBTU (175 mg, 0.5 mmol) in tetrahydrofuran (50 mL) was added a solution of N,N-diisopropylethylamine (0.5 mL) in tetrahydrofuran (2 mL) and the mixture was stirred at room temperature for another 5 hours. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (075) (85 mg) which was characterized by LC/MS (LCRS (MH) m/z: 483.24).

Example 13

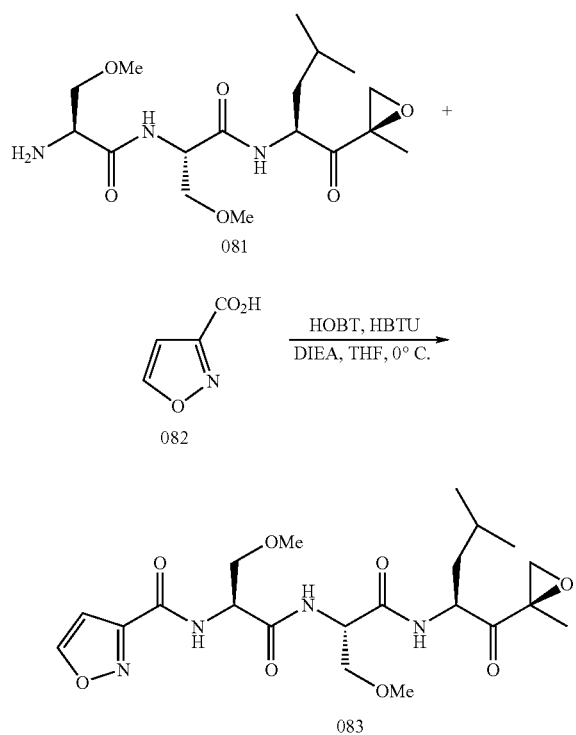

Compound (083):

To a 0° C. solution of (081) (160 mg, 0.43 mmol) and isoxazole-3-carboxylic acid (082) (60 mg, 0.5 mmol), HOBT (65 mg, 0.5 mmol) and HBTU (175 mg, 0.5 mmol) in tetrahydrofuran (50 mL) was added a solution of N,N-diisopropylethylamine (0.5 mL) in tetrahydrofuran (2 mL) and the mixture was stirred at room temperature for another 5 hours. It was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (083) (74 mg) which was characterized by LC/MS (LCRS (MH) m/z: 469.22); >80% proteasome CT-L inhibition at 20 mg/kg PO.

Example 14

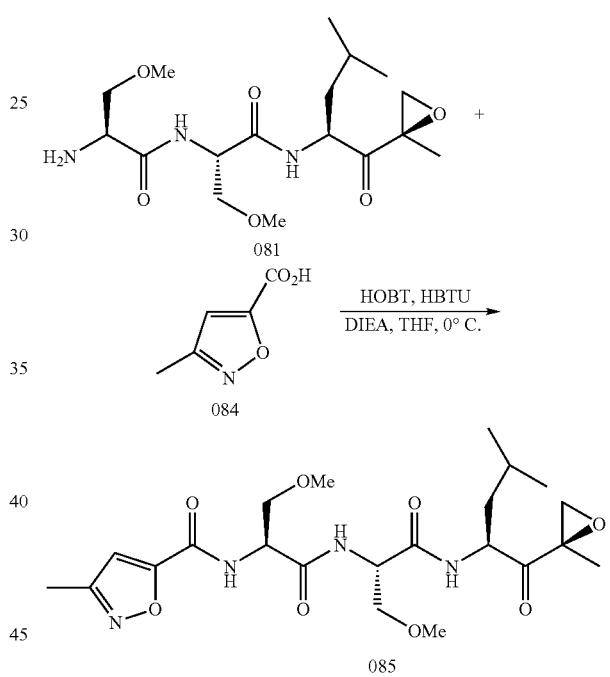

Compound (085):

To a 0° C. solution of (081) (160 mg, 0.43 mmol) and isoxazole-3-carboxylic acid (084) (65 mg, 0.5 mmol), HOBT (65 mg, 0.5 mmol) and HBTU (175 mg, 0.5 mmol) in tetrahydrofuran (50 mL) was added a solution of N,N-diisopropylethylamine (0.5 mL) in tetrahydrofuran (2 mL) and the mixture was stirred at room temperature for another 5 hours. The reaction was then diluted with ethyl acetate (200 mL) and washed with saturated aqueous sodium bicarbonate (2×10 mL) and brine (10 mL). The organic layers were dried over sodium sulfate and filtered through Celite-545. The solvents were removed under reduced pressure and the residue was purified by HPLC (aqueous ammonium acetate and acetonitrile) to provide (085) (71 mg) which was characterized by LC/MS (LCRS (MH) m/z: 483.24); >50% proteasome CT-L inhibition at 20 mg/kg PO.

Scheme 15: Synthesis of Example 088

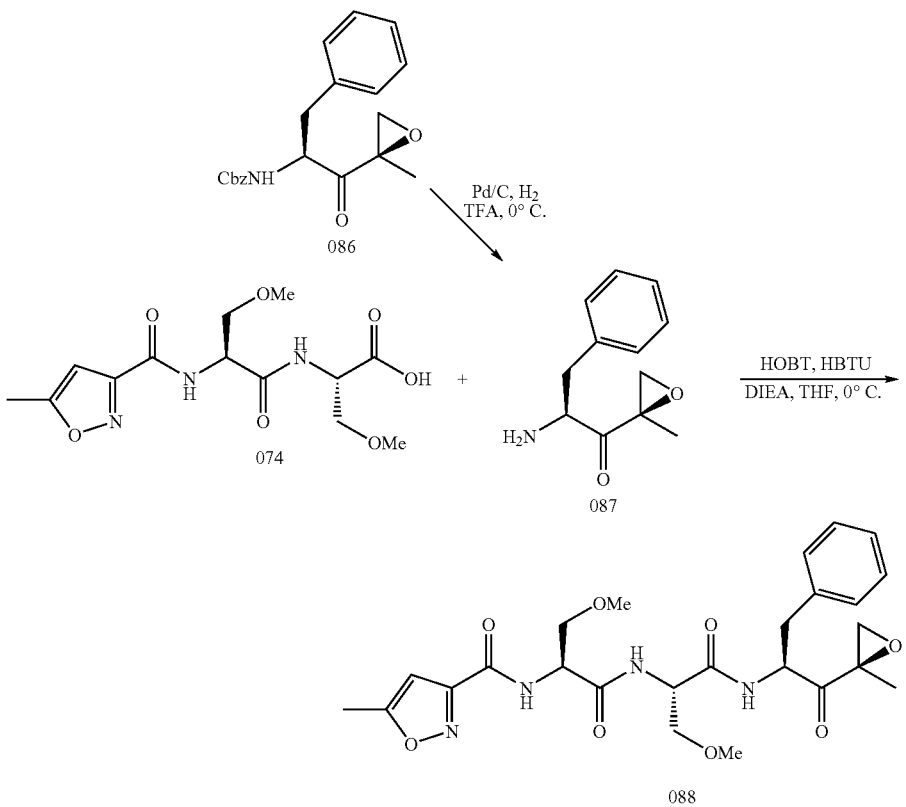

Compound (087):

To a solution of (086) (prepared using the same procedure as (005) except that Cbz-phenylalanine was substituted for Cbz-Leucine) (0.100 g, 0.0295 mmol) in trifluoroacetic acid (10 mL) was added 10% Pd/C (20 mg). The resulting mixture was allowed to stir under 1 atmosphere of hydrogen for 6 hours. The mixture was then filtered through Celite-545 and the filter cake washed with dichloromethane (50 mL). The filtrate was concentrated under reduced pressure and placed under high vacuum overnight to provide (087) as confirmed by LC/MS (LCRS (MH) m/z: 206.1) which was used in the subsequent transformation without further purification.

Compound (088):

To a 0° C. solution of (087) and (074) (166 mg, 0.354 mmol), HOBT (54 mg, 0.354 mmol) and HBTU (134 mg, 0.354 mmol) in tetrahydrofuran (20 mL) was added N,N-diisopropylethylamine (0.2 mL, 1.18 mmol). The mixture was stirred 0° C. overnight and became homogenous. It was then diluted with ethyl acetate (20 mL) and washed with saturated aqueous sodium bicarbonate (2×10 mL) and brine (10 mL). The organic layers were dried over sodium sulfate and filtered through Celite-545 and concentrated under reduced pressure and the residue was purified by HPLC (aqueous ammonium acetate and acetonitrile) to provide (088) (10 mg) as characterized by LC/MS (LCRS (MH) m/z: 517.69); >80% proteasome CT-L inhibition at 20 mg/kg PO.

Scheme 16: Synthesis of Example 091

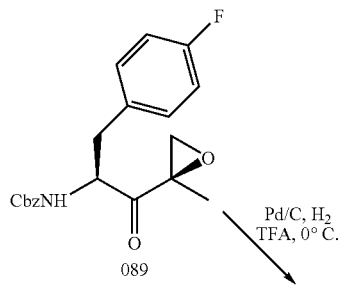

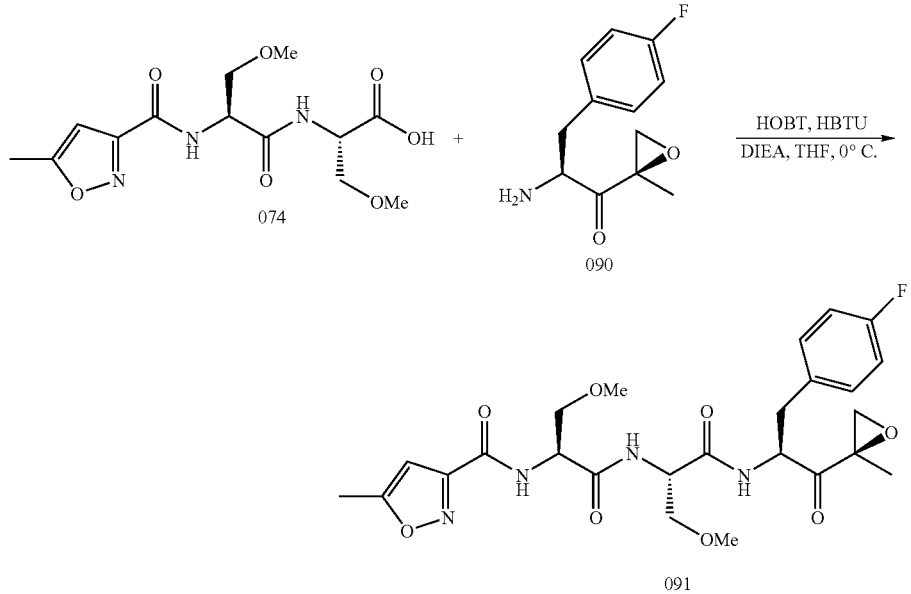

Compound (090):

To a solution of (089) (prepared using the same procedure as for (005) except that Cbz-4-fluorophenylalanine was substituted for Cbz-leucine) (0.100 g, 0.28 mmol) in trifluoroacetic acid (10 mL) was added 10% Pd/C (20 mg). The resulting mixture was allowed to stir under 1 atmosphere of hydrogen for 6 hours. The mixture was filtered through Celite-545 and the filter cake washed with dichloromethane (50 mL). The filtrate was concentrated under reduced pressure and placed under high vacuum overnight to provide (090) as confirmed by LC/MS (LCRS (MH) m/z: 224.1) which was used in the subsequent transformation without further purification.

Compound (091):

To a 0° C. solution of (090) and (074) (110 mg, 0.336 mmol), HOBT (51 mg, 0.336 mmol) and HBTU (127 mg, 0.336 mmol) in tetrahydrofuran (20 mL) was added N,N-diisopropylethylamine (0.2 mL, 1.18 mmol). The mixture was stirred 0° C. overnight and became homogenous. It was then diluted with ethyl acetate (20 mL) and washed with saturated aqueous sodium bicarbonate (2×10 mL) and brine (10 mL). The organic layers were dried over sodium sulfate, filtered through Celite-545, and concentrated under reduced pressure. The residue was then purified by HPLC (aqueous ammonium acetate and acetonitrile) to provide (091) (60 mg) which was characterized by LC/MS (LCRS (MH) m/z: 535.69); >80% proteasome CT-L inhibition at 20 mg/kg PO.

Biological Activity

Compounds were formulated in 10% PS80/NaCitrate (pH 3) vehicle and administered to mice orally (PO) (3 animals/cohort). One hour post-dosing, the animals were sacrificed and the following tissues harvested: blood, brain, adrenal gland, heart and liver. Whole blood (~200 μl) was washed twice with PBS and lysed by hypotonic shock (300 μl 50 mM Tris pH 8, 5 mM EDTA). Blood lysates were stored at −80° C. until assayed. Blood lysates were clarified by centrifugation in a microcentrifuge. The CT-L specific activity of proteasome in each lysate was evaluated by determining: a) the protein concentration by modified Bradford assay with bovine gamma globulin as a standard; and b) the rate of cleavage of the fluorogenic proteasome substrate LLVY-AMC. The percent proteasome activity for the analog-treated animals was calculated by dividing of the average specific activity for each analog-dosed cohort by the average specific activity of the vehicle-dosed cohort. Percent proteasome inhibition was calculated by subtracting percent proteasome activity from 100.

Equivalents

Those skilled in the art will recognize, or be able to ascertain using no more than routine experimentation, numerous equivalents to the compounds and methods of use thereof described herein. Such equivalents are considered to be within the scope of this invention and are covered by the following claims.

All of the above-cited references and publications are hereby incorporated by reference.

We claim:

1. A compound having a structure of formula (I) or a pharmaceutically acceptable salt thereof:

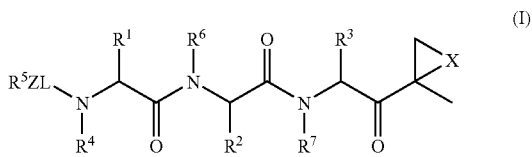

wherein
L is selected from C═O and C═S;
X is selected from O, S, NH, and N—$C_{1-6}$alkyl;
Z is absent, $C_{1-6}$alkyl, or $C_{1-6}$alkoxy;
$R^1$, $R^2$, and $R^3$ are each independently selected from hydrogen, $C_{1-6}$alkyl, $C_{1-6}$alkenyl, $C_{1-6}$alkynyl, $C_{1-6}$hydroxyalkyl, $C_{1-6}$alkoxyalkyl, aryl, $C_{1-6}$aralkyl, heteroaryl, heterocyclyl, $C_{1-6}$heterocycloalkyl, $C_{1-6}$heteroaralkyl, carbocyclyl, and $C_{1-6}$carbocyclolalkyl;

R⁴ is selected from hydrogen, C₁₋₆aralkyl, and C₁₋₆alkyl;
R⁵ is heteroaryl; and
R⁶ and R⁷ are independently selected from hydrogen, C₁₋₆alkyl, and C₁₋₆aralkyl.

2. A compound of claim 1 or a pharmaceutically acceptable salt thereof, wherein Z is absent.

3. A compound of claim 1 or a pharmaceutically acceptable salt thereof, wherein R⁴, R⁶, and R⁷ are independently selected from hydrogen and methyl.

4. A compound of claim 1 or a pharmaceutically acceptable salt thereof, wherein L is C=O.

5. A compound of claim 1 or a pharmaceutically acceptable salt thereof, wherein R¹, R², and R³ are independently selected from hydrogen, C₁₋₆alkyl, C₁₋₆alkenyl, C₁₋₆alkynyl, C₁₋₆hydroxyalkyl, C₁₋₆alkoxyalkyl, C₁₋₆aralkyl, C₁₋₆heterocycloalkyl, C₁₋₆heteroaralkyl, and C₁₋₆carbocyclolalkyl.

6. A compound of claim 5 or a pharmaceutically acceptable salt thereof, wherein any of R¹, R², and R³ are independently C₁₋₆alkyl.

7. A compound of claim 6 or a pharmaceutically acceptable salt thereof, wherein any of R¹, R², and R³ are independently selected from methyl, ethyl, propyl, isopropyl, butyl, sec-butyl, and isobutyl.

8. A compound of claim 5 or a pharmaceutically acceptable salt thereof, wherein any of R¹, R², and R³ are independently propargyl.

9. A compound of claim 5 or a pharmaceutically acceptable salt thereof, wherein any of R¹, R², and R³ are independently C₁₋₆hydroxyalkyl.

10. A compound of claim 9 or a pharmaceutically acceptable salt thereof, wherein any of R¹, R², and R³ are independently selected from hydroxymethyl and hydroxyethyl.

11. A compound of claim 5 or a pharmaceutically acceptable salt thereof, wherein any of R¹, R², and R³ are independently C₁₋₆alkoxyalkyl.

12. A compound of claim 11 or a pharmaceutically acceptable salt thereof, wherein any of R¹, R², and R³ are independently selected from methoxymethyl and methoxyethyl.

13. A compound of claim 5 or a pharmaceutically acceptable salt thereof, wherein any of R¹, R², and R³ are independently C₁₋₆heteroaralkyl.

14. A compound of claim 13 or a pharmaceutically acceptable salt thereof, wherein any of R¹, R², and R³ are independently selected from imidazolylmethyl, pyrazolylmethyl, and thiazolylmethyl, and pyridylmethyl.

15. A compound of claim 5 or a pharmaceutically acceptable salt thereof, wherein any of R¹, R², and R³ are independently cyclohexylmethyl.

16. A compound of claim 1 or a pharmaceutically acceptable salt thereof, wherein R¹, R², and R³ are all different.

17. A compound of claim 1 or a pharmaceutically acceptable salt thereof, wherein at least one of R¹ and R² is selected from C₁₋₆hydroxyalkyl and C₁₋₆alkoxyalkyl.

18. A compound of claim 17 or a pharmaceutically acceptable salt thereof, wherein at least one of R¹ and R² is C₁₋₆alkoxyalkyl.

19. A compound of claim 18 or a pharmaceutically acceptable salt thereof, wherein at least one of R¹ and R² is selected from methoxymethyl and methoxyethyl.

20. A compound of claim 5 or a pharmaceutically acceptable salt thereof, wherein R³ is selected from C₁₋₆alkyl and C₁₋₆aralkyl.

21. A compound of claim 20 or a pharmaceutically acceptable salt thereof, wherein R³ is C₁₋₆alkyl.

22. A compound of claim 21 or a pharmaceutically acceptable salt thereof, wherein R³ is selected from methyl, ethyl, isopropyl, sec-butyl, and isobutyl.

23. A compound of claim 22 or a pharmaceutically acceptable salt thereof, wherein R³ is isobutyl.

24. A compound of claim 20 or a pharmaceutically acceptable salt thereof, wherein R³ is C₁₋₆aralkyl.

25. A compound of claim 24 or a pharmaceutically acceptable salt thereof, wherein R³ is phenylmethyl.

26. A compound of claim 1 or a pharmaceutically acceptable salt thereof, wherein R⁵ is 5- or 6-membered heteroaryl.

27. A compound of claim 26 or a pharmaceutically acceptable salt thereof, wherein R⁵ is selected from isoxazole, isothiazole, furan, thiophene, oxazole, thiazole, pyrazole, or imidazole.

28. A compound of claim 27 or a pharmaceutically acceptable salt thereof, wherein R⁵ is selected from isoxazole, furan, or thiophene.

29. A compound of claim 28 or a pharmaceutically acceptable salt thereof, wherein R⁵ is furan or thiophene.

30. A compound of claim 29 or a pharmaceutically acceptable salt thereof, wherein R⁵ is unsubstituted furan-3-yl or thien-2-yl.

31. A compound of claim 28 or a pharmaceutically acceptable salt thereof, wherein R⁵ is isoxazol-3-yl or isoxazol-5-yl.

32. A compound of claim 31 or a pharmaceutically acceptable salt thereof, wherein R⁵ is isoxazol-3-yl that has a substituent at the 5-position.

33. A compound of claim 31 or a pharmaceutically acceptable salt thereof, wherein R⁵ is isoxazol-5-yl that has a substituent at the 3-position.

34. A compound of claim 32 or 33 or a pharmaceutically acceptable salt thereof, wherein the substituent is selected from C₁₋₆alkyl, C₁₋₆alkoxy, C₁₋₆alkoxyalkyl, C₁₋₆hydroxyalkyl, carboxylic acid, aminocarboxylate, C₁₋₆alkylaminocarboxylate, (C₁₋₆alkyl)₂aminocarboxylate, C₁₋₆alkylcarboxylate, C₁₋₆heteroaralkyl, C₁₋₆aralkyl, C₁₋₆heterocycloalkyl, and C₁₋₆carbocycloalkyl.

35. A compound of claim 34 or a pharmaceutically acceptable salt thereof, wherein the substituent is selected from methyl, ethyl, isopropyl, and cyclopropylmethyl.

36. A compound of claim 34 or a pharmaceutically acceptable salt thereof, wherein the substituent is selected from C₁₋₆heteroaralkyl and C₁₋₆heterocycloalkyl.

37. A compound of claim 36 or a pharmaceutically acceptable salt thereof, wherein the substituent is 1,2,4-triazol-5-ylmethyl.

38. A compound of claim 36 or a pharmaceutically acceptable salt thereof, wherein the substituent is azetidin-1-ylmethyl.

39. A compound of claim 36 or a pharmaceutically acceptable salt thereof, wherein the substituent is

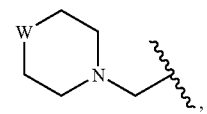

wherein W is O, NR, or CH₂, and R is H or C₁₋₆alkyl.

40. A compound of claim 39 or a pharmaceutically acceptable salt thereof, wherein W is O.

41. A compound of claim 36 or a pharmaceutically acceptable salt thereof, wherein the substituent is selected from C₁₋₆alkoxy and C₁₋₆alkoxyalkyl.

42. A compound of claim 41 or a pharmaceutically acceptable salt thereof, wherein the substituent is selected from methoxy, ethoxy, methoxymethy, and methoxyethyl.

43. A compound of claim 36 or a pharmaceutically acceptable salt thereof, wherein the substituent is selected from carboxylic acid, aminocarboxylate, $C_{1-6}$alkylaminocarboxylate, $(C_{1-6}alkyl)_2$aminocarboxylate, or $C_{1-6}$alkylcarboxylate.

44. A compound of claim 43 or a pharmaceutically acceptable salt thereof, wherein the substituent is methyl carboxylate.

45. A compound selected from

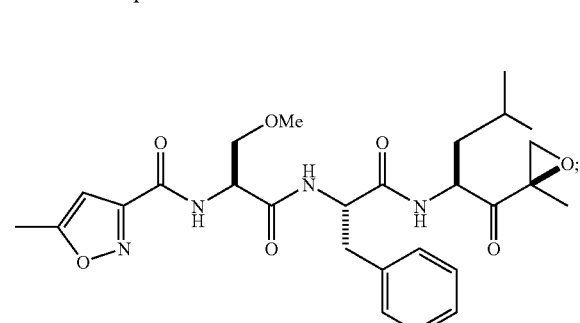

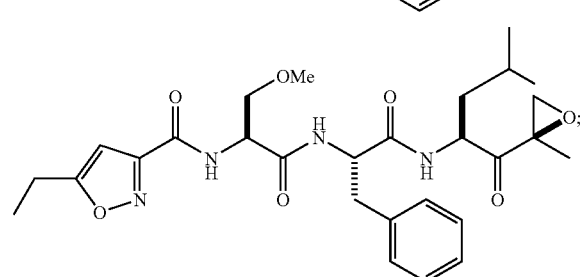

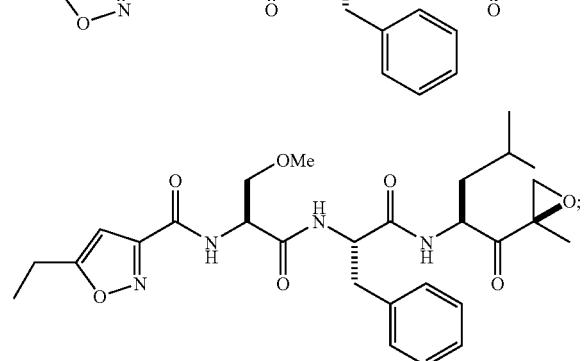

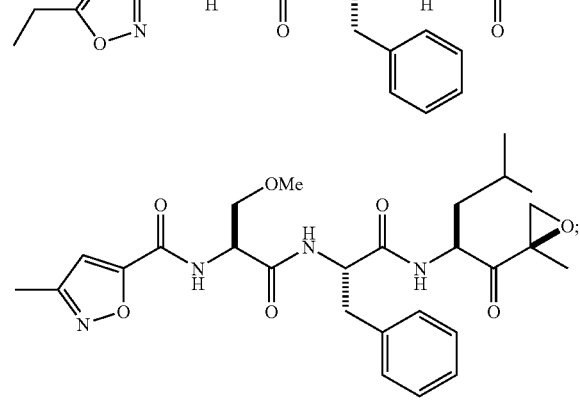

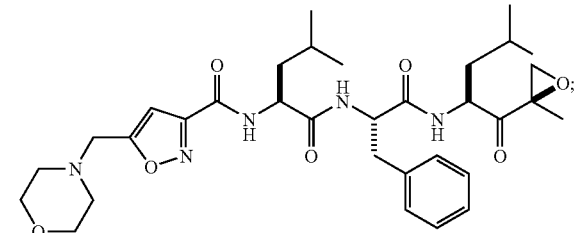

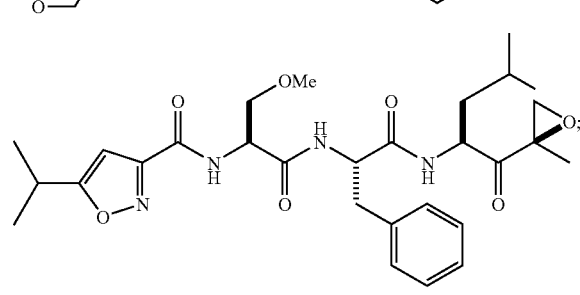

-continued

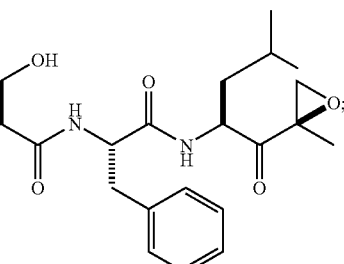

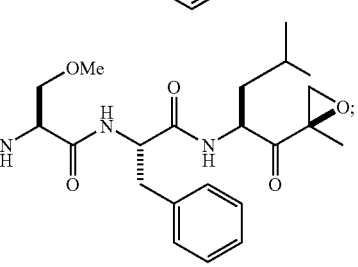

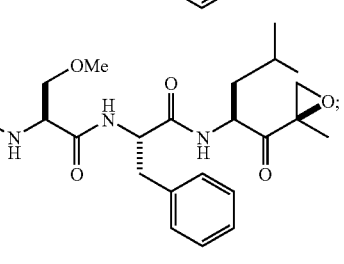

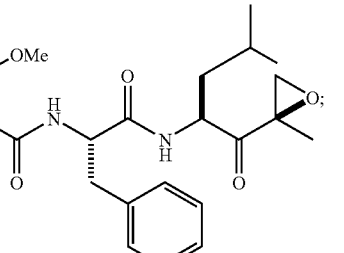

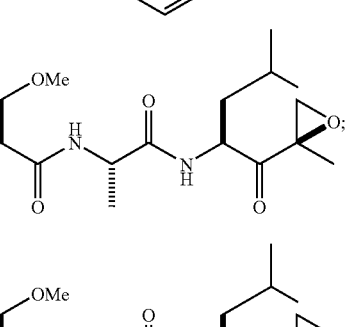

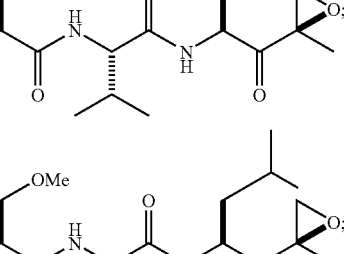

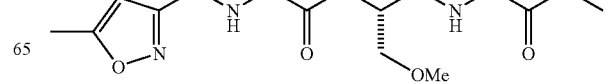

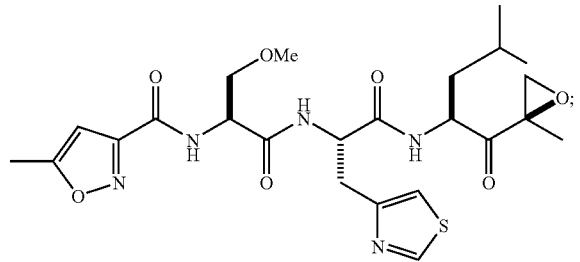
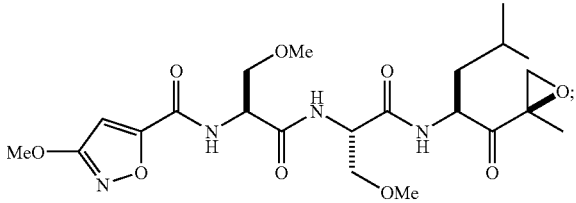
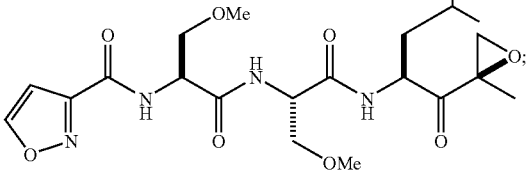
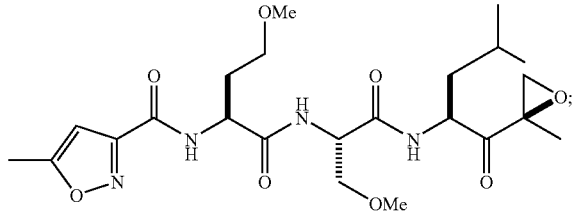
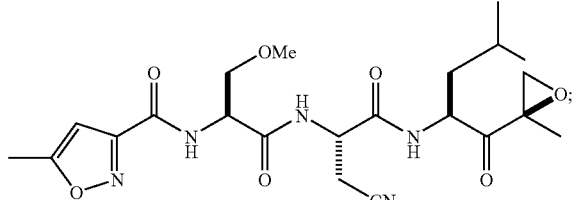
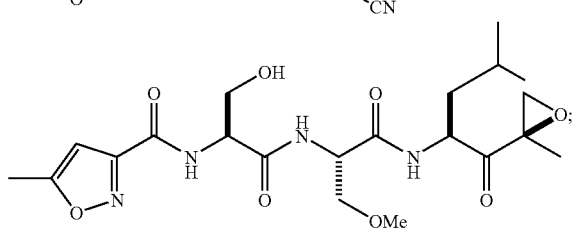
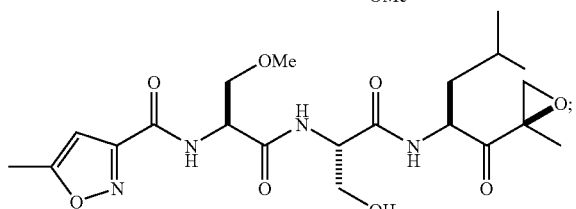
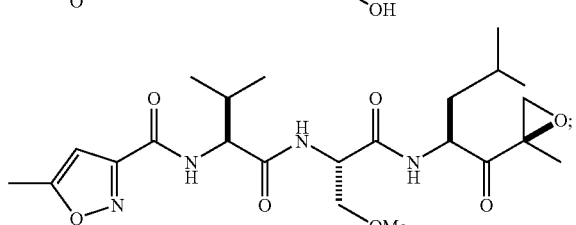
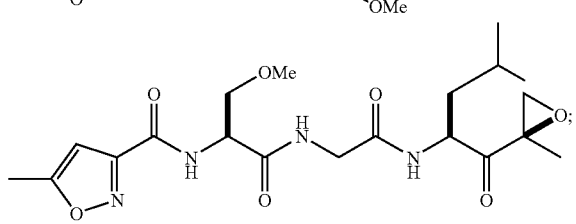

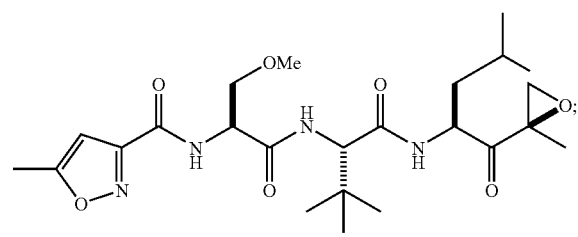
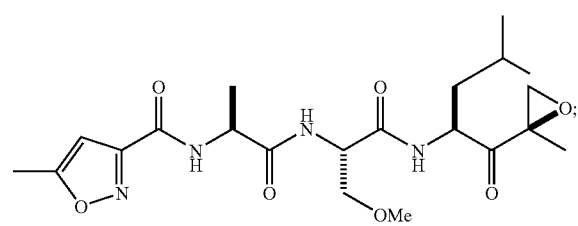
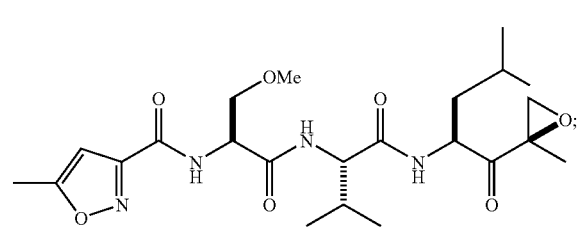
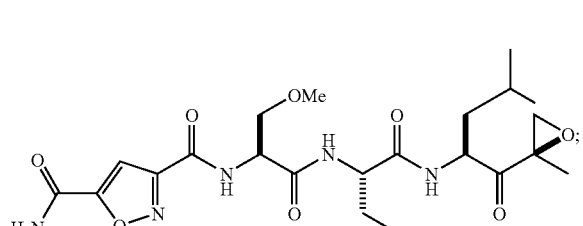
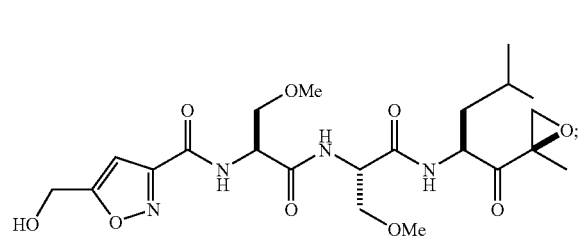
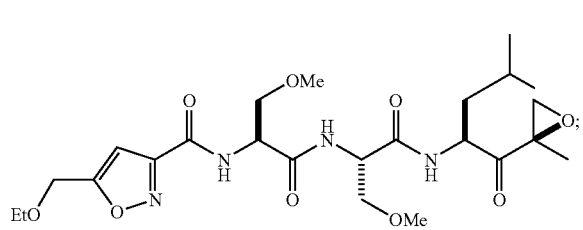
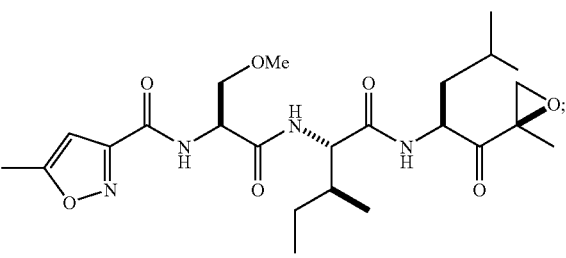
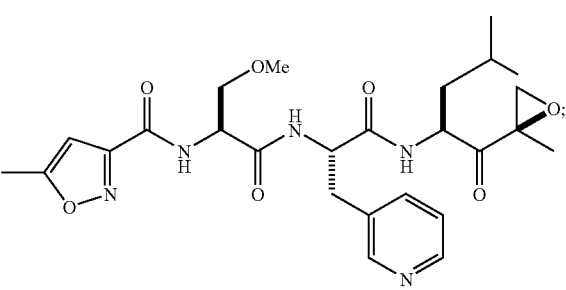
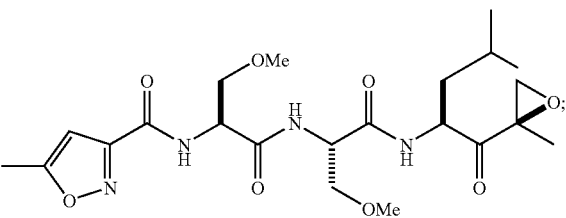
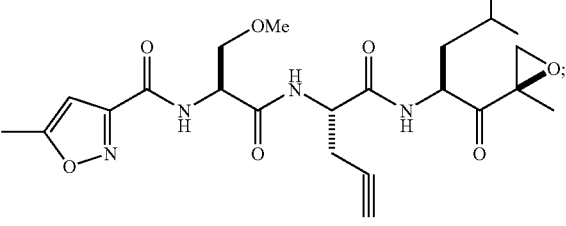
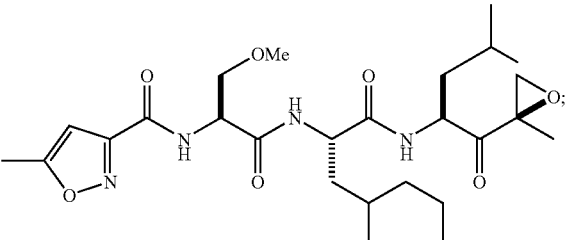
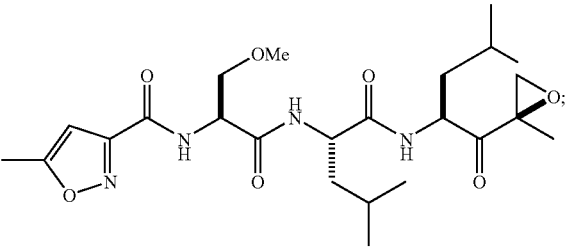

81
-continued
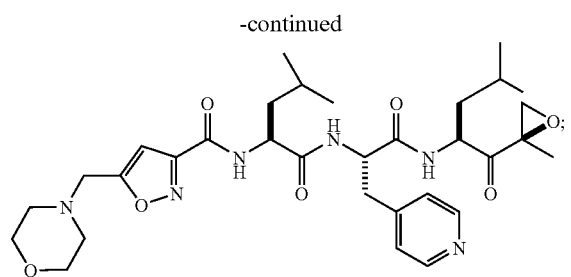
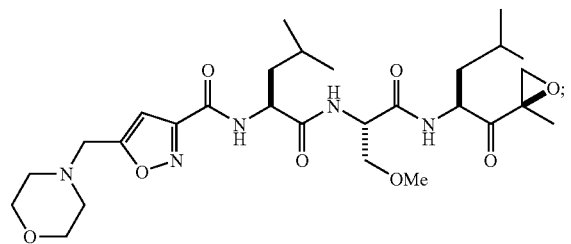
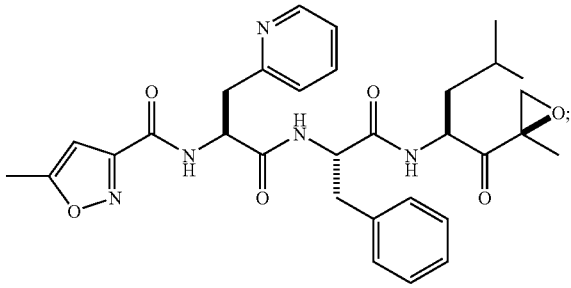
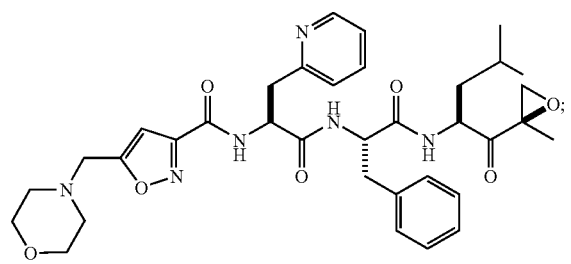
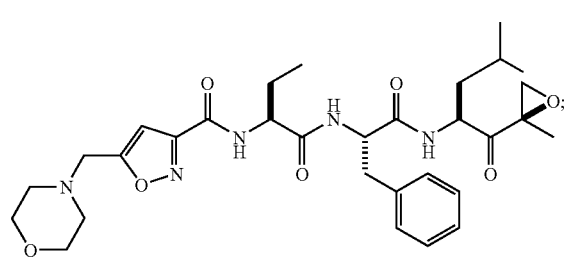
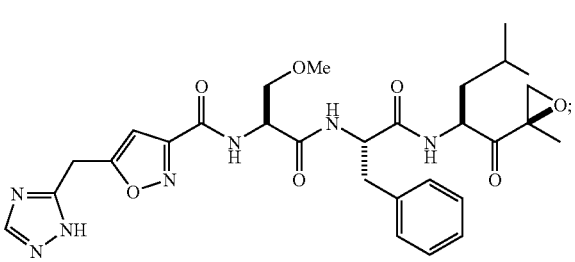
82
-continued
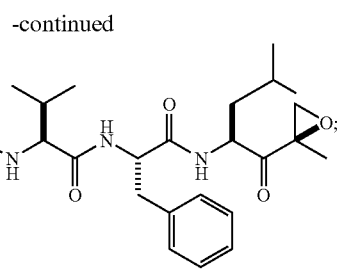
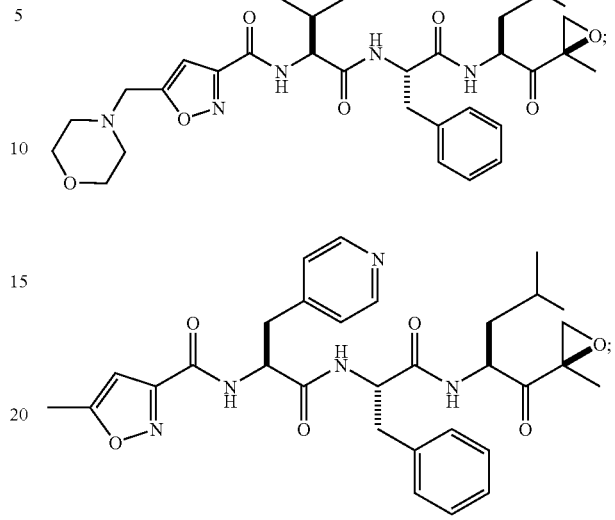
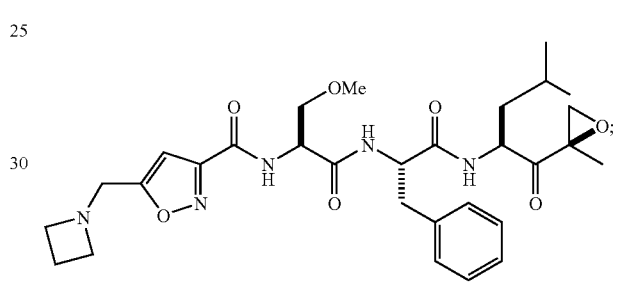
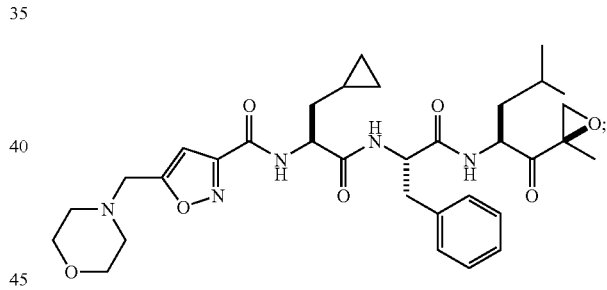
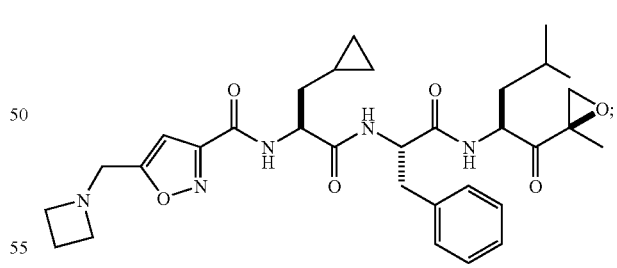
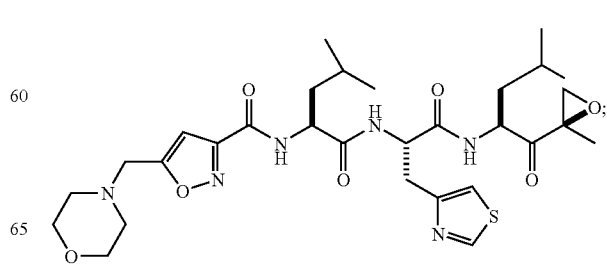

83
-continued
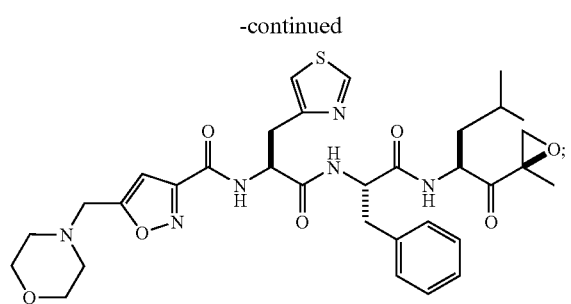
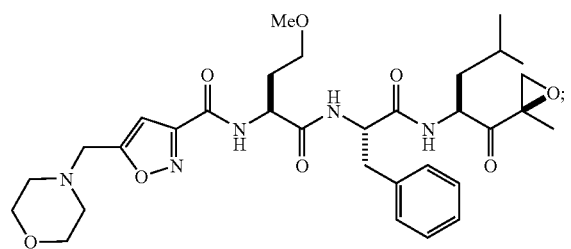
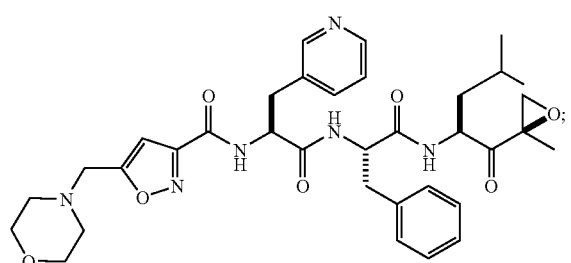
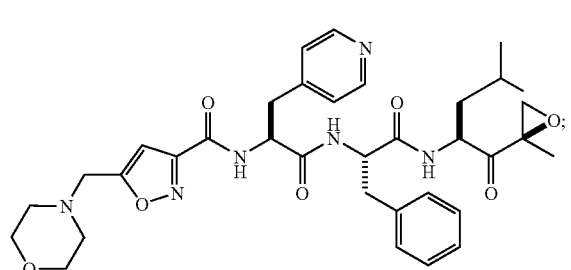
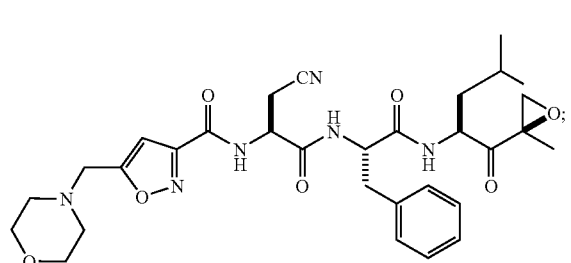
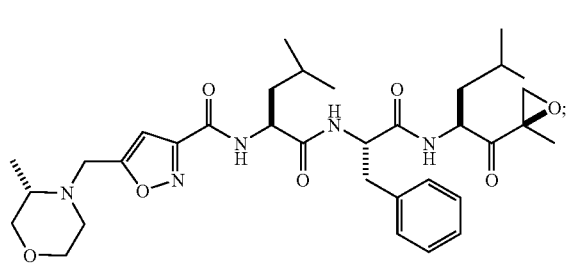
84
-continued
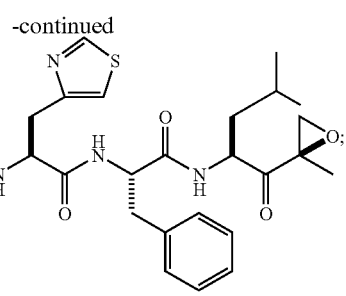
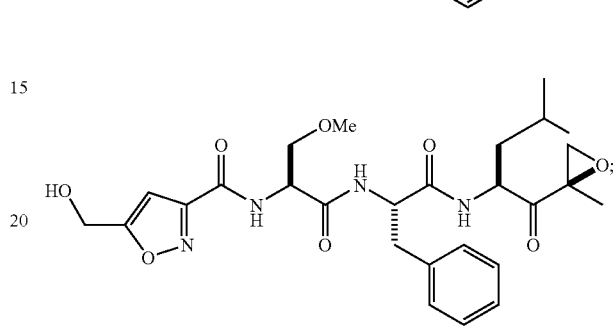
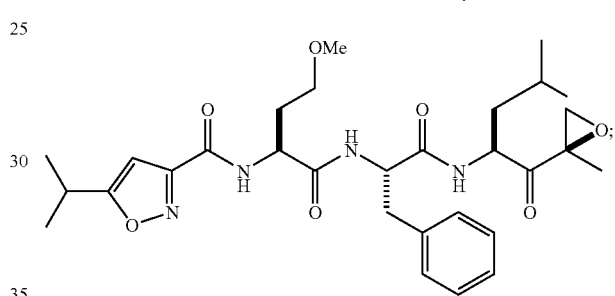
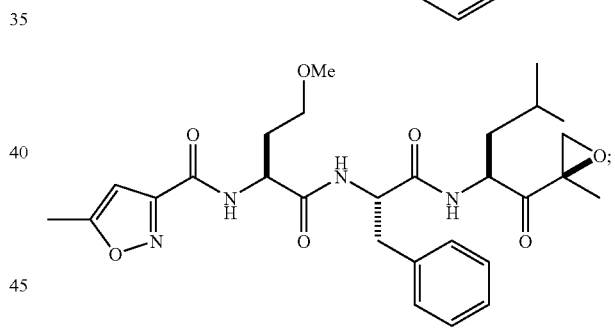
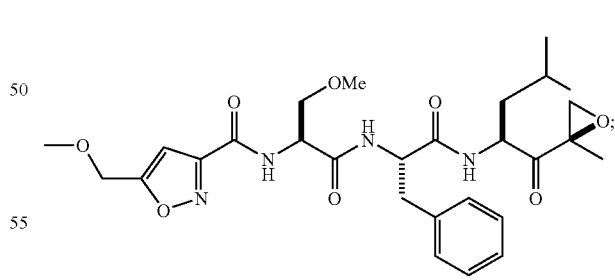
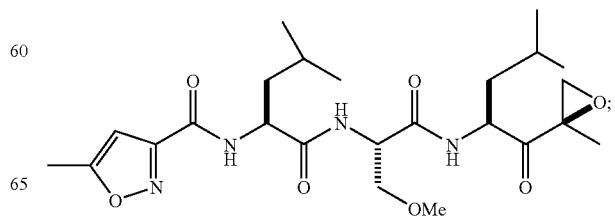

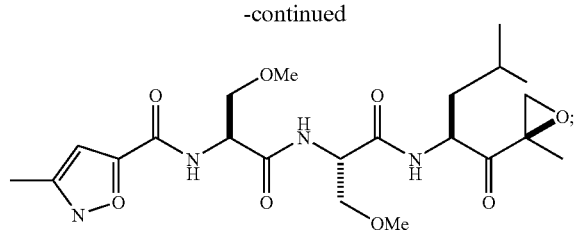
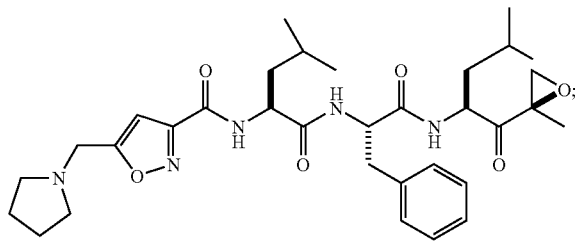
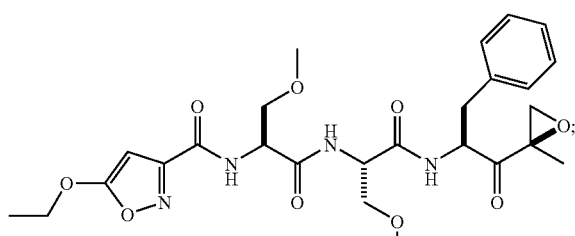
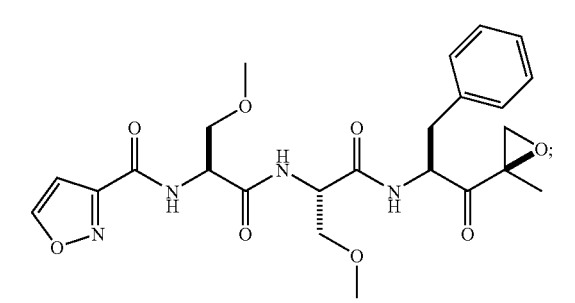
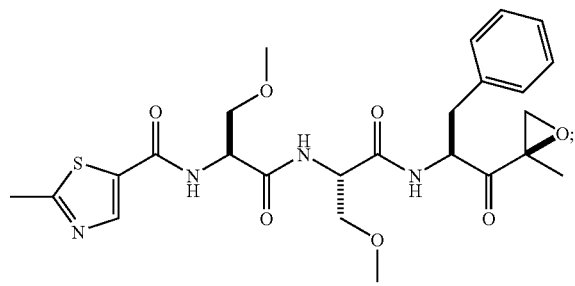
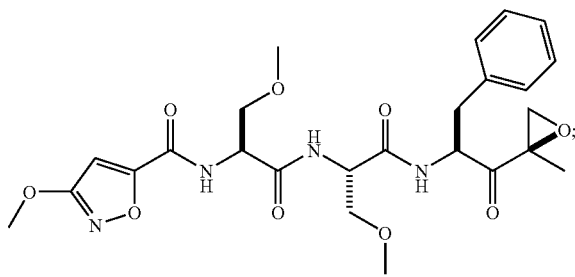
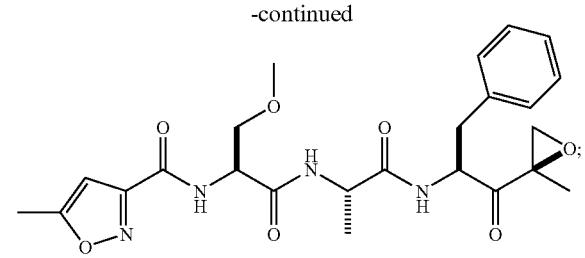
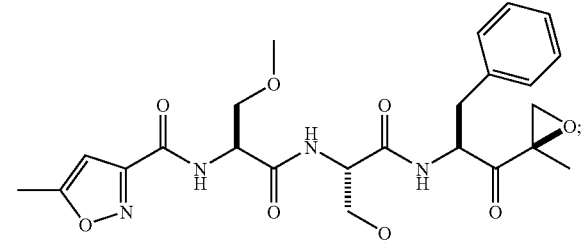
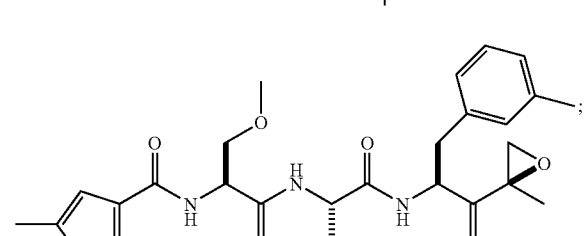
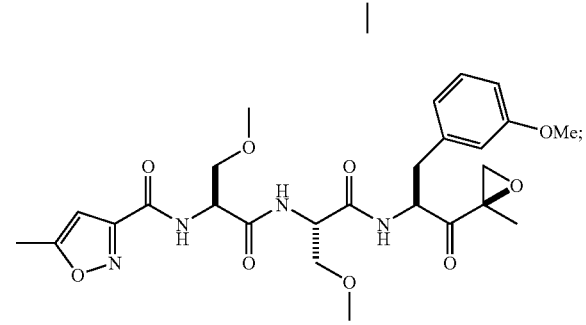
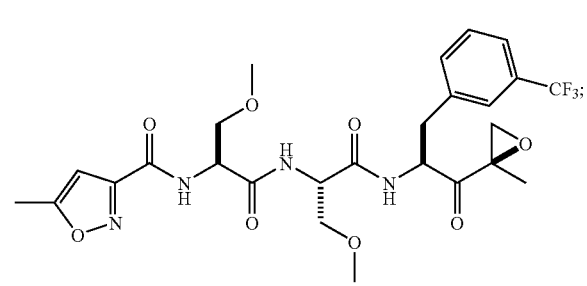
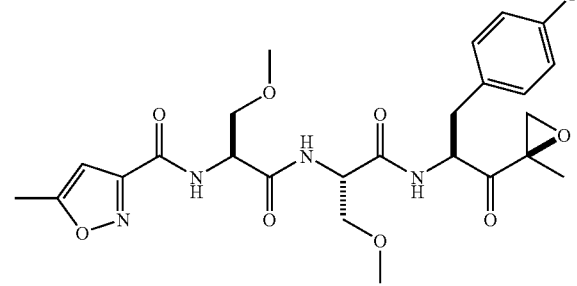

-continued

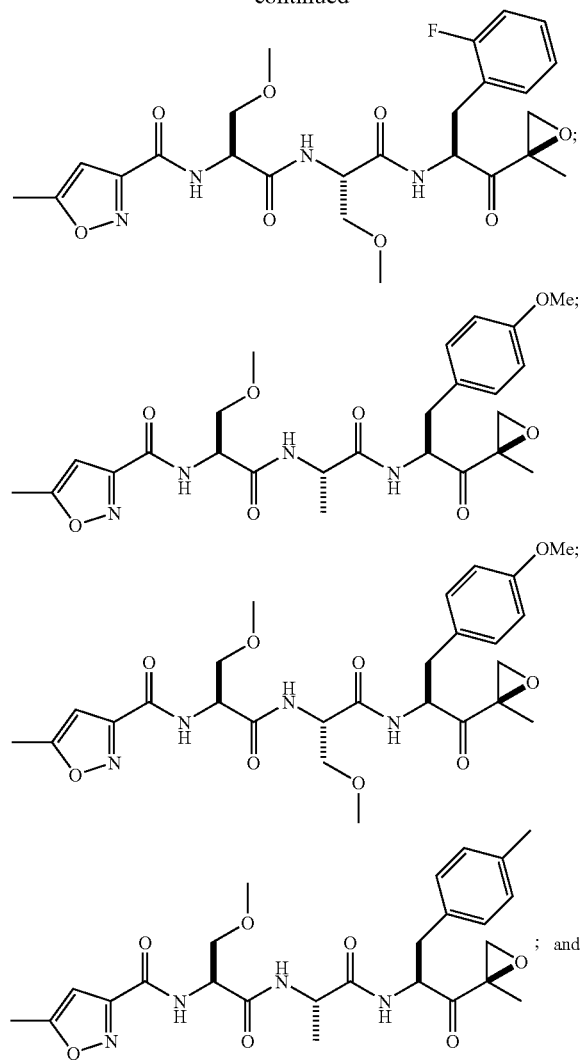

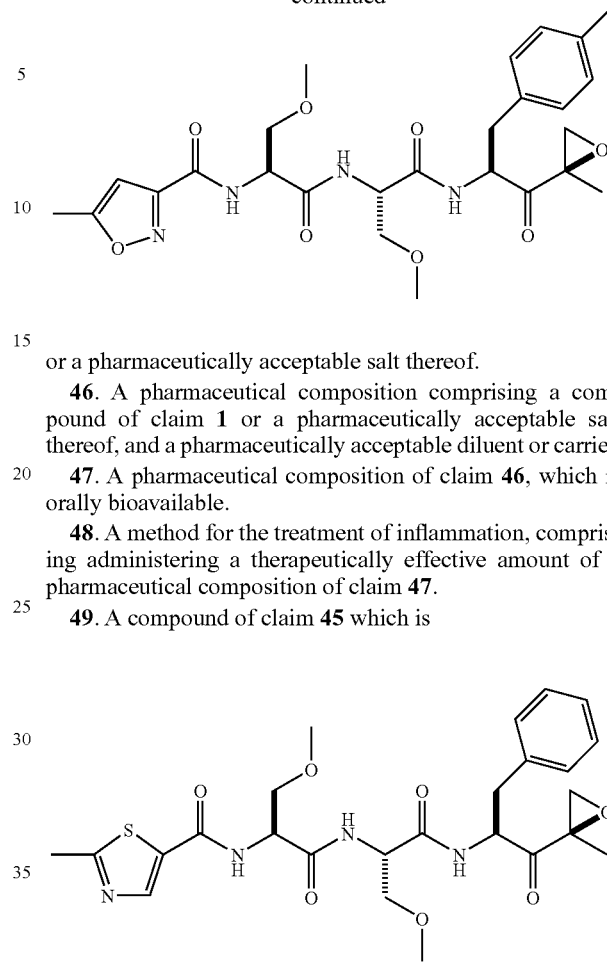

or a pharmaceutically acceptable salt thereof.

46. A pharmaceutical composition comprising a compound of claim 1 or a pharmaceutically acceptable salt thereof, and a pharmaceutically acceptable diluent or carrier.

47. A pharmaceutical composition of claim 46, which is orally bioavailable.

48. A method for the treatment of inflammation, comprising administering a therapeutically effective amount of a pharmaceutical composition of claim 47.

49. A compound of claim 45 which is or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,687,456 B2 | Page 1 of 1 |
| APPLICATION NO. | : 11/595804 | |
| DATED | : March 30, 2010 | |
| INVENTOR(S) | : Zhou et al. | |

It is certified that error appears in the above-identified patent and that said Letters Patent is hereby corrected as shown below:

In claim 41, column 74, line 65, please replace "claim 36" with --claim 34--;

In claim 43, column 75, line 4, please replace "claim 36" with --claim 34--.

Signed and Sealed this
Nineteenth Day of July, 2011

David J. Kappos
*Director of the United States Patent and Trademark Office*